US009249161B2

(12) United States Patent
Albrecht et al.

(10) Patent No.: US 9,249,161 B2
(45) Date of Patent: Feb. 2, 2016

(54) BROMODOMAIN INHIBITORS AND USES THEREOF

(75) Inventors: Brian K. Albrecht, Cambridge, MA (US); James Edmund Audia, Cambridge, MA (US); Alexandre Côté, Cambridge, MA (US); Victor S. Gehling, Somerville, MA (US); Jean-Christophe Harmange, Andover, MA (US); Michael Charles Hewitt, Brookline, MA (US); Christopher G. Nasveschuk, Stoneham, MA (US); Alexander M. Taylor, Cambridge, MA (US); Rishi G. Vaswani, Newton, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 28 days.

(21) Appl. No.: 13/990,906

(22) PCT Filed: Dec. 2, 2011

(86) PCT No.: PCT/US2011/063173
§ 371 (c)(1),
(2), (4) Date: Sep. 20, 2013

(87) PCT Pub. No.: WO2012/075456
PCT Pub. Date: Jun. 7, 2012

(65) Prior Publication Data
US 2014/0005169 A1    Jan. 2, 2014

Related U.S. Application Data

(60) Provisional application No. 61/419,119, filed on Dec. 2, 2010, provisional application No. 61/540,725, filed on Sep. 29, 2011.

(51) Int. Cl.
| | |
|---|---|
| *C07D 513/20* | (2006.01) |
| *C07D 498/10* | (2006.01) |
| *C07D 487/10* | (2006.01) |
| *C07D 495/22* | (2006.01) |
| *C07D 495/14* | (2006.01) |
| *C07D 495/20* | (2006.01) |
| *C07D 498/04* | (2006.01) |
| *C07D 498/14* | (2006.01) |
| *C07D 513/14* | (2006.01) |

(52) U.S. Cl.
CPC ............ *C07D 513/20* (2013.01); *C07D 487/10* (2013.01); *C07D 495/14* (2013.01); *C07D 495/20* (2013.01); *C07D 495/22* (2013.01); *C07D 498/04* (2013.01); *C07D 498/10* (2013.01); *C07D 498/14* (2013.01); *C07D 513/14* (2013.01)

(58) Field of Classification Search
USPC ............ 514/210.21, 220, 215; 540/560, 543, 540/578
See application file for complete search history.

(56) References Cited

U.S. PATENT DOCUMENTS

| | | | |
|---|---|---|---|
| 3,523,939 A | 8/1970 | Fryer et al. | |
| 3,681,343 A | 8/1972 | Hester, Jr. | |
| 3,709,898 A | 1/1973 | Hester, Jr. | |
| 3,763,144 A | 10/1973 | Hellerback et al. | |
| 3,781,289 A | 12/1973 | Hester, Jr. | |
| 3,850,942 A | 11/1974 | Hester et al. | |
| 3,886,141 A | 5/1975 | Chase | |
| 3,903,103 A | 9/1975 | Hester, Jr. | |
| 3,910,944 A * | 10/1975 | Gall ............................. 540/543 |
| 3,966,736 A | 6/1976 | Szmuszkovicz | |
| 4,110,455 A | 8/1978 | von Bebenburg et al. | |
| 4,155,904 A | 5/1979 | Schlesinger | |
| 4,327,026 A | 4/1982 | Branca et al. | |
| 4,374,773 A | 2/1983 | Branca et al. | |
| 4,377,522 A | 3/1983 | Branca et al. | |
| 4,455,307 A | 6/1984 | Hester, Jr. | |
| 4,820,834 A | 4/1989 | Evans et al. | |
| 4,959,361 A | 9/1990 | Walser | |
| 4,992,437 A | 2/1991 | Naka et al. | |
| 5,004,741 A | 4/1991 | Evans et al. | |
| 5,175,159 A | 12/1992 | Bock et al. | |
| 5,185,331 A | 2/1993 | Freidinger et al. | |
| 5,185,442 A | 2/1993 | Weber et al. | |

(Continued)

FOREIGN PATENT DOCUMENTS

| | | | |
|---|---|---|---|
| CA | 2020806 A1 | 1/1991 | |
| CA | 2032222 A1 | 6/1991 | |

(Continued)

OTHER PUBLICATIONS

Proctor, George R., et al., "Azabenzycycloheptones, Part 19, Formation of Some Heterocyclic Annulated Compounds from 1,2,3,4-tetrahydro-1-benzazepine derivatives," Journal of the Chemical Society, Perkin Transactions 1, Chemical Society, Letchworth, GB, Jan. 1, 1978, pp. 862-879.

Venkateswarlu, Peesapati, et al., "Synthesis and Biological Activity of Some New Heterocyclic Annelated Compounds from 2,3,4,5-tetrahydro-1-benzazepines," Indian Journal of Chemistry: IJC, Council of Scientific and Industrial Research, IN., vol. 35B, Dec. 1, 1996, pp. 1287-1293.

Grey, R., et al., "Structure-Based Design of 3-Aryl-6-Amino-Triazolo[4,3-b] Pyridazine Inhibitors of Pim-1 Kinase," Bioorg. Med, Chem, Lett., vol. 19, No. 11, Jun. 1, 2009, pp. 3019-3022.

(Continued)

*Primary Examiner* — Kathrien Cruz
(74) *Attorney, Agent, or Firm* — McCarter English LLP; Steven G. Davis; Michael J. DeGrazia

(57) ABSTRACT

The present invention relates to compounds useful as inhibitors of bromodomain-containing proteins. The invention also provides pharmaceutically acceptable compositions comprising compounds of the present invention and methods of using said compositions in the treatment of various disorders.

12 Claims, No Drawings

(56) References Cited

U.S. PATENT DOCUMENTS

| | | |
|---|---|---|
| 5,206,234 A | 4/1993 | Bock et al. |
| 5,382,579 A | 1/1995 | Okano et al. |
| 5,409,909 A | 4/1995 | Okano et al. |
| 5,428,004 A | 6/1995 | Earley et al. |
| 5,439,905 A | 8/1995 | Naka et al. |
| 5,550,126 A | 8/1996 | Horwell et al. |
| 5,593,988 A | 1/1997 | Tahara et al. |
| 5,681,833 A | 10/1997 | Castro Pineiro et al. |
| 5,683,998 A | 11/1997 | Shibayama et al. |
| 5,698,552 A | 12/1997 | Weber et al. |
| 5,712,274 A | 1/1998 | Sueoka et al. |
| 5,721,231 A | 2/1998 | Moriwaki et al. |
| 5,733,905 A | 3/1998 | Albright et al. |
| 5,739,129 A | 4/1998 | Aquino et al. |
| 5,753,647 A | 5/1998 | Weber et al. |
| 5,753,649 A | 5/1998 | Tahara et al. |
| 5,795,887 A | 8/1998 | Aquino et al. |
| 5,840,895 A | 11/1998 | Ohtsuka et al. |
| 5,843,941 A | 12/1998 | Marsters, Jr. et al. |
| 5,869,483 A | 2/1999 | Albright et al. |
| 5,929,069 A | 7/1999 | Shudo |
| 6,121,256 A | 9/2000 | Shudo |
| 6,433,167 B1 | 8/2002 | Fujita et al. |
| 6,458,782 B1 | 10/2002 | Kagechika et al. |
| 6,476,017 B2 | 11/2002 | Shudo |
| 6,649,366 B2 | 11/2003 | Chunbinskaya et al. |
| 6,777,408 B1 | 8/2004 | Liberatore et al. |
| 7,015,213 B1 | 3/2006 | Bigg et al. |
| 7,160,880 B1 | 1/2007 | Feldman et al. |
| 7,250,410 B2 | 7/2007 | Bourguignon et al. |
| 7,435,730 B2 | 10/2008 | Feldman et al. |
| 7,442,795 B2 | 10/2008 | Bryans et al. |
| 7,473,689 B2 | 1/2009 | Feldman et al. |
| 7,482,337 B2 | 1/2009 | Himmelsbach et al. |
| 7,485,635 B2 | 2/2009 | Feldman et al. |
| 7,528,127 B2 | 5/2009 | Feldman et al. |
| 7,696,212 B2 | 4/2010 | Himmelsbach et al. |
| 2001/0039272 A1 | 11/2001 | Shudo |
| 2002/0052358 A1 | 5/2002 | Chubinskaya et al. |
| 2004/0053919 A1 | 3/2004 | Chubinskaya et al. |
| 2004/0138214 A1 | 7/2004 | Himmelsbach et al. |
| 2004/0152888 A1 | 8/2004 | Bourguignon et al. |
| 2006/0128695 A1 | 6/2006 | Bourguignon et al. |
| 2007/0093475 A1 | 4/2007 | Feldman et al. |
| 2007/0105844 A1 | 5/2007 | Glick et al. |
| 2007/0135419 A1 | 6/2007 | Feldman et al. |
| 2007/0135420 A1 | 6/2007 | Feldman et al. |
| 2007/0135421 A1 | 6/2007 | Feldman et al. |
| 2009/0093457 A1 | 4/2009 | Himmelsbach et al. |
| 2010/0041643 A1 | 2/2010 | Adachi et al. |
| 2010/0144703 A1 | 6/2010 | Himmelsbach et al. |
| 2010/0256123 A1 | 10/2010 | Sakuma et al. |
| 2010/0286127 A1 | 11/2010 | Miyoshi et al. |
| 2010/0331316 A1 | 12/2010 | Paoletti et al. |
| 2011/0230460 A1 | 9/2011 | Kempen et al. |

FOREIGN PATENT DOCUMENTS

| | | |
|---|---|---|
| CA | 2032427 A1 | 6/1991 |
| CA | 2050268 A1 | 3/1992 |
| CA | 2056809 A1 | 6/1992 |
| CA | 2059353 A1 | 7/1992 |
| CA | 2062456 A1 | 9/1992 |
| CA | 2071092 A1 | 12/1992 |
| CA | 1327570 C | 3/1994 |
| CA | 02258053 A1 | 12/1997 |
| DE | 2640599 A1 | 3/1978 |
| DE | 3936828 A1 | 5/1990 |
| DE | 4006471 A1 | 9/1990 |
| DE | 4027470 A1 | 3/1992 |
| DE | 4107521 A1 | 9/1992 |
| DE | 4128581 A1 | 3/1993 |
| DE | 4219659 A1 | 12/1993 |
| EP | 0169392 A2 | 1/1986 |
| EP | 0315698 A1 | 5/1989 |
| EP | 0328924 A2 | 8/1989 |
| EP | 0342587 A2 | 11/1989 |
| EP | 0348523 A1 | 1/1990 |
| EP | 0367110 A1 | 5/1990 |
| EP | 0407955 A1 | 1/1991 |
| EP | 0480455 A1 | 4/1992 |
| EP | 495473 A1 | 7/1992 |
| EP | 0514125 A1 | 11/1992 |
| EP | 0559891 A1 | 9/1993 |
| EP | 0656361 A4 | 1/1995 |
| EP | 636625 A2 | 2/1995 |
| EP | 0661284 A4 | 5/1995 |
| EP | 0692483 A4 | 11/1995 |
| EP | 0989131 A1 | 3/2000 |
| EP | 1297836 A1 | 4/2003 |
| EP | 1887008 A1 | 2/2008 |
| EP | 2239264 A1 | 10/2010 |
| FR | 2154511 A1 | 5/1973 |
| FR | 2220257 A1 | 10/1974 |
| GB | 1409693 A | 10/1975 |
| GB | 2259013 A | 3/1993 |
| JP | 7179471 | 7/1995 |
| JP | 11228576 | 8/1999 |
| JP | 2959591 B2 | 10/1999 |
| JP | 3223290 B2 | 10/2001 |
| JP | 03264588 B2 | 3/2002 |
| JP | 03264589 B2 | 3/2002 |
| JP | 04226993 B2 | 2/2009 |
| WO | 9303717 A1 | 3/1993 |
| WO | 9307129 A1 | 4/1993 |
| WO | 9312791 A1 | 7/1993 |
| WO | 9313776 A1 | 7/1993 |
| WO | 9319052 A1 | 9/1993 |
| WO | 9406801 A1 | 3/1994 |
| WO | 9426723 A2 | 11/1994 |
| WO | 9514694 A1 | 6/1995 |
| WO | 9528399 A1 | 10/1995 |
| WO | 9711061 A1 | 3/1997 |
| WO | 9747622 A1 | 12/1997 |
| WO | 9811111 A1 | 3/1998 |
| WO | 9828268 A2 | 7/1998 |
| WO | 9858930 A1 | 12/1998 |
| WO | 9929324 A1 | 6/1999 |
| WO | 0006157 A1 | 2/2000 |
| WO | 0012547 A2 | 3/2000 |
| WO | 0054778 A1 | 9/2000 |
| WO | 0069836 A1 | 11/2000 |
| WO | 0147510 A2 | 7/2001 |
| WO | 02098865 A2 | 12/2002 |
| WO | 03/074525 A1 | 9/2003 |
| WO | 2004041258 A2 | 5/2004 |
| WO | 2004041820 A1 | 5/2004 |
| WO | 2004/058769 A2 | 7/2004 |
| WO | 2005/002590 A1 | 1/2005 |
| WO | 2005099759 A1 | 10/2005 |
| WO | 2006038560 A1 | 4/2006 |
| WO | 2006129623 A1 | 12/2006 |
| WO | 2007016087 A2 | 2/2007 |
| WO | 2007050587 A2 | 5/2007 |
| WO | 2007/079820 A1 | 7/2007 |
| WO | 2008023847 A1 | 2/2008 |
| WO | 2008109856 A2 | 9/2008 |
| WO | 2009059191 A1 | 5/2009 |
| WO | 2009081349 A1 | 7/2009 |
| WO | 2009152589 A1 | 12/2009 |
| WO | 2010008459 A1 | 1/2010 |
| WO | 2010049466 A1 | 5/2010 |
| WO | 2010121164 A2 | 10/2010 |
| WO | 2010128685 A1 | 11/2010 |
| WO | 2011037128 A1 | 3/2011 |
| WO | 2011054553 A1 | 5/2011 |
| WO | 2011054841 A1 | 5/2011 |
| WO | 2011054843 A1 | 5/2011 |
| WO | 2011054844 A1 | 5/2011 |
| WO | 2011054845 A1 | 5/2011 |
| WO | 2011054846 A1 | 5/2011 |
| WO | 2011054848 A1 | 5/2011 |
| WO | 2011054851 A1 | 5/2011 |

(56) References Cited

FOREIGN PATENT DOCUMENTS

| WO | 2011079315 A1 | 6/2011 |
|---|---|---|
| WO | 2011/123678 A2 | 10/2011 |
| WO | 2011143651 A1 | 11/2011 |
| WO | 2011143657 A1 | 11/2011 |
| WO | 2011143660 A2 | 11/2011 |
| WO | 2011143669 A2 | 11/2011 |
| WO | 2011/161031 A1 | 12/2011 |
| WO | 2012/075383 A2 | 6/2012 |
| WO | 2013024104 A1 | 2/2013 |
| WO | 2013030150 A1 | 3/2013 |
| WO | 2013033268 A2 | 3/2013 |
| WO | 2013033269 A1 | 3/2013 |
| WO | 2013033270 A2 | 3/2013 |
| WO | 2013033420 A1 | 3/2013 |

OTHER PUBLICATIONS

Filippakopoulos, et al., "Selective Inhibition of BET Bromodomains," Nature, Dec. 30, 2010, vol. 468, pp. 1067-1073.

Kosychova, L., et al., "Synthesis of Substitute 5,6-Dihydro-4H-[1,2,4]Triazolo[4,3-a][1,5]Benzodiazepines," Chemistry of Heterocyclic Compounds, vol. 40, No. 6, Jun. 2004, pp. 811-815.

Gussio, Rick, et al., "All-Atom Models for the Non-Nucleoside Binding Site of HIV-1 Reverse Transcriptase Complexed with Inhibitors: A 3D QSAR Approach," J. Med. Chem., Apr. 12, 1996, vol. 39, No. 8, pp. 1645-1650.

International Search Report and Written Opinion, dated Jul. 23, 2013, Int'l Appl'n No. PCT/US2013/044449, Int'l Filing Date Jun. 6, 2013.

International Search Report and Written Opinion, dated Feb. 21, 2013, Int'l Appl'n No. PCT/US2012/042825, Int'l Filing Date Jun. 15, 2012.

International Preliminary Report on Patentability, dated Nov. 5, 2013, Int'l Appl'n No. PCT/US2012/036569, Int'l Filing Date May 4, 2012.

International Search Report and Written Opinion, dated Jul. 23, 2013, Int'l Appl'n No. PCT/US2013/044444, Int'l Filing Date Jun. 6, 2013.

International Search Report and Written Opinion, dated Apr. 17, 2012, Int'l Appl'n No. PCT/US2011/063173, Int'l Filing Date Dec. 2, 2011.

International Preliminary Report on Patentability, mailed Jan. 3, 2014, International Application No. PCT/US2012/042825; International Filing Date: Jun. 15, 2012, 10 pages.

Terrett, N.K., et al., "Imidazoú2',3':6,5 3/4 Dipyridoú3,2-B:2',3'-E 3/4-1,4-Diazepines: Non-Nucleoside HIV-1 Reverse Transcriptase Inhibitors with Greater Enzyme Affinity than Nevirapine," Bioorganic & Medicinal Chemistry Letters, vol. 12, No. 2, Dec. 1, 1992, pp. 1745-1750, XP002912883.

Kosychova, et al., "Synthesis of New [1,2,4]triazolo[4,3-a][1,5]benzodiaze-pine derivatives," Lietuvos Mokslu Akademija. Chemija, vol. 22, No. 1, Jan. 1, 2011, pp. 60-64, XP055136653.

Kosychova, et al., "Synthesis of novel 5,6-dihydro-4H-[1,2,4] triazolo[4,3-a][1,5]benzodiazepines," Rigas Tehniskas Universitates Zinatniskie Raksti. Serija 1: Materialzinatne Un Lietiska Kimija, vol. 22, Jan. 1, 2010, pp. 94-99, XP009179817.

Di Bracco, M., et al., "1,5-Benzodiazepines. Part XII. Synthesis and Biological Evaluations of Tricyclic and Tetracyclic 1,5-benzodiazepine Derivatives as Nevirapine Analogues," European Journal of Medicinal Chemistry, vol. 36, No. 11-12, Dec. 1, 2001, pp. 935-949, XP027205317.

Jiban K. Chakrabarti, et al., "Chemistry of Adamantane. Part XI. 1,2-Disubstituted Adamantanes. Synthesis and Reactions of Adamantano[2,1-b ]- and protoadamantano-[4,5-b ] [1,5]benzodiazepines," Journal of Heterocyclic Chemistry, vol. 15, No. 5, Aug. 1, 1978, pp. 705-710, XP055136791.

Szarvasi, E., et al., "(4H)Dihydro-5,6(s)-triazolo-(4,3-a)benzodiazepines-1,5 a activite analgesique et anti-inflammatoire," European Journal of Medicinal Chemistry, vol. 13, No. 2, Mar. 1, 1978, pp. 113-119, XP009179828.

* cited by examiner

BROMODOMAIN INHIBITORS AND USES THEREOF

CROSS-REFERENCE TO RELATED APPLICATIONS

The present application is a 35 U.S.C. §371 national stage filing of International Application No. PCT/US2011/063173, filed Dec. 2, 2011, which claims priority to U.S. provisional application Ser. No. 61/419,119, filed Dec. 2, 2010, and U.S. provisional application Ser. No. 61/540,725, filed Sep. 29, 2011 The entire contents of each of the aforementioned applications which are hereby incorporated herein by reference.

TECHNICAL FIELD OF THE INVENTION

The present invention relates to compounds useful as inhibitors of one or more bromodomain-containing proteins.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding proteins or chromatin-modifying enzymes. Significantly, an increasing number of these proteins have been associated with a variety of disorders such as neurodegenerative disorders, metabolic diseases, inflammation, and cancer. Thus, highly selective therapeutic agents directed against this emerging class of gene regulatory proteins promise new approaches to the treatment of human diseases.

SUMMARY OF THE INVENTION

It has now been found that compounds described herein, and pharmaceutically acceptable compositions thereof, are effective as inhibitors of one or more bromodomain-containing proteins. Such compounds include those of formulae I and II:

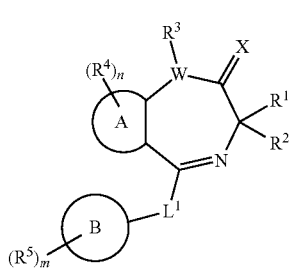

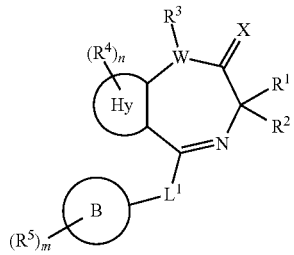

or a pharmaceutically acceptable salt thereof, wherein each of $R^1$, $R^2$, $R^3$, $R^4$, $R^5$, $L^1$, n, m, X, Hy, W, Ring A, and Ring B is as defined and described herein.

Provided compounds, and pharmaceutically acceptable compositions thereof, are useful for treating a variety of diseases, disorders or conditions associated with abnormal cellular responses triggered by events mediated by bromodomain-containing proteins. Such diseases, disorders, or conditions include those described herein.

Provided compounds are also useful for the study of bromodomain-containing proteins in biological and pathological phenomena, the study of intracellular signal transduction pathways mediated by bromodomain-containing proteins, and the comparative evaluation of new inhibitors of bromodomain-containing proteins.

DETAILED DESCRIPTION OF CERTAIN EMBODIMENTS

I. General Description of Compounds of the Invention

In certain embodiments, the present invention provides a compound of formula I:

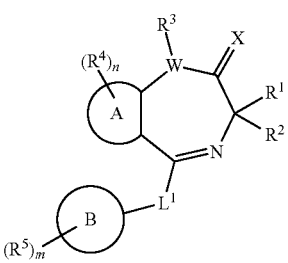

or a pharmaceutically acceptable salt thereof, wherein:
Ring A is benzo, or a 5-6 membered fused heteroaryl ring having 1-3 heteroatoms independently selected from nitrogen, oxygen, or sulfur;
Ring B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

$L^1$ is a covalent bond or an optionally substituted bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—;

$R^1$ is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$, or —(CH$_2$)$_p$R$^x$;

p is 0-3;

$R^x$ is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$;

$R^2$ is halogen, —CN, —SR, or optionally substituted $C_{1-6}$ aliphatic, or:

$R^1$ and $R^2$ are taken together with their intervening atoms to form an optionally substituted 3-7 membered saturated or partially unsaturated spiro-fused ring having 0-2 heteroatoms independently selected from nitrogen, oxygen, or sulfur;

each R is independently hydrogen or an optionally substituted group selected from $C_{1-6}$ aliphatic, phenyl, a 3-7 membered saturated or partially unsaturated carbocyclic ring, a 7-10 membered bicyclic saturated, partially unsaturated, or aryl ring, a 5-6 membered monocyclic heteroaryl ring having 1-3 heteroatoms independently selected from nitrogen, oxygen, and sulfur, a 4-7 membered saturated or partially unsaturated heterocyclic ring having 1-2 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R' on the same nitrogen are taken together with their intervening atoms to form an optionally substituted group selected from a 4-7 membered monocyclic saturated or partially unsaturated ring having 1-2 heteroatoms independently selected from nitrogen, oxygen, and sulfur, or a 7-12 membered bicyclic saturated, partially unsaturated, or aromatic fused ring having 1-3 heteroatoms independently selected from nitrogen, oxygen, and sulfur;

W is

$R^3$ is optionally substituted $C_{1-6}$ aliphatic;
X is oxygen or sulfur, or:

$R^3$ and X are taken together with their intervening atoms to form an optionally substituted 5-membered heteroaryl ring having 1-4 heteroatoms independently selected from nitrogen, oxygen, or sulfur;

each of m and n is independently 0-4, as valency permits; and each of $R^4$ and $R^5$ is independently —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$.

In certain embodiments, the present invention provides a compound of formula II:

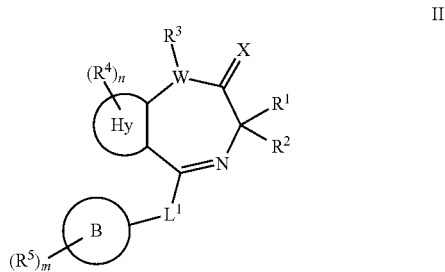

II or a pharmaceutically acceptable salt thereof, wherein:

Hy is a 5-membered fused heteroaryl ring having 2-3 heteroatoms independently selected from nitrogen, oxygen, or sulfur, or a 6-membered fused heteroaryl ring having 2-3 nitrogen atoms;

Ring B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

$L^1$ is a covalent bond or an optionally substituted bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—;

$R^1$ is hydrogen, halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$, or —(CH$_2$)$_p$R$^x$;

p is 0-3;

$R^x$ is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C (O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$;

R$^2$ is hydrogen, halogen, —CN, —SR, or optionally substituted C$_{1-6}$ aliphatic, or:
  R$^1$ and R$^2$ are taken together with their intervening atoms to form an optionally substituted 3-7 membered saturated or partially unsaturated spiro-fused ring having 0-2 heteroatoms independently selected from nitrogen, oxygen, or sulfur;

each R is independently hydrogen or an optionally substituted group selected from C$_{1-6}$ aliphatic, phenyl, a 3-7 membered saturated or partially unsaturated carbocyclic ring, a 7-10 membered bicyclic saturated, partially unsaturated, or aryl ring, a 5-6 membered monocyclic heteroaryl ring having 1-3 heteroatoms independently selected from nitrogen, oxygen, and sulfur, a 4-7 membered saturated or partially unsaturated heterocyclic ring having 1-2 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R' on the same nitrogen are taken together with their intervening atoms to form an optionally substituted group selected from a 4-7 membered monocyclic saturated or partially unsaturated ring having 1-2 heteroatoms independently selected from nitrogen, oxygen, and sulfur, or a 7-12 membered bicyclic saturated, partially unsaturated, or aromatic fused ring having 1-3 heteroatoms independently selected from nitrogen, oxygen, and sulfur;

W is

R$^3$ is optionally substituted C$_{1-6}$ aliphatic;
X is oxygen or sulfur, or:
  R$^3$ and X are taken together with their intervening atoms to form an optionally substituted 5-membered heteroaryl ring having 1-4 heteroatoms independently selected from nitrogen, oxygen, or sulfur;
each of m and n is independently 0-4, as valency permits; and
each of R$^4$ and R$^5$ is independently —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

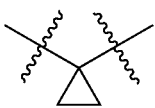

In other embodiments, a cycloalkylene group is a 1,2-cycloalkylene group or a 1,3-cycloalkylene group. Exemplary 1,2-cycloalkylene groups include

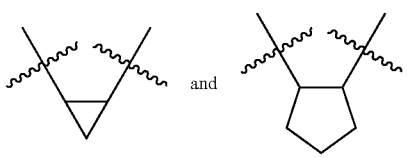

and

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "aryl" used alone or as part of a larger moiety as in "aralkyl", "aralkoxy", or "aryloxyalkyl", refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl"

refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[12.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "bivalent hydrocarbon" refers to a bivalent saturated or unsaturated hydrocarbon group. Such bivalent hydrocarbon groups include alkylene, alkenylene, and alkynylene groups.

An "alkylene" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

An "alkenylene" is a bivalent hydrocarbon chain having at least one double bond. Suitable substituents include those described below for a substituted aliphatic group.

An "alkynylene" is bivalent hydrocarbon chain having at least one triple bond. Suitable substituents include those described below for a substituted aliphatic group.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}$Ph, which may be substituted with $R^\circ$; —$(CH_2)_{0-4}O(CH_2)_{0-1}$Ph which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —OC(O)$(CH_2)_{0-4}$SR—, SC(S)$SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —SC(S)$SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; —$SiR^\circ_3$; —($C_{1-4}$ straight or branched)alkylene)O—$N(R^\circ)_2$; or —($C_{1-4}$ straight or branched)alkylene)C(O)O—$N(R^\circ)_2$, wherein each $R^\circ$ may be substituted as defined below and is independently hydrogen, $C_{1-6}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OR^\bullet$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —($C_{1-4}$ straight or branched alkylene)C(O)OR$^\bullet$, or —SSR$^\bullet$ wherein each $R^\bullet$ is unsubstituted or where preceded by "halo" is substituted only with one or more halogens, and is independently selected from $C_{1-4}$ aliphatic, —$CH_2$Ph, —$O(CH_2)_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =NNHC(O)$R^*$, =NNHC(O)O$R^*$, =NNHS(O)$_2R^*$, =N$R^*$, =NO$R^*$, —O(C($R^*_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "suitable amino protecting group," includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenz ylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

As used herein, the term "inhibitor" is defined as a compound that binds to and/or inhibits the target bromodomain-containing protein (such as a BET protein, e.g., BRD2, BRD3, BRD4, and/or BRDT) with measurable affinity. In certain embodiments, an inhibitor has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

3. Description of Exemplary Compounds

In certain embodiments, the present invention provides a compound of formula I,

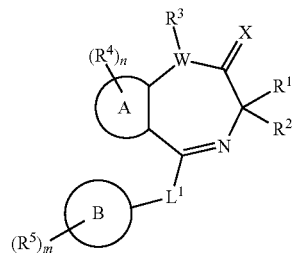

I or a pharmaceutically acceptable salt thereof, wherein each of $R^1$, $R^2$, $R^3$, $R^4$, $R^5$, n, m, W, $L^1$, X, Ring A, and Ring B is as defined and described herein.

As defined generally above, Ring A of formula I is benzo, or a 5-6 membered fused heteroaryl ring having 1-3 heteroatoms independently selected from nitrogen, oxygen, or sulfur. In some embodiments, Ring A is benzo. In other embodiments, Ring A is a 5-6 membered fused heteroaryl ring having 1-3 heteroatoms independently selected from nitrogen, oxygen, or sulfur.

In certain embodiments, Ring A is a 6-membered fused heteroaryl ring having 1-3 nitrogen atoms. Exemplary Ring A groups include pyrido, pyrimidino, pyrazino, pyridazino, and triazino, rings.

In some embodiments, Ring A is a 5-membered fused heteroaryl ring having 1 heteroatom selected from nitrogen, oxygen, or sulfur. In certain embodiments, Ring A is thieno. In other embodiments, Ring A is furano. In some embodiments, Ring A is pyrrolo.

In other embodiments, Ring A is a 5-membered fused heteroaryl ring having 2 heteroatoms independently selected from nitrogen, oxygen, or sulfur. In some embodiments, Ring A is a 5-membered fused heteroaryl ring having 2 heteroatoms independently selected from nitrogen or oxygen. In some embodiments, Ring A is a 5-membered fused heteroaryl ring having 2 heteroatoms selected from nitrogen and oxygen. In some embodiments, Ring A is a 5-membered fused heteroaryl ring having 2 heteroatoms independently selected from nitrogen or sulfur. In some embodiments, Ring A is a 5-membered fused heteroaryl ring having 2 heteroatoms selected from nitrogen and sulfur. Exemplary Ring A groups include thiazolo, isothiazolo, oxazolo, isoxazolo, pyrazolo, and imidazolo rings.

In some embodiments, the present invention provides a compound of formula I wherein one or more of the following apply:

(a) when Ring A is thieno, $L^1$ is a covalent bond, W is

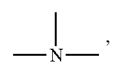

and Ring B is phenyl, $R^4$ is other than an amide-containing moiety in the 2-position of the thieno ring when hydrogen is present in the 3-position of the thieno ring;

(b) when Ring A is benzo, thieno, or pyrido, $L^1$ is a covalent bond, W is

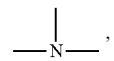

Ring B is aryl or heteroaryl, and $R^2$ is $C_{1-6}$ alkyl, then $R^1$ is other than —$CO_2R$ or —$(CH_2)_pR^x$ wherein $R^x$ is —$CO_2R$;

(c) when Ring A is benzo and W is

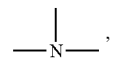

$R^1$ is other than —$(CH_2)_pR^x$ wherein $R^x$ comprises phenyl or naphthyl;

(d) when Ring A is thieno, L¹ is a covalent bond, W is

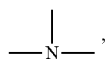

Ring B is phenyl, and at least one of R¹ and R² is methyl, then n is 1-2;
(e) when Ring A is benzo, thieno, or pyrido, L¹ is a covalent bond, W is

Ring B is aryl or heteroaryl, then R¹ and R² are not taken together to form an optionally substituted dihydropyrimidinedione or imidazolidinedione;
(f) when Ring A is thieno, L¹ is a covalent bond, W is

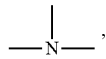

Ring B is pyridyl or thienyl wherein Ring B is optionally substituted with $C_{1-4}$ alkyl or halogen, and R² is methyl, R¹ is other than methyl, trifluoromethyl, cyclopropyl, or hydroxymethyl.

As defined generally above, Ring B of formula I is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur.

In some embodiments, Ring B is phenyl.

In some embodiments, Ring B is a 3-7 membered saturated or partially unsaturated carbocyclic ring. In certain embodiments, Ring B is cyclopropyl, cyclobutyl, cyclopentyl, cyclohexyl, or cycloheptyl. In certain embodiments, Ring B is cyclopentenyl, cyclohexenyl, or cycloheptenyl.

In some embodiments, Ring B is a 4-7 membered saturated or partially unsaturated heterocyclic ring having 1-2 heteroatoms independently selected from nitrogen, oxygen, and sulfur. In certain embodiments, Ring B is a 5-6 membered saturated or partially unsaturated heterocyclic ring having 1-2 heteroatoms independently selected from nitrogen, oxygen, and sulfur. In certain embodiments, Ring B is tetrahydrofuranyl, tetrahydrothienyl, tetrahydropyranyl, tetrahydrothiopyranyl, pyrrolidinyl, pyrrolidonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, Ring B is a 5-6 membered monocyclic heteroaryl ring having 1-3 heteroatoms independently selected from nitrogen, oxygen, and sulfur. In certain embodiments, Ring B is 6-membered heteroaryl ring having 1-3 nitrogen atoms. In other embodiments, Ring B is a 6-membered heteroaryl ring having 1 nitrogen atom. In certain other embodiments, Ring B is a 6-membered heteroaryl ring having 2 nitrogen atoms. In yet other embodiments, Ring B is a 6-membered heteroaryl ring having 3 nitrogen atoms.

In other embodiments, Ring B is a 5-membered heteroaryl ring having 1-3 heteroatoms independently selected from nitrogen, oxygen, or sulfur. In certain embodiments, Ring B is a 5-membered heteroaryl ring having 1 heteroatom independently selected from nitrogen, oxygen, or sulfur. In certain embodiments, Ring B is a 5-membered heteroaryl ring having 2 heteroatoms independently selected from nitrogen, oxygen, or sulfur. In other embodiments, Ring B is a 5-membered heteroaryl ring having 2 heteroatoms independently selected from nitrogen and oxygen. In some embodiments, Ring B is a 5-membered heteroaryl ring having 2 heteroatoms independently selected from nitrogen and sulfur. In other embodiments, Ring B is a 5-membered heteroaryl ring having 1-3 nitrogen atoms. In certain embodiments, Ring B is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, Ring B is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In certain embodiments, Ring B is a 5,5-fused-, 5,6-fused, or 6,6-fused saturated, partially unsaturated, or aromatic bicyclic ring. In some embodiments, Ring B is a 5,5-fused, 5,6-fused, or 6,6-fused aromatic bicyclic ring. In other embodiments, Ring B is a naphthalenyl, indanyl or indenyl group.

In some embodiments, Ring B is a 7-10 membered bicyclic saturated or partially unsaturated heterocyclic ring having 1-4 heteroatoms independently selected from nitrogen, oxygen, and sulfur. In certain embodiments, Ring B is a 7-8 membered bicyclic saturated heterocyclic ring having 1-3 heteroatoms independently selected from nitrogen, oxygen, and sulfur. In certain embodiments, Ring B is a 7-8 membered bicyclic partially unsaturated heterocyclic ring having 1-3 heteroatoms independently selected from nitrogen, oxygen, and sulfur. In certain embodiments, Ring B is a 9-10 membered bicyclic saturated heterocyclic ring having 1-3 heteroatoms independently selected from nitrogen, oxygen, and sulfur. In certain embodiments, Ring B is a 9-10 membered bicyclic partially unsaturated heterocyclic ring having 1-3 heteroatoms independently selected from nitrogen, oxygen, and sulfur. In certain embodiments, Ring B is tetrahydroquinolinyl, tetrahydroisoquinolinyl, decahydroquinolinyl, or quinuclidinyl. In certain embodiments, Ring B is indolinyl, 3H-indolyl, chromanyl, phenanthridinyl, 2-azabicyclo[2.2.1]heptanyl, octahydroindolyl, or tetrahydroquinolinyl.

In some embodiments, Ring B is a 8-10 membered bicyclic heteroaryl ring having 1-4 heteroatoms independently selected from nitrogen, oxygen, and sulfur. In some embodiments, Ring B is a 5,5-fused, 5,6-fused, or 6,6-fused saturated, partially unsaturated, or aromatic bicyclic ring having 1-4 heteroatoms, independently selected from nitrogen, oxygen, or sulfur. In other embodiments, Ring B is a 5,5-fused, 5,6-fused, or 6,6-fused heteroaryl ring having 1-4 heteroatoms, independently selected from nitrogen, oxygen, or sulfur. In certain aspects, Ring B is a 5,5-fused, 5,6-fused, or 6,6-fused heteroaryl ring having 1-4 nitrogen atoms. In other embodiments, Ring B is a 5,6-fused heteroaryl ring having 1-4 nitrogen atoms. In certain embodiments, Ring B is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphtheneyl, or benzofuranyl. In certain embodiments, Ring B is a indolizinyl, purinyl, naphthyridinyl, or pteridinyl.

As defined generally above, m and n of formula I are each independently 0-4. In some embodiments, m is 0. In other embodiments, m is 1-4. In certain embodiments, m is 1-2. In some embodiments, m is 1.

In some embodiments, n is 0. In other embodiments, n is 1-4. In certain embodiments, n is 1-2. In some embodiments, n is 1.

As defined generally above, $L^1$ of formula I is a covalent bond or a bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—.

In some embodiments, $L^1$ is a covalent bond. In other embodiments, $L^1$ is an optionally substituted bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In certain embodiments, $L^1$ is an optionally substituted bivalent $C_{1-3}$ hydrocarbon chain wherein one methylene unit is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In certain embodiments, $L^1$ is a $C_{1-3}$ hydrocarbon chain wherein one methylene unit is optionally replaced by —NH—, —O—, —S—, —S(O)—, or —SO$_2$—.

As generally defined above, $R^1$ of formula I is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$, or —(CH$_2$)$_p$R$^x$.

In certain embodiments, $R^1$ is optionally substituted $C_{1-6}$ aliphatic, —OR, —N(R')$_2$, —C(O)R, —OC(O)R, —N(R')C(O)R, —C(O)NR', or —CO$_2$R.

As defined generally above, p of formula I is 0-3. In some embodiments, p is 1-3. In other embodiments p is 1-2. In some embodiments, p is 1. In other embodiments, p is 2.

As defined generally above, R' of formula I is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$. In certain embodiments, R' is optionally substituted $C_{1-6}$ aliphatic, —OR, —N(R')$_2$, —C(O)R, —OC(O)R, —N(R')C(O)R, —C(O)NR', or —CO$_2$R. In some embodiments, p is 1 and R' is optionally substituted $C_{1-6}$ aliphatic, —OR, —N(R')$_2$, —C(O)R, —OC(O)R, —N(R')C(O)R, —C(O)NR', or —CO$_2$R.

As defined generally above, $R^2$ of formula I is halogen, —CN, —SR, or optionally substituted $C_{1-6}$ aliphatic, or $R^1$ and $R^2$ are taken together with their intervening atoms to form an optionally substituted 3-7 membered saturated or partially unsaturated spiro-fused ring having 0-2 heteroatoms independently selected from nitrogen, oxygen, or sulfur.

In some embodiments, $R^2$ is halogen. In other embodiments, $R^2$ is optionally substituted $C_{1-6}$ aliphatic. In certain embodiments, $R^2$ is $C_{1-4}$ alkyl. In some embodiments, $R^2$ is methyl. In some embodiments, $R^2$ is —CN. In some embodiments, $R^2$ is —S—$C_{1-6}$ alkyl.

In certain embodiments, $R^1$ and $R^2$ of formula I are taken together with their intervening atoms to form an optionally substituted 3-7 membered saturated or partially unsaturated spiro-fused ring having 0-2 heteroatoms independently selected from nitrogen, oxygen, or sulfur. In some embodiments, $R^1$ and $R^2$ are taken together with their intervening atoms to form an optionally substituted 5-6 membered saturated spiro-fused ring having 0-2 heteroatoms independently selected from nitrogen, oxygen, or sulfur. In some embodiments, $R^1$ and $R^2$ are taken together with their intervening atoms to form an optionally substituted 5-6 membered saturated spiro-fused ring having 1-2 heteroatoms independently selected from nitrogen, oxygen, or sulfur.

In some embodiments, $R^1$ and $R^2$ are taken together with their intervening atoms to form a spiro-fused cyclopropyl, cyclobutyl, cyclopentyl, or cyclohexyl ring. Exemplary spiro-rings formed by $R^1$ and $R^2$ include cyclopropyl, cyclobutyl, cyclopentyl, cyclohexyl or pyrrolidinone. In some embodiments, $R^1$ and $R^2$ form an optionally substituted spiro-fused cyclopropyl ring.

In some embodiments, $R^1$ and $R^2$ are taken together with their intervening atoms to form a spiro-fused oxiranyl, oxetanyl, tetrahydrofuranyl or tetrahydro-2H-pyranyl ring. In some embodiments, $R^1$ and $R^2$ are taken together with their intervening atoms to form a spiro-fused aziridinyl, azetidinyl, pyrrolidinyl or piperidinyl ring.

As defined generally above, W of formula I is

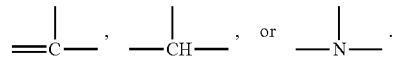

In certain embodiments, W is

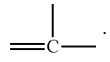

In certain embodiments, W is

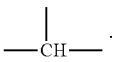

In certain embodiments, W is

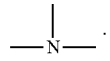

As defined generally above, $R^3$ of formula I is optionally substituted $C_{1-6}$ aliphatic. In some embodiments, $R^3$ is substituted. In some embodiments, $R^3$ is unsubstituted. In certain embodiments, $R^3$ is $C_{1-6}$ alkyl. In certain embodiments, $R^3$ is $C_{1-4}$ alkyl. In certain embodiments, $R^3$ is methyl, ethyl, propyl, or isopropyl.

As defined generally above, X of formula I is oxygen or sulfur, or $R^3$ and X are taken together with their intervening atoms to form an optionally substituted 5-membered heteroaryl ring having 1-4 heteroatoms independently selected from nitrogen, oxygen, or sulfur. In some embodiments, X is oxygen. In some embodiments, X is sulfur. In some embodiments, $R^3$ and X are taken together with their intervening atoms to form an optionally substituted 5-membered heteroaryl ring having 1-4 heteroatoms independently selected from nitrogen, oxygen, or sulfur. In some embodiments, $R^3$ and X are taken together with their intervening atoms to form a substituted 5-membered heteroaryl ring having 1-4 heteroatoms independently selected from nitrogen, oxygen, or sulfur. In some embodiments, $R^3$ and X are taken together with their intervening atoms to form an unsubstituted 5-membered heteroaryl ring having 1-4 heteroatoms independently selected from nitrogen, oxygen, or sulfur. In certain embodiments, $R^3$ and X are taken together with their intervening atoms to form an optionally substituted 5-membered heteroaryl ring having 1-2 heteroatoms independently selected from nitrogen, oxygen, or sulfur. In certain embodiments, $R^3$ and X are taken together with their intervening atoms to form an optionally substituted pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl ring.

As defined generally above, $R^4$ of formula I is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$, wherein R and R' are as defined and described herein. In some embodiments, $R^4$ is —R. In certain embodiments, $R^4$ is hydrogen. In certain other embodiments, $R^4$ is halogen. In some embodiments, $R^4$ is —OR, —SR, or —N(R')$_2$. In certain embodiments, $R^4$ is —OR. In other embodiments, $R^4$ is —CN or —NO$_2$. In some embodiments, $R^4$ is —C(O)R, —CO$_2$R, —C(O)N(R')$_2$, —C(O)SR, —C(O)C(O)R, —C(O)CH$_2$C(O)R, —C(S)N(R')$_2$, or —C(S)OR. In other embodiments, $R^4$ is —S(O)R, —SO$_2$R, or —SO$_2$N(R')$_2$. In certain embodiments, $R^4$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain other embodiments, $R^4$ is —C=NN(R')$_2$, —C=NOR, —C(=N(R'))N(R')$_2$. In yet other embodiments, $R^4$ is —OC(O)R or —OC(O)N(R')$_2$.

As defined generally above, $R^5$ of formula I is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$, wherein R and R' are as defined and described herein. In some embodiments, $R^5$ is —R. In certain embodiments, $R^5$ is hydrogen. In certain other embodiments, $R^5$ is halogen. In some embodiments, $R^5$ is —OR, —SR, or —N(R')$_2$. In certain embodiments, $R^5$ is —OR. In other embodiments, $R^5$ is —CN or —NO$_2$. In some embodiments, $R^5$ is —C(O)R, —CO$_2$R, —C(O)N(R')$_2$, —C(O)SR, —C(O)C(O)R, —C(O)CH$_2$C(O)R, —C(S)N(R')$_2$, or —C(S)OR. In other embodiments, $R^5$ is —S(O)R, —SO$_2$R, or —SO$_2$N(R')$_2$. In certain embodiments, $R^5$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain other embodiments, $R^5$ is —C=NN(R')$_2$, —C=NOR, —C(=N(R'))N(R')$_2$. In yet other embodiments, $R^5$ is —OC(O)R or —OC(O)N(R')$_2$.

In certain embodiments, the present invention provides a compound of formula II,

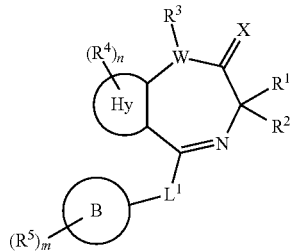

II or a pharmaceutically acceptable salt thereof, wherein each of $R^1$, $R^2$, $R^3$, $R^4$, $R^5$, n, m, $L^1$, X, W, Hy, and Ring B is as defined and described herein.

As defined generally above, Hy of formula II is a 5-membered fused heteroaryl ring having 2-3 heteroatoms independently selected from nitrogen, oxygen, or sulfur, or a 6-membered fused heteroaryl ring having 2-3 nitrogen atoms. In some embodiments, Hy of formula II is a 5-membered fused heteroaryl ring having 2-3 heteroatoms independently selected from nitrogen, oxygen, or sulfur, a 6-membered fused heteroaryl ring having 2-3 nitrogen atoms. In certain embodiments, Hy is a 6-membered fused heteroaryl ring having 2 nitrogen atoms. In certain embodiments, Hy is a 6-membered fused heteroaryl ring having 3 nitrogen atoms. Exemplary Hy groups include pyrimidino, pyrazino, pyridazino, and triazino rings.

In other embodiments, Hy is a 5-membered fused heteroaryl ring having 2 heteroatoms independently selected from nitrogen, oxygen, or sulfur. In some embodiments, Hy is a 5-membered fused heteroaryl ring having 2 heteroatoms independently selected from nitrogen or oxygen. In some embodiments, Hy is a 5-membered fused heteroaryl ring having 2 heteroatoms selected from nitrogen and oxygen. In some embodiments, Hy is a 5-membered fused heteroaryl ring having 2 heteroatoms independently selected from nitrogen or sulfur. In some embodiments, Hy is a 5-membered fused heteroaryl ring having 2 heteroatoms selected from nitrogen and sulfur. Exemplary Hy groups include thiazolo, oxazolo, isoxazolo, pyrazolo, and imidazolo rings.

In other embodiments, Hy is a 5-membered fused heteroaryl ring having 3 heteroatoms independently selected from nitrogen, oxygen, or sulfur. In some embodiments, Hy is a 5-membered fused heteroaryl ring having 3 heteroatoms independently selected from nitrogen and oxygen. In some embodiments, Hy is a 5-membered fused heteroaryl ring having 3 heteroatoms independently selected from nitrogen and sulfur. Exemplary Hy groups include triazolo, thiadiazolo, and oxadiazolo rings.

As defined generally above, Ring B of formula II is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur.

In some embodiments, Ring B is phenyl.

In some embodiments, Ring B is a 3-7 membered saturated or partially unsaturated carbocyclic ring. In certain embodiments, Ring B is cyclopropyl, cyclobutyl, cyclopentyl, cyclohexyl, or cycloheptyl. In certain embodiments, Ring B is cyclopentenyl, cyclohexenyl, or cycloheptenyl.

In some embodiments, Ring B is a 4-7 membered saturated or partially unsaturated heterocyclic ring having 1-2 heteroatoms independently selected from nitrogen, oxygen, and sulfur. In certain embodiments, Ring B is a 5-6 membered saturated or partially unsaturated heterocyclic ring having 1-2 heteroatoms independently selected from nitrogen, oxygen, and sulfur. In certain embodiments, Ring B is tetrahydrofuranyl, tetrahydrothienyl, tetrahydropyranyl, tetrahydrothiopyranyl, pyrrolidinyl, pyrrolidonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, Ring B is a 5-6 membered monocyclic heteroaryl ring having 1-3 heteroatoms independently selected from nitrogen, oxygen, and sulfur. In certain embodiments, Ring B is 6-membered heteroaryl ring having 1-3 nitrogen atoms. In other embodiments, Ring B is a 6-membered heteroaryl ring having 1 nitrogen atom. In certain other embodiments, Ring B is a 6-membered heteroaryl ring having 2 nitrogen atoms. In yet other embodiments, Ring B is a 6-membered heteroaryl ring having 3 nitrogen atoms.

In other embodiments, Ring B is a 5-membered heteroaryl ring having 1-3 heteroatoms independently selected from nitrogen, oxygen, or sulfur. In certain embodiments, Ring B is a 5-membered heteroaryl ring having 1 heteroatom independently selected from nitrogen, oxygen, or sulfur. In certain embodiments, Ring B is a 5-membered heteroaryl ring having 2 heteroatoms independently selected from nitrogen, oxygen, or sulfur. In other embodiments, Ring B is a 5-membered heteroaryl ring having 2 heteroatoms independently selected from nitrogen and oxygen. In some embodiments, Ring B is a 5-membered heteroaryl ring having 2 heteroatoms independently selected from nitrogen and sulfur. In other embodiments, Ring B is a 5-membered heteroaryl ring having 1-3 nitrogen atoms. In certain embodiments, Ring B is thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, or pyrazinyl.

In some embodiments, Ring B is a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur. In certain embodiments, Ring B is a 5,5-fused-, 5,6-fused, or 6,6-fused saturated, partially unsaturated, or aromatic bicyclic ring. In some embodiments, Ring B is a 5,5-fused, 5,6-fused, or 6,6-fused aromatic bicyclic ring. In other embodiments, Ring B is a naphthalenyl, indanyl or indenyl group.

In some embodiments, Ring B is a 7-10 membered bicyclic saturated or partially unsaturated heterocyclic ring having 1-4 heteroatoms independently selected from nitrogen, oxygen, and sulfur. In certain embodiments, Ring B is a 7-8 membered bicyclic saturated heterocyclic ring having 1-3 heteroatoms independently selected from nitrogen, oxygen, and sulfur. In certain embodiments, Ring B is a 7-8 membered bicyclic partially unsaturated heterocyclic ring having 1-3 heteroatoms independently selected from nitrogen, oxygen, and sulfur. In certain embodiments, Ring B is a 9-10 membered bicyclic saturated heterocyclic ring having 1-3 heteroatoms independently selected from nitrogen, oxygen, and sulfur. In certain embodiments, Ring B is a 9-10 membered bicyclic partially unsaturated heterocyclic ring having 1-3 heteroatoms independently selected from nitrogen, oxygen, and sulfur. In certain embodiments, Ring B is tetrahydroquinolinyl, tetrahydroisoquinolinyl, decahydroquinolinyl, or quinuclidinyl. In certain embodiments, Ring B is indolinyl, 3H-indolyl, chromanyl, phenanthridinyl, 2-azabicyclo[2.2.1]heptanyl, octahydroindolyl, or tetrahydroquinolinyl.

In some embodiments, Ring B is a 8-10 membered bicyclic heteroaryl ring having 1-4 heteroatoms independently selected from nitrogen, oxygen, and sulfur. In some embodiments, Ring B is a 5,5-fused, 5,6-fused, or 6,6-fused saturated, partially unsaturated, or aromatic bicyclic ring having 1-4 heteroatoms, independently selected from nitrogen, oxygen, or sulfur. In other embodiments, Ring B is a 5,5-fused, 5,6-fused, or 6,6-fused heteroaryl ring having 1-4 heteroatoms, independently selected from nitrogen, oxygen, or sulfur. In certain aspects, Ring B is a 5,5-fused, 5,6-fused, or 6,6-fused heteroaryl ring having 1-4 nitrogen atoms. In other embodiments, Ring B is a 5,6-fused heteroaryl ring having 1-4 nitrogen atoms. In certain embodiments, Ring B is pyrrolizinyl, indolyl, quinolinyl, isoquinolinyl, benzimidazolyl, imidazopyridinyl, indazolyl, purinyl, cinnolinyl, quinazolinyl, phthalazinyl, naphthridinyl, quinoxalinyl, thianaphtheneyl, or benzofuranyl. In certain embodiments, Ring B is a indolizinyl, purinyl, naphthyridinyl, or pteridinyl.

As defined generally above, m and n of formula II are each independently 0-4. In some embodiments, m is 0. In other embodiments, m is 1-4. In certain embodiments, m is 1-2. In some embodiments, m is 1.

In some embodiments, n is 0. In other embodiments, n is 1-4. In certain embodiments, n is 1-2. In some embodiments, n is 1.

As defined generally above, $L^1$ of formula II is a covalent bond or a bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—.

In some embodiments, $L^1$ is a covalent bond. In other embodiments, $L^1$ is an optionally substituted bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In certain embodiments, $L^1$ is an optionally substituted bivalent $C_{1-3}$ hydrocarbon chain wherein one methylene unit is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—. In certain embodiments, $L^1$ is a $C_{1-3}$ hydrocarbon chain wherein one methylene unit is optionally replaced by —NH—, —O—, —S—, —S(O)—, or —SO$_2$—.

As generally defined above, $R^1$ of formula II is hydrogen, halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$, or —(CH$_2$)$_p$R$^x$.

In certain embodiments, $R^1$ is optionally substituted $C_{1-6}$ aliphatic, —OR, —N(R')$_2$, —C(O)R, —OC(O)R, —N(R')C(O)R, —C(O)NR', or —CO$_2$R.

As defined generally above, p of formula II is 0-3. In some embodiments, p is 1-3. In other embodiments p is 1-2. In some embodiments, p is 1. In other embodiments, p is 2.

As defined generally above, $R^x$ of formula II is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$. In certain embodiments, $R^x$ is optionally substituted $C_{1-6}$ aliphatic, —OR, —N(R')$_2$, —C(O)R, —OC(O)R, —N(R')C(O)R, —C(O)NR', or —CO$_2$R. In some embodiments, p is 1 and $R^x$ is optionally substituted $C_{1-6}$ aliphatic, —OR, —N(R')$_2$, —C(O)R, —OC(O)R, —N(R')C(O)R, —C(O)NR', or —CO$_2$R.

As defined generally above, $R^2$ of formula II is hydrogen, halogen, —CN, —SR, or optionally substituted $C_{1-6}$ aliphatic, or $R^1$ and $R^2$ are taken together with their intervening atoms to form an optionally substituted 3-7 membered saturated or partially unsaturated spiro-fused ring having 0-2 heteroatoms independently selected from nitrogen, oxygen, or sulfur.

In some embodiments, $R^2$ is hydrogen. In some embodiments, $R^2$ is halogen. In other embodiments, $R^2$ is optionally substituted $C_{1-6}$ aliphatic. In certain embodiments, $R^2$ is $C_{1-4}$ alkyl. In some embodiments, $R^2$ is methyl. In some embodiments, $R^2$ is —CN. In some embodiments, $R^2$ is —S—$C_{1-6}$ alkyl.

In certain embodiments, $R^1$ and $R^2$ of formula II are taken together with their intervening atoms to form an optionally substituted 3-7 membered saturated or partially unsaturated spiro-fused ring having 0-2 heteroatoms independently selected from nitrogen, oxygen, or sulfur. In some embodiments, $R^1$ and $R^2$ are taken together with their intervening atoms to form an optionally substituted 5-6 membered saturated spiro-fused ring having 0-2 heteroatoms independently selected from nitrogen, oxygen, or sulfur. In some embodiments, $R^1$ and $R^2$ are taken together with their intervening atoms to form an optionally substituted 5-6 membered saturated spiro-fused ring having 1-2 heteroatoms independently selected from nitrogen, oxygen, or sulfur.

In some embodiments, $R^1$ and $R^2$ are taken together with their intervening atoms to form a spiro-fused cyclopropyl, cyclobutyl, cyclopentyl, or cyclohexyl ring. Exemplary spiro-rings formed by $R^1$ and $R^2$ include cyclopropyl, cyclobutyl, cyclopentyl, cyclohexyl or pyrrolidinone. In some embodiments, $R^1$ and $R^2$ form an optionally substituted spiro-fused cyclopropyl ring.

As defined generally above, $R^3$ of formula II is optionally substituted $C_{1-6}$ aliphatic. In some embodiments, $R^3$ is substituted. In some embodiments, $R^3$ is unsubstituted. In certain embodiments, $R^3$ is $C_{1-6}$ alkyl. In certain embodiments, $R^3$ is $C_{1-4}$ alkyl. In certain embodiments, $R^3$ is methyl, ethyl, propyl, or isopropyl.

As defined generally above, X of formula II is oxygen or sulfur, or $R^3$ and X are taken together with their intervening atoms to form an optionally substituted 5-membered heteroaryl ring having 1-4 heteroatoms independently selected from nitrogen, oxygen, or sulfur. In some embodiments, X is oxygen. In some embodiments, X is sulfur. In some embodiments, $R^3$ and X are taken together with their intervening atoms to form an optionally substituted 5-membered heteroaryl ring having 1-4 heteroatoms independently selected from nitrogen, oxygen, or sulfur. In some embodiments, $R^3$ and X are taken together with their intervening atoms to form a substituted 5-membered heteroaryl ring having 1-4 heteroatoms independently selected from nitrogen, oxygen, or sulfur. In some embodiments, $R^3$ and X are taken together with their intervening atoms to form an unsubstituted 5-membered heteroaryl ring having 1-4 heteroatoms independently selected from nitrogen, oxygen, or sulfur. In certain embodiments, $R^3$ and X are taken together with their intervening atoms to form an optionally substituted 5-membered heteroaryl ring having 1-2 heteroatoms independently selected from nitrogen, oxygen, or sulfur. In certain embodiments, $R^3$ and X are taken together with their intervening atoms to form an optionally substituted pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl ring.

As defined generally above, $R^4$ of formula II is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$, wherein R and R' are as defined and described herein. In some embodiments, $R^4$ is —R. In certain embodiments, $R^4$ is hydrogen. In certain other embodiments, $R^4$ is halogen. In some embodiments, $R^4$ is —OR, —SR, or —N(R')$_2$. In certain embodiments, $R^4$ is —OR. In other embodiments, $R^4$ is —CN or —NO$_2$. In some embodiments, $R^4$ is —C(O)R, —CO$_2$R, —C(O)N(R')$_2$, —C(O)SR, —C(O)C(O)R, C(O)CH$_2$C(O)R, —C(S)N(R')$_2$, or —C(S)OR. In other embodiments, $R^4$ is —S(O)R, —SO$_2$R, or —SO$_2$N(R')$_2$. In certain embodiments, $R^4$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain other embodiments, $R^4$ is —C=NN(R')$_2$, —C=NOR, —C(=N(R'))N(R')$_2$. In yet other embodiments, $R^4$ is —OC(O)R or —OC(O)N(R')$_2$.

As defined generally above, $R^5$ of formula II is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$, wherein R and R' are as defined and described herein. In some embodiments, $R^5$ is —R. In certain embodiments, $R^5$ is hydrogen. In certain other embodiments, $R^5$ is halogen. In some embodiments, $R^5$ is —OR, —SR, or —N(R')$_2$. In certain embodiments, $R^5$ is —OR. In other embodiments, $R^5$ is —CN or —NO$_2$. In some embodiments, $R^5$ is —C(O)R, —CO$_2$R, —C(O)N(R')$_2$, —C(O)SR, —C(O)C(O)R, —C(O)CH$_2$C(O)R, —C(S)N(R')$_2$, or —C(S)OR. In other embodiments, $R^5$ is —S(O)R, —SO$_2$R, or —SO$_2$N(R')$_2$. In certain embodiments, $R^5$ is —N(R')C(O)R, —N(R')C(O)N(R')$_2$, —N(R')SO$_2$R, —N(R')SO$_2$N(R')$_2$, —N(R')N(R')$_2$, or —N(R')C(=N(R'))N(R')$_2$. In certain other embodiments, $R^5$ is —C=NN(R')$_2$, —C=NOR, —C(=N(R'))N(R')$_2$. In yet other embodiments, $R^5$ is —OC(O)R or —OC(O)N(R')$_2$.

As defined generally above, W of formula II is

In certain embodiments, W is

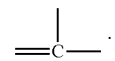

In certain embodiments, W is

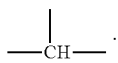

In certain embodiments, W is

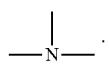

In certain embodiments, at least one of $R^1$ and $R^2$ of formula II is hydrogen.

As defined generally above, each R is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated, or aryl ring, a 5-6 membered monocyclic heteroaryl ring having 1-3 heteroatoms independently selected from nitrogen, oxygen, or sulfur, a 4-7 membered saturated or partially unsaturated heterocyclic ring having 1-2 heteroatoms independently selected from nitrogen, oxygen, or sulfur, a 7-10 membered bicyclic saturated or partially unsaturated heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur. In certain embodiments, R is hydrogen. In some embodiments, R is optionally substituted $C_{1-6}$ alkyl, alkenyl, or alkynyl. In certain embodiments, R is optionally substituted $C_{1-6}$ alkyl. In certain embodiments, R is unsubstituted $C_{1-6}$ alkyl. In certain embodiments, R is substituted $C_{1-6}$ alkyl. In certain embodiments, R is methyl, ethyl, propyl, butyl, isopropyl, isobutyl, allyl, or benzyl.

In some embodiments, R is a 3-7 membered saturated or partially unsaturated carbocyclic ring. In certain embodiments, R is a 3-4 membered saturated carbocyclic ring. In other embodiments, R is a 5-7 membered saturated or partially unsaturated carbocyclic ring. In certain embodiments, R is cyclopropyl, cyclobutyl, cyclopentyl, cyclopentenyl, cyclohexyl, cyclohexenyl, cycloheptyl, or cycloheptenyl.

In some embodiments, R is a 4-7 membered saturated or partially unsaturated heterocyclic ring having 1-2 heteroatoms independently selected from nitrogen, oxygen, or sulfur. In certain embodiments, R is a 4-7 membered saturated heterocyclic ring. In other embodiments, R is a 5-7 membered partially unsaturated heterocyclic ring. In certain embodiments, R is tetrahydrofuranyl, tetrahydrothienyl, tetrahydropyranyl, tetrahydrothiopyranyl, pyrrolidinyl, pyrrolidonyl, piperidinyl, pyrrolinyl, oxazolidinyl, piperazinyl, dioxanyl, dioxolanyl, diazepinyl, oxazepinyl, thiazepinyl, or morpholinyl.

In some embodiments, R is an 8-10 membered bicyclic saturated or partially unsaturated carbocyclic ring or a 7-10 membered bicyclic saturated or partially unsaturated heterocyclic ring having 1-4 heteroatoms independently selected from nitrogen, oxygen, or sulfur. In certain embodiments, R is decahydronaphthyl, tetrahydronaphthyl, or decalin. In certain other embodiments, R is tetrahydroquinolinyl, tetrahydroisoquinolinyl, or decahydroquinolinyl. In some embodiments, R is a heterocyclyl ring is fused to an aryl or heteroaryl ring. In certain embodiments, R is indolinyl, 3H-indolyl, chromanyl, phenanthridinyl, 2-azabicyclo[2.2.1]heptanyl, octahydroindolyl, or tetrahydroquinolinyl.

In some embodiments, R is phenyl or a 5-6 membered heteroaryl ring having 1-3 heteroatoms independently selected from nitrogen, oxygen, or sulfur. In certain embodiments, R is phenyl. In certain other embodiments, R is a 5-membered heteroaryl ring having 1-3 heteroatoms selected from nitrogen, oxygen, or sulfur. In yet other embodiments, R is a 6-membered heteroaryl ring having 1-3 nitrogens. In certain embodiments, R is phenyl, pyridyl, pyrimidyl, pyrazinyl, pyridazinyl, or triazinyl. In certain other embodiments, R is pyrrolyl, pyrazolyl, imidazolyl, triazolyl, tetrazolyl, thienyl, furanyl, thiazolyl, isothiazolyl, thiadiazolyl, oxazolyl, isoxazolyl, or oxadiazolyl.

In some embodiments, R is bicyclic aromatic ring. In certain embodiments, R is naphthyl. In other embodiments, R is an 8-10 membered bicyclic heteroaryl ring having 1-4 heteroatoms independently selected from nitrogen, oxygen, or sulfur. In certain embodiments, R is quinolinyl, quinoxalinyl, quinazolinyl, pyridopyrazinyl, or pyridopyrimidyl. In certain other embodiments, R is indolyl, benzimidazolyl, benzothiazolyl, benzofuranyl, benzotriazolyl, benzoxazolyl, benzothiophenyl, indazolyl, imidazopyridyl, imidazopyrimidyl, imidazopyrazinyl, imidazopyridazinyl, pyrazolopyridyl, pyrazolopyrimidyl, pyrazolopyrazinyl, pyrazolopyridazinyl, pyrrolothiazolyl, imidazothiazolyl, thiazolopyridyl, thiazolopyrimidyl, thiazolopypyrazinyl, thiazolopyridazinyl, oxazolopyridyl, oxazolopyrimidyl, oxazolopyrazinyl, or oxazolopyridazinyl.

As defined generally above, each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R' on the same nitrogen are taken together with their intervening atoms to form an optionally substituted group selected from a 4-7 membered monocyclic saturated or partially unsaturated ring having 1-2 heteroatoms independently selected from nitrogen, oxygen, and sulfur, or a 7-12 membered bicyclic saturated, partially unsaturated, or aromatic fused ring having 1-3 heteroatoms independently selected from nitrogen, oxygen, and sulfur. In certain embodiments, R' is R as defined and described above. In certain embodiments, R' is —C(O)R, —CO$_2$R, or —C(O)N(R)$_2$. In certain embodiments, R' is —S(O)R, —SO$_2$R, or —SO$_2$N(R)$_2$. In some embodiments, two R' on the same nitrogen are taken together with their intervening atoms to form a 4-7 membered heterocyclic ring having 1-2 heteroatoms independently selected from nitrogen, oxygen, and sulfur. In certain embodiments, two R' on the same nitrogen are taken together with their intervening atoms to form an optionally substituted azetidine, pyrrolidine, piperidine, morpholine, piperazine, homopiperidine, or homopiperazine ring. In some embodiments, two R' on the same nitrogen are taken together with their intervening atoms to form a 7-12 membered bicyclic saturated, partially unsaturated, or aromatic fused ring having 1-3 heteroatoms independently selected from nitrogen, oxygen, and sulfur. In certain embodiments, two R' on the same nitrogen are taken together with their intervening atoms to form an optionally substituted tetrahydroquinoline, tetrahydroisoquinoline, decahydroquinoline, indoline, 3H-indole, chromane, phenanthridine, 2-azabicyclo[2.2.1]heptane, or octahydroindole ring.

In certain embodiments, a compound of formula I is of Formula I-a:

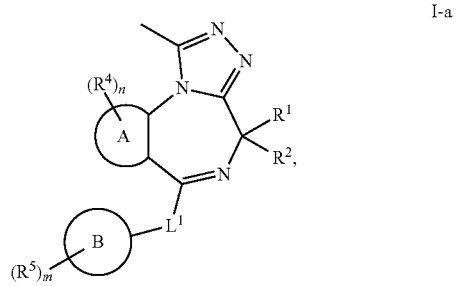

I-a or a pharmaceutically acceptable salt thereof, wherein $R^1$, $R^2$, $R^4$, $R^5$, $L^1$, m, n, Ring A and Ring B are as defined above and described in classes and subclasses herein.

In certain embodiments, a compound of formula I-a is of Formula I-a-i or I-a-ii:

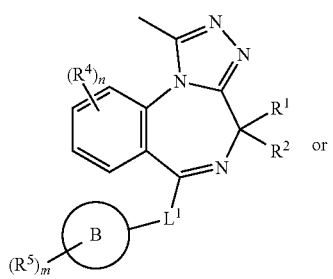

I-a-i

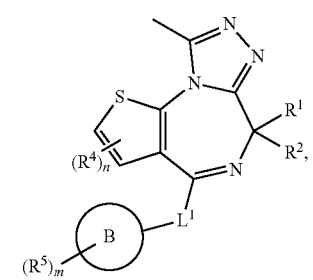

I-a-ii or a pharmaceutically acceptable salt thereof, wherein $R^1$, $R^2$, $R^4$, $R^5$, $L^1$, m, Ring B, and n are as defined above and described in classes and subclasses herein.

Exemplary compounds of the invention are set forth in Table 1 below.

TABLE 1

Exemplary Compounds.

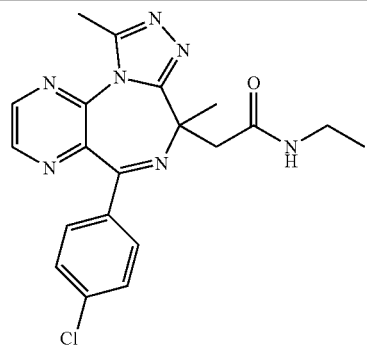

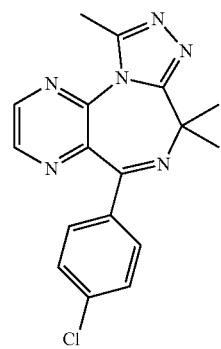 [SMILES: Cc1nnc2n1-c1nccnc1C(c1ccc(Cl)cc1)=NC2(C)C]

TABLE 1-continued

Exemplary Compounds.

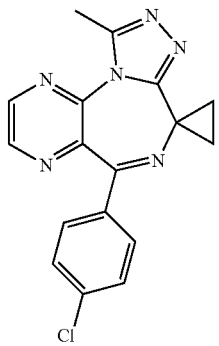 [SMILES: Cc1nnc2n1-c1nccnc1C(c1ccc(Cl)cc1)=NC21CC1]

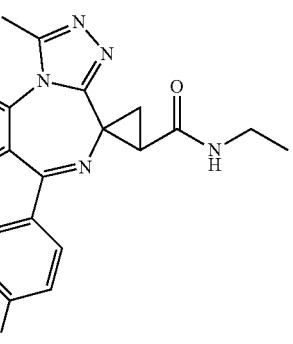

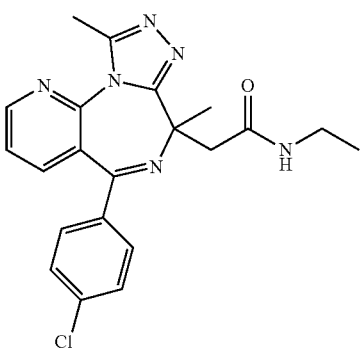 [SMILES: CCNC(=O)CC1(C)N=C(c2ccc(Cl)cc2)c2cccnc2-n2c(C)nnc21]

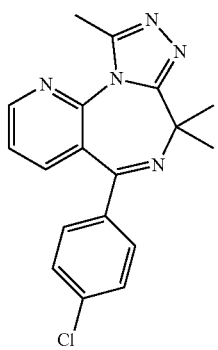 [SMILES: Cc1nnc2n1-c1ncccc1C(c1ccc(Cl)cc1)=NC2(C)C]

TABLE 1-continued
Exemplary Compounds.
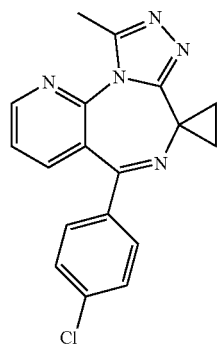 [SMILES: Cc1nnc2n1-c1ncccc1C(c1ccc(Cl)cc1)=NC21CC1]
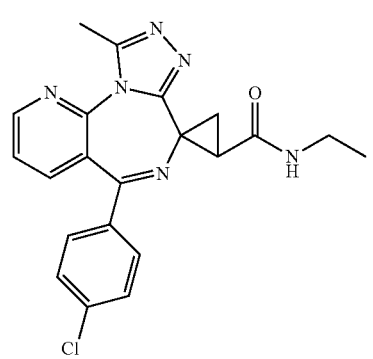 [SMILES: CCNC(=O)C1CC12N=C(c1ccc(Cl)cc1)c1cccnc1-n1c(C)nnc12]
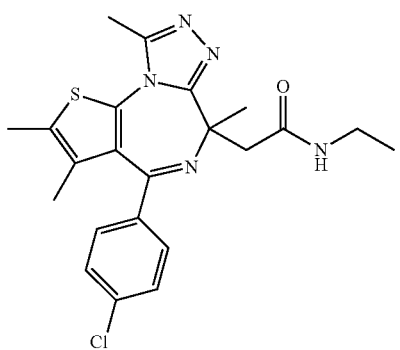 [SMILES: CCNC(=O)CC1(C)N=C(c2ccc(Cl)cc2)c2c(sc(C)c2C)-n2c(C)nnc21]
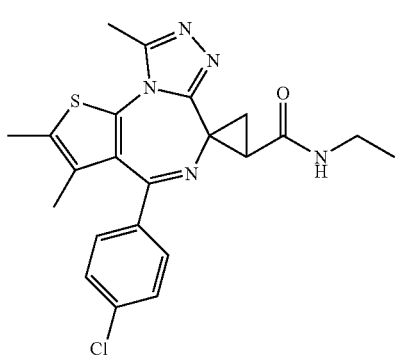 [SMILES: CCNC(=O)C1CC12N=C(c1ccc(Cl)cc1)c1c(sc(C)c1C)-n1c(C)nnc12]
TABLE 1-continued
Exemplary Compounds.
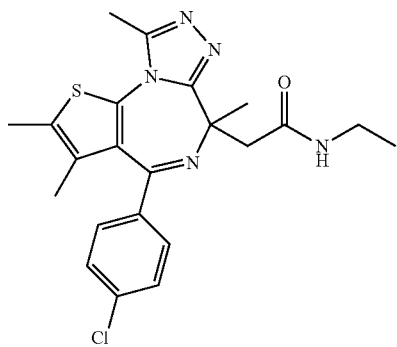 [SMILES: CCNC(=O)CC1(C)N=C(c2ccc(Cl)cc2)c2c(sc(C)c2C)-n2c(C)nnc21]
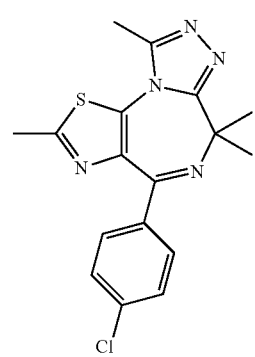
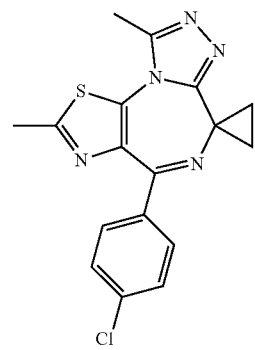 [SMILES: Cc1nc2c(s1)-n1c(C)nnc1C1(CC1)N=C2c1ccc(Cl)cc1]
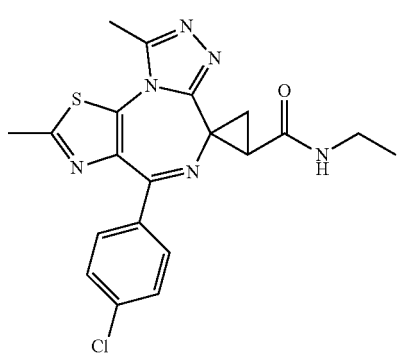 [SMILES: CCNC(=O)C1CC12N=C(c1ccc(Cl)cc1)c1nc(C)sc1-n1c(C)nnc12]

TABLE 1-continued
Exemplary Compounds.
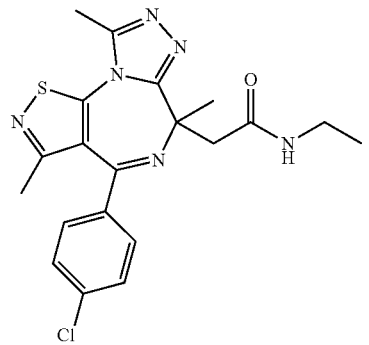 [SMILES: CCNC(=O)CC1(C)N=C(c2ccc(Cl)cc2)c2c(C)nsc2-n2c(C)nnc21]
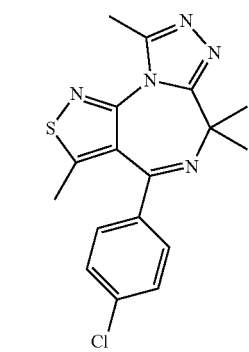
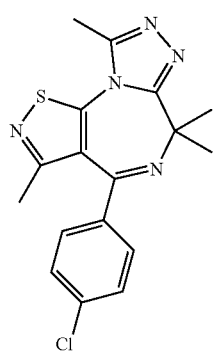 [SMILES: Cc1nsc2c1C(c1ccc(Cl)cc1)=NC(C)(C)c1nnc(C)n1-2]
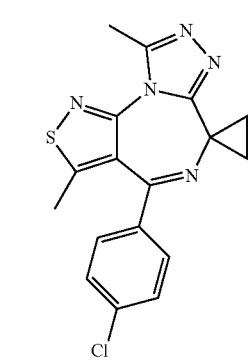
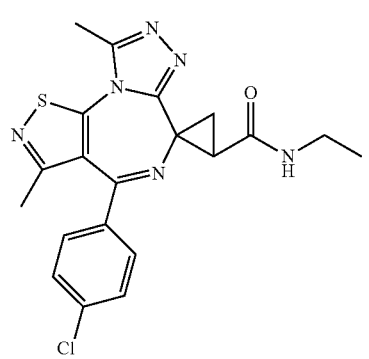 [SMILES: CCNC(=O)C1CC12N=C(c1ccc(Cl)cc1)c1c(C)nsc1-n1c(C)nnc12]
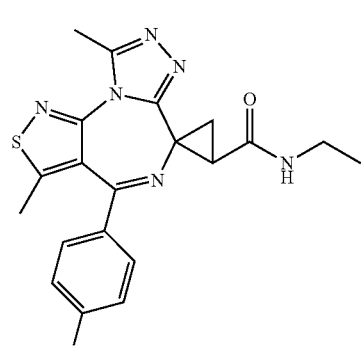
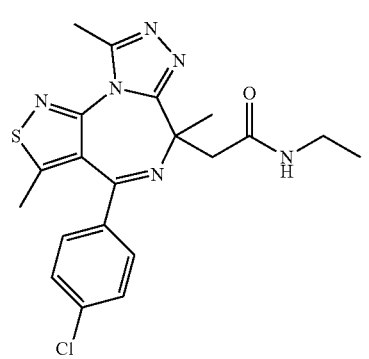 [SMILES: CCNC(=O)CC1(C)N=C(c2ccc(Cl)cc2)c2c(nsc2C)-n2c(C)nnc21]
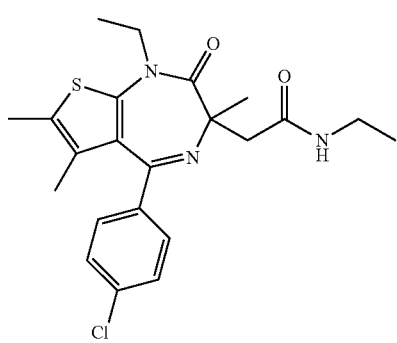 [SMILES: CCNC(=O)CC1(C)N=C(c2ccc(Cl)cc2)c2c(sc(C)c2C)N(CC)C1=O]

TABLE 1-continued
Exemplary Compounds.
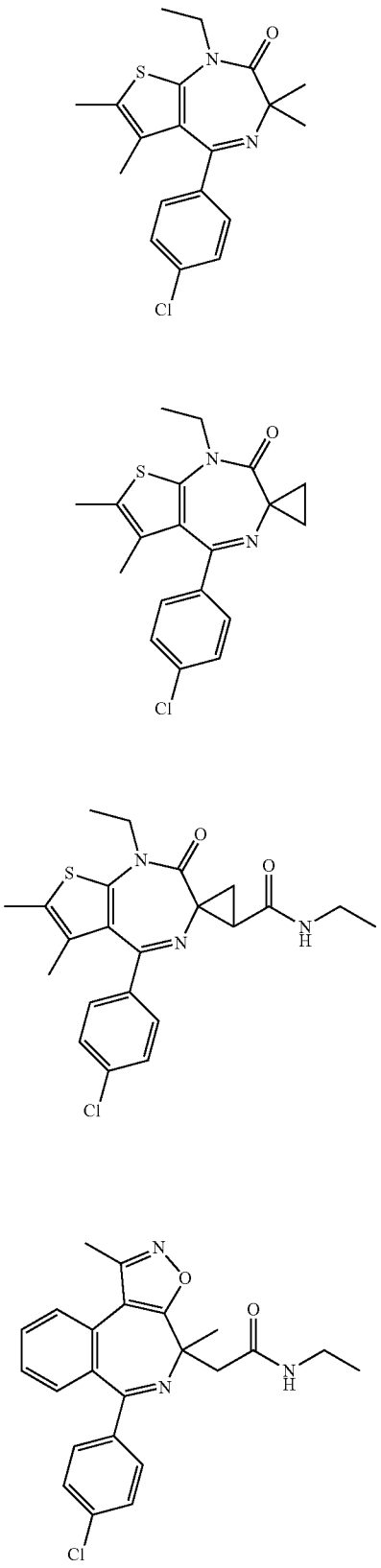
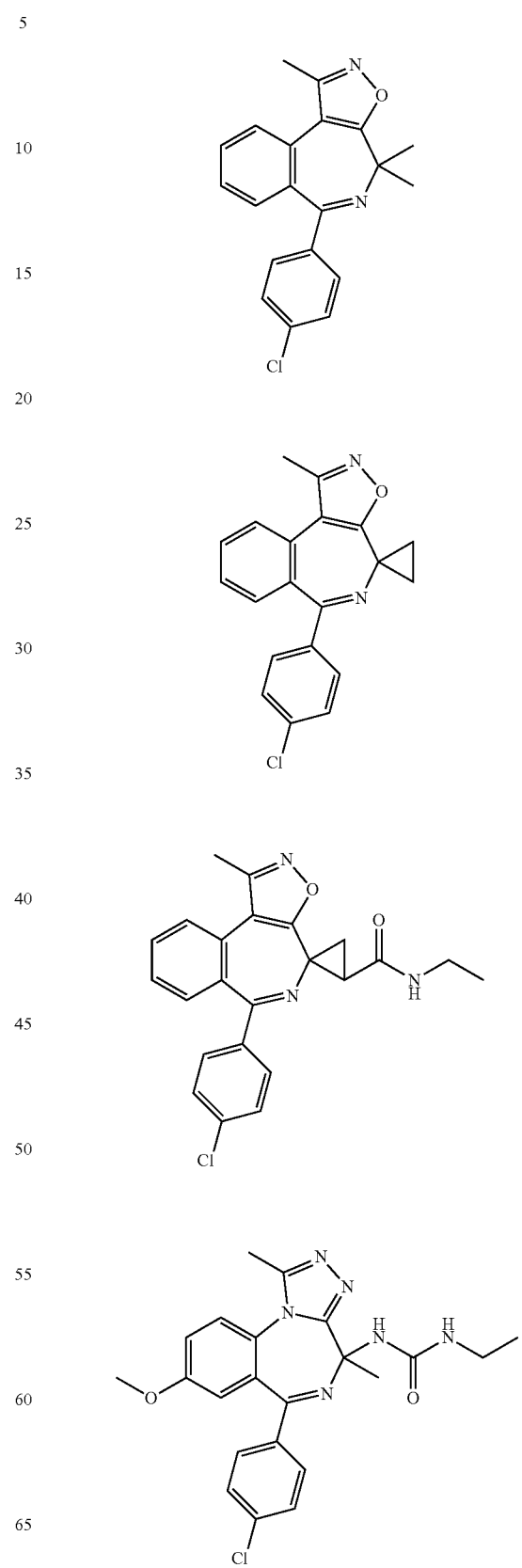

TABLE 1-continued
Exemplary Compounds.
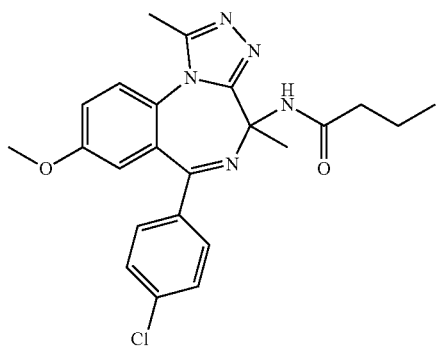 [SMILES: CCCC(=O)NC1(C)N=C(c2ccc(Cl)cc2)c2cc(OC)ccc2-n2c(C)nnc21]
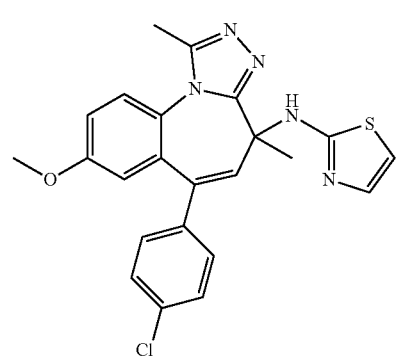 [SMILES: COc1ccc2c(c1)C(c1ccc(Cl)cc1)=CC(C)(Nc1nccs1)c1nnc(C)n1-2]
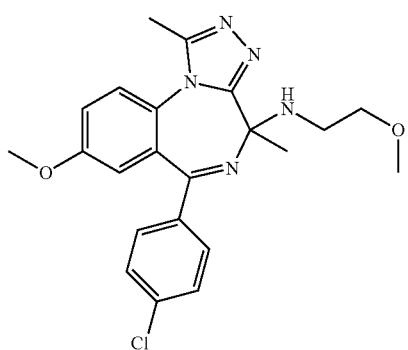
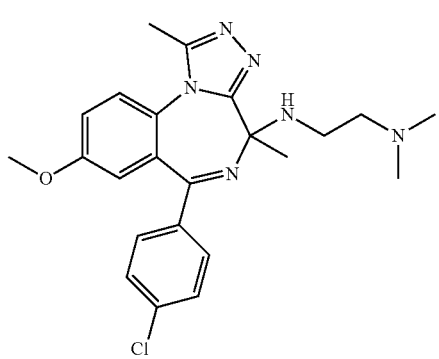
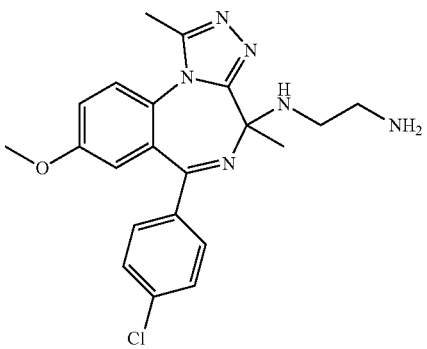 [SMILES: COc1ccc2c(c1)C(c1ccc(Cl)cc1)=NC(C)(NCCN)c1nnc(C)n1-2]
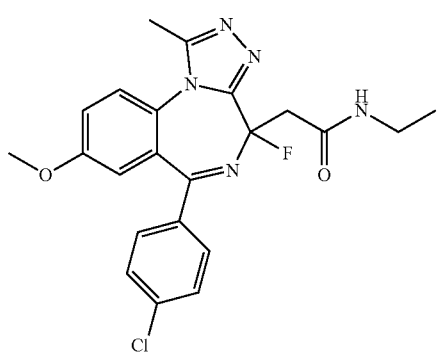 [SMILES: CCNC(=O)CC1(F)N=C(c2ccc(Cl)cc2)c2cc(OC)ccc2-n2c(C)nnc21]
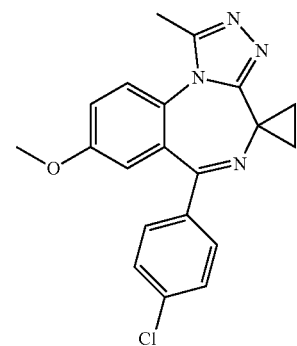 [SMILES: COc1ccc2c(c1)C(c1ccc(Cl)cc1)=NC1(CC1)c1nnc(C)n1-2]
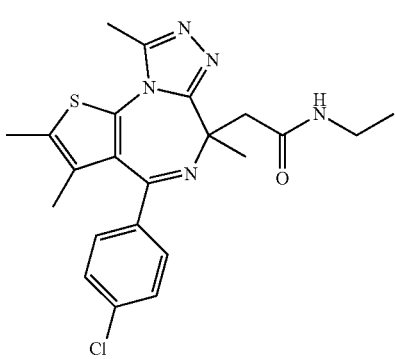

TABLE 1-continued
Exemplary Compounds.
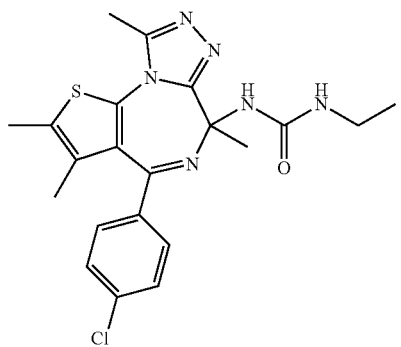 [SMILES: CCCC(=O)NC1(C)N=C(c2ccc(Cl)cc2)c2c(sc(C)c2C)-n2c(C)nnc21]
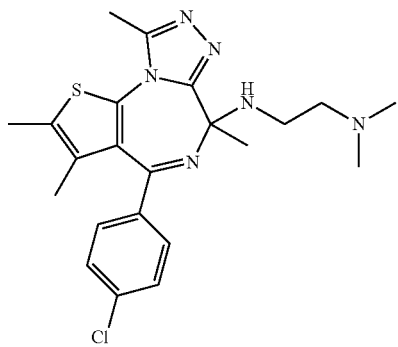
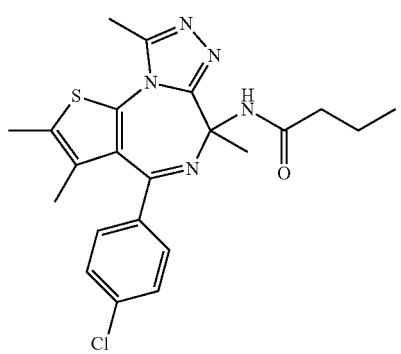
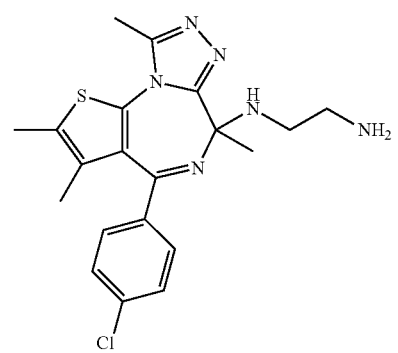 [SMILES: Cc1sc2c(c1C)C(c1ccc(Cl)cc1)=NC(C)(NCCN)c1nnc(C)n1-2]
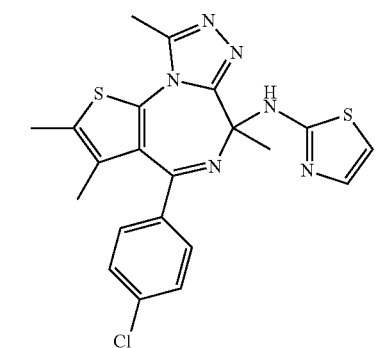
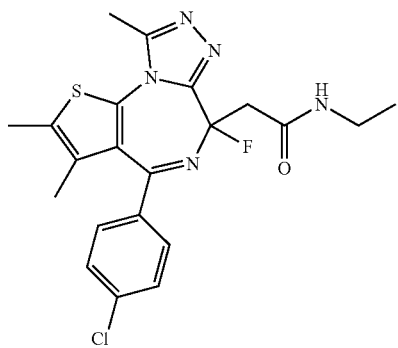 [SMILES: CCNC(=O)CC1(F)N=C(c2ccc(Cl)cc2)c2c(sc(C)c2C)-n2c(C)nnc21]
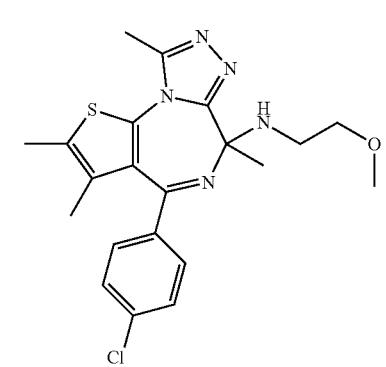
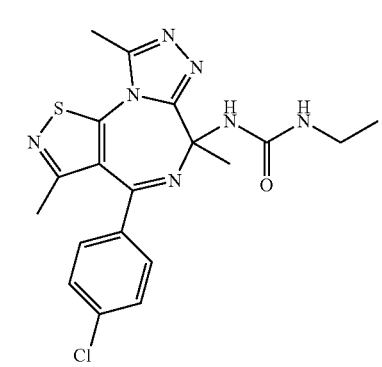 [SMILES: CCNC(=O)NC1(C)N=C(c2ccc(Cl)cc2)c2c(C)nsc2-n2c(C)nnc21]

TABLE 1-continued

Exemplary Compounds.

TABLE 1-continued
Exemplary Compounds.
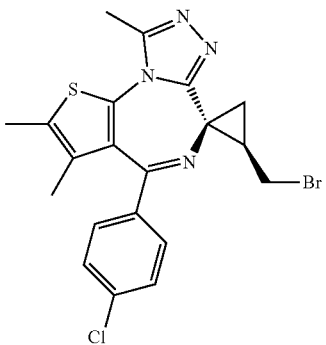 [SMILES: Cc1sc2c(c1C)C(c1ccc(Cl)cc1)=N[C@]1(C[C@H]1CBr)c1nnc(C)n1-2]
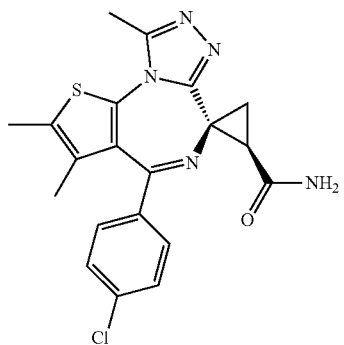 [SMILES: Cc1sc2c(c1C)C(c1ccc(Cl)cc1)=N[C@]1(C[C@H]1C(N)=O)c1nnc(C)n1-2]
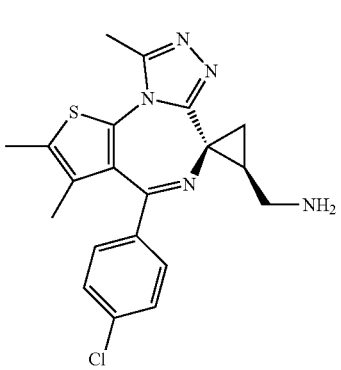 [SMILES: Cc1sc2c(c1C)C(c1ccc(Cl)cc1)=N[C@]1(C[C@H]1CN)c1nnc(C)n1-2]
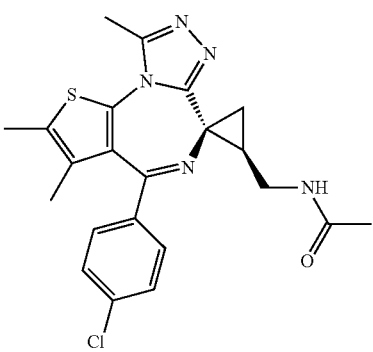 [SMILES: CC(=O)NC[C@@H]1C[C@]12N=C(c1ccc(Cl)cc1)c1c(sc(C)c1C)-n1c(C)nnc12]
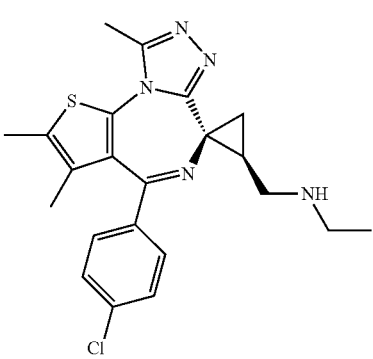 [SMILES: CCNC[C@@H]1C[C@]12N=C(c1ccc(Cl)cc1)c1c(sc(C)c1C)-n1c(C)nnc12]

TABLE 1-continued
Exemplary Compounds.
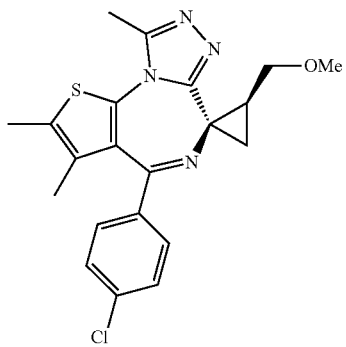 [SMILES: COC[C@H]1C[C@@]12N=C(c1ccc(Cl)cc1)c1c(sc(C)c1C)-n1c(C)nnc12]
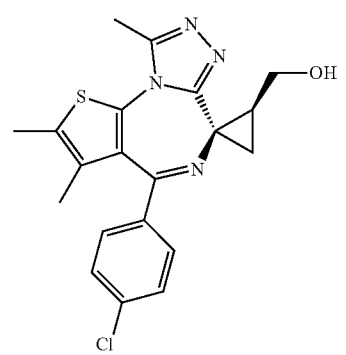 [SMILES: Cc1sc2c(c1C)C(c1ccc(Cl)cc1)=N[C@@]1(C[C@@H]1CO)c1nnc(C)n1-2]
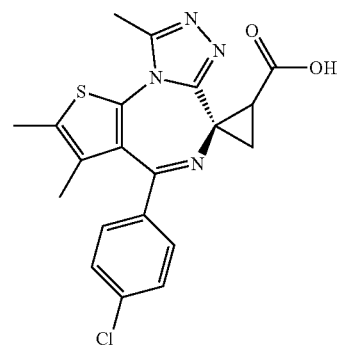 [SMILES: Cc1sc2c(c1C)C(c1ccc(Cl)cc1)=N[C@@]1(CC1C(=O)O)c1nnc(C)n1-2]
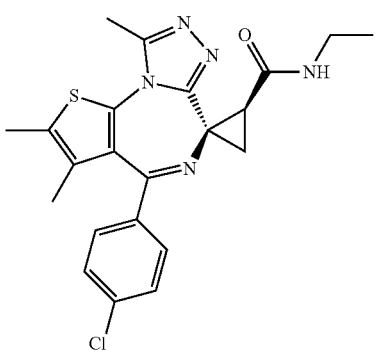 [SMILES: CCNC(=O)[C@H]1C[C@@]12N=C(c1ccc(Cl)cc1)c1c(sc(C)c1C)-n1c(C)nnc12]
TABLE 1-continued
Exemplary Compounds.
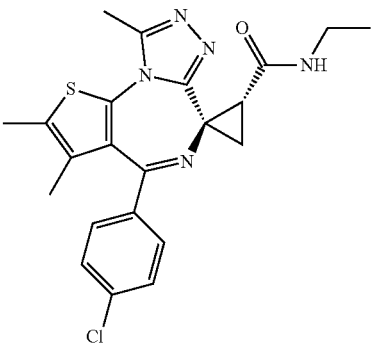 [SMILES: CCNC(=O)[C@@H]1C[C@@]12N=C(c1ccc(Cl)cc1)c1c(sc(C)c1C)-n1c(C)nnc12]
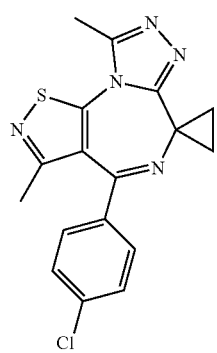 [SMILES: Cc1nsc2c1C(c1ccc(Cl)cc1)=NC1(CC1)c1nnc(C)n1-2]
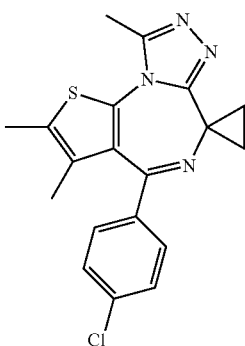 [SMILES: Cc1sc2c(c1C)C(c1ccc(Cl)cc1)=NC1(CC1)c1nnc(C)n1-2]
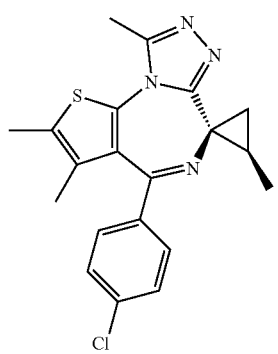

TABLE 1-continued
Exemplary Compounds.
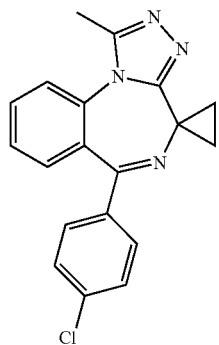 [SMILES: Cc1nnc2n1-c1ccccc1C(c1ccc(Cl)cc1)=NC21CC1]
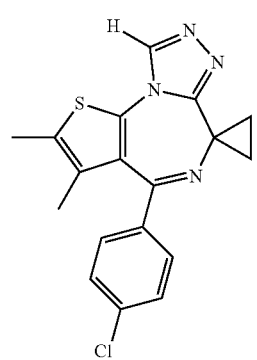 [SMILES: Cc1sc2c(c1C)C(c1ccc(Cl)cc1)=NC1(CC1)c1nncn1-2]
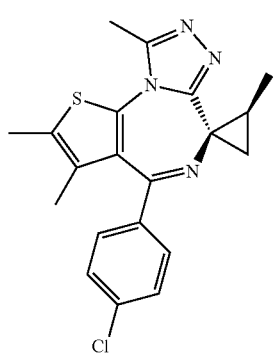
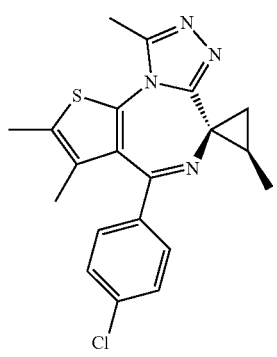
TABLE 1-continued
Exemplary Compounds.
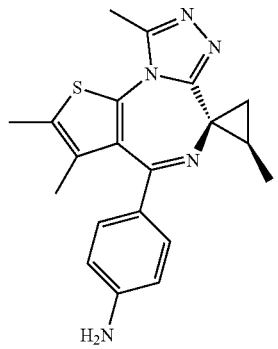
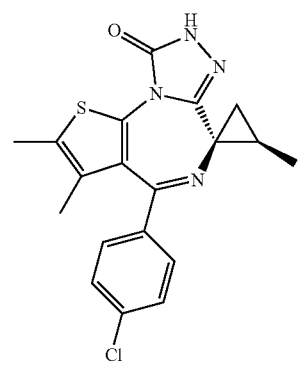
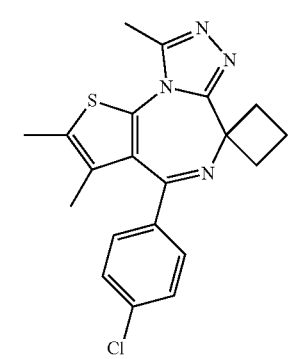 [SMILES: Cc1sc2c(c1C)C(c1ccc(Cl)cc1)=NC1(CCC1)c1nnc(C)n1-2]
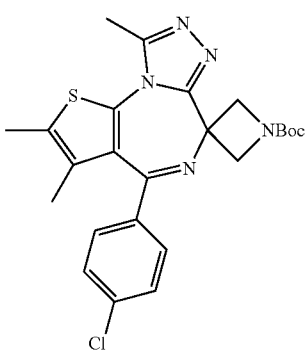 [SMILES: Cc1sc2c(c1C)C(c1ccc(Cl)cc1)=NC1(CN(C(=O)OC(C)(C)C)C1)c1nnc(C)n1-2]

TABLE 1-continued

Exemplary Compounds.

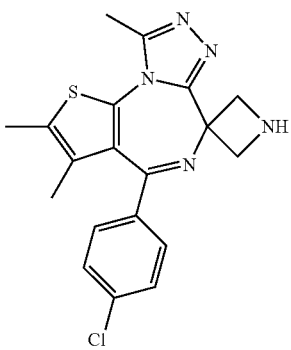 [SMILES: Cc1sc2c(c1C)C(c1ccc(Cl)cc1)=NC1(CNC1)c1nnc(C)n1-2]

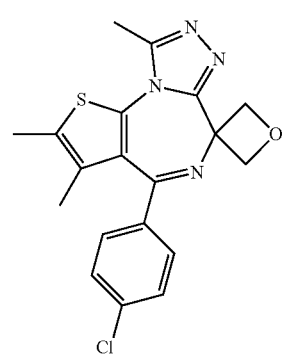 [SMILES: Cc1sc2c(c1C)C(c1ccc(Cl)cc1)=NC1(COC1)c1nnc(C)n1-2]

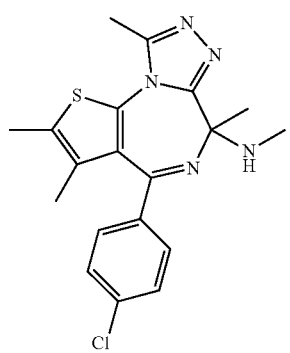

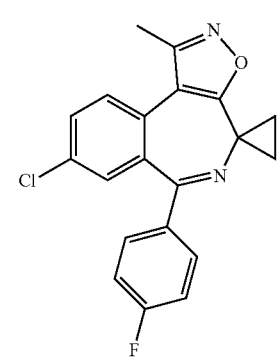 [SMILES: Cc1noc2c1-c1ccc(Cl)cc1C(c1ccc(F)cc1)=NC21CC1]

TABLE 1-continued

Exemplary Compounds.

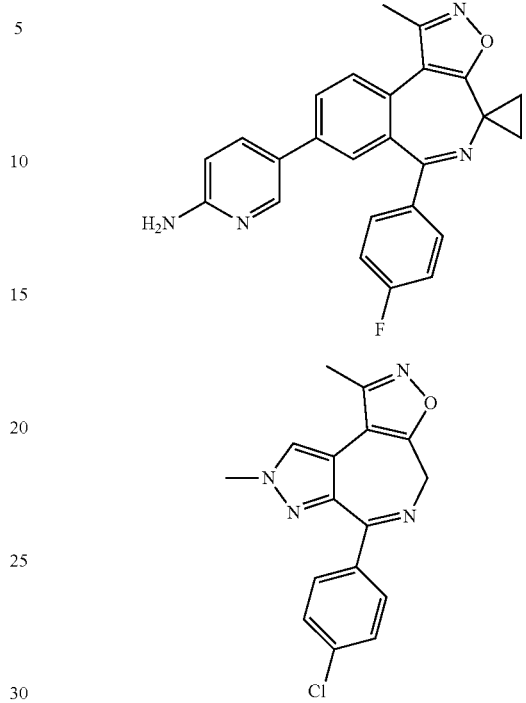

In certain embodiments, the present invention provides a method of inhibiting a bromodomain-containing protein (such as a BET protein, e.g., BRD2, BRD3, BRD4, and/or BRDT) comprising contacting said bromodomain-containing protein with any compound depicted in Table 1, above, or a pharmaceutically acceptable salt or composition thereof.

4. Uses, Formulation and Administration

Pharmaceutically Acceptable Compositions

According to another embodiment, the present invention provides a method of inhibiting a bromodomain-containing protein (such as a BET protein, e.g., BRD2, BRD3, BRD4, and/or BRDT) using a composition comprising a compound of formula I or II or a pharmaceutically acceptable derivative thereof and a pharmaceutically acceptable carrier, adjuvant, or vehicle. The amount of a compound of formula I or II in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, the amount of compound in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, a provided composition is formulated for administration to a patient in need of such composition. In some embodiments, a provided composition is formulated for oral administration to a patient.

The term "patient," as used herein, means an animal, such as a mammal, such as a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of one or more bromodomain-containing proteins (such as a BET protein, e.g., BRD2, BRD3, BRD4, and/or BRDT), or a mutant thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of activity of one or more proteins involved in epigenetic regulation. Thus, in some embodiments, the present invention provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided compound or composition.

Epigenetics is the study of heritable changes in gene expression caused by mechanisms other than changes in the underlying DNA sequence. Molecular mechanisms that play a role in epigenetic regulation include DNA methylation and chromatin/histone modifications. Chromatin recognition, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) *Curr. Opin. Genet. Dev.* 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) *Nature* 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

One type of histone modification, lysine acetylation, is recognized by bromodomain-containing proteins. Bromodomain-containing proteins are components of transcription factor complexes and determinants of epigenetic memory (Dey, et al. (2009) *Mol. Biol. Cell* 20:4899-4909). There are 46 human proteins containing a total of 57 bromodomains discovered to date. One family of bromodomain-containing proteins, BET proteins (BRD2, BRD3, BRD4, and BRDT) have been used to establish proof-of-concept for targeting protein-protein interactions of epigenetic "readers," as opposed to chromatin-modifying enzymes, or so-called epigenetic "writers" and "erasers" (Filippakopoulos, et al. "Selective Inhibition of BET Bromodomains," *Nature* (published online Sep. 24, 2010); Nicodeme, et al. "Suppression of Inflammation by a Synthetic Histone Mimic," *Nature* (published online Nov. 10, 2010)).

Examples of proteins inhibited by the compounds and compositions described herein and against which the methods described herein are useful include bromodomain-containing proteins, such as BET proteins, such as BRD2, BRD3, BRD4, and/or BRDT, or an isoform or mutant thereof.

The activity of a provided compound, or composition thereof, as an inhibitor of a bromodomain-containing protein, such as a BET protein, such as BRD2, BRD3, BRD4, and/or BRDT, or an isoform or mutant thereof, may be assayed in vitro, in vivo, or in a cell line. In vitro assays include assays that determine inhibition of bromodomain-containing proteins, such as BET proteins, such as BRD2, BRD3, BRD4, and/or BRDT, or a mutant thereof. Alternatively, inhibitor binding may be determined by running a competition experiment where a provided compound is incubated with a bromodomain-containing protein, such as a BET protein, such as BRD2, BRD3, BRD4, and/or BRDT bound to known ligands, labeled or unlabeled. Detailed conditions for assaying a provided compound as an inhibitor of a bromodomain-containing protein, such as a BET protein, such as BRD2, BRD3, BRD4, and/or BRDT or a mutant thereof, are set forth in the Examples below.

Acetylated histone recognition and bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey, et al. (2009) *Mol. Biol. Cell* 20:4899-4909). BRD4 also physically associates with Mediator and P-TEFb (CDK9/cyclin Ti) to facilitate transcriptional elongation (Yang, et al. (2005) *Oncogene* 24:1653-1662; Yang, et al. (2005) *Mol. Cell* 19:535-545). CDK9 is a validated target in chronic lymphocytic leukemia (CLL), and is linked to c-Myc-dependent transcription (Phelps, et al. *Blood* 113:2637-2645; Rahl, et al. (2010) *Cell* 141:432-445).

BRD4 is translocated to the NUT protein in patients with lethal midline carcinoma, an aggressive form of human squamous carcinoma (French, et al. (2001) *Am. J. Pathol.* 159:1987-1992; French, et al. (2003) *Cancer Res.* 63:304-307). In vitro analysis with RNAi supports a causal role for BRD4 in this recurrent t(15;19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," *Nature* (published online Sep. 24, 2010)).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression (Hargreaves, et al. (2009) *Cell* 138:129-145; LeRoy, et al. (2008) *Mol. Cell* 30:51-60; Jang, et al. (2005) *Mol. Cell* 19:523-534; Yang, et al. (2005) *Mol. Cell* 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shoc and bacteria-induced sepsis in vivo (Nicodeme, et al. "Suppression of Inflammation by a Synthetic Histone Mimic," *Nature* (published online Nov. 10, 2010)).

Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and to activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Barr virus).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In certain embodiments, a provided compound inhibits one or more of BRD2, BRD3, BRD4, BRDT, and/or another member of the bromodomain-containing proteins, or a mutant thereof. In some embodiments, a provided compound inhibits two or more of BRD2, BRD3, BRD4, BRDT, and/or another member of the bromodomain-containing proteins, or a mutant thereof. Provided compounds are inhibitors of one of more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present invention provides a method for treating an bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a provided compound, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present invention relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of this invention include, but are not limited to, cancer and other proliferative disorders, inflammatory diseases, sepsis, autoimmune disease, and viral infection. In one embodiment, a human patient is treated with a compound of formula I and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient.

The invention further relates to a method for treating or ameliorating cancer or another proliferative disorder by administration of an effective amount of a compound according to this invention to a mammal, in particular a human in need of such treatment. In some aspects of the invention, the disease to be treated by the methods of the present invention is cancer. Examples of cancers treated using the compounds and methods described herein include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, actue promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinea128oblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some embodiments, the present invention provides a method of treating a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The invention further relates to a method for treating infectious and noninfectious inflammatory events and autoimmune and other inflammatory diseases by administration of an effective amount of a provided compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irrtiable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherscleroisis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In some embodiments, the present invention provides a method of treating systemic inflammatory response syndromes such as LPS-induced endotoxic shock and/or bacteria-induced sepsis by administration of an effective amount of a provided compound to a mammal, in particular a human in need of such treatment.

The invention further relates to a method for treating viral infections and diseases by administration of an effective amount of a provided compound to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

The invention further provides a method of treating a subject, such as a human, suffering from one of the abovementioned conditions, illnesses, disorders or diseases. The method comprises administering a therapeutically effective amount of one or more provided compounds, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The invention further provides a therapeutic method of modulating protein methylation, gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more provided compounds.

The invention further provides a method of regulating endogenous or heterologous promoter activity by contacting a cell with a provided compound.

The invention further relates to the use of provided compounds for the production of pharmaceutical compositions which are employed for the treatment and/or prophylaxis and/or amelioration of the diseases, disorders, illnesses and/or conditions as mentioned herein.

The invention further relates to the use of provided compounds for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

Compounds or compositions described herein may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

According to some embodiments, the invention relates to a method of inhibiting bromodomain-containing proteins in a biological sample comprising the step of contacting said biological sample with a provided compound, or a composition thereof.

According to some embodiments, the invention relates to a method of inhibiting a bromodomain-containing protein, such as a BET protein, such as BRD2, BRD3, BRD4 and/or BRDT, or a mutant thereof, activity in a biological sample comprising the step of contacting said biological sample with a provided compound, or a composition thereof.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of activity of an protein, e.g., a bromodomain-containing protein, such as a BET protein, such as BRD2, BRD3, BRD4 and/or BRDT, or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting activity of one or more bromodomain-containing protein, such as a BET protein, such as BRD2, BRD3, BRD4, and/or BRDT, or a mutant thereof, in a patient comprising the step of administering to said patient a provided compound, or a composition comprising said compound. In certain embodiments, the present invention provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a provided compound or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other antiproliferative agents may be combined with a provided compound to treat proliferative diseases and cancer. Examples of therapies or anticancer agents that may be used in combination with compounds of formula I include surgery, radiotherapy (e.g., gamma-Radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effects (e.g., an antiemetic), and any other approved chemotherapeutic drug.

A provided compound may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, roglethimide, pyridoglutethimide, trilostane, testolactone, ketokonazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxines etoposide and teniposide.

Exemplary microtubule active agents include microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof.

Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin compounds include carboplatin, cis-platin, cisplatinum, and oxaliplatin.

Exemplary methionine aminopeptidase inhibitors include bengamide or a derivative thereof and PPI-2458.

Exemplary bisphosphonates include etridonic acid, clodronic acid, tiludronic acid, pamidronic acid, alendronic acid, ibandronic acid, risedronic acid and zoledronic acid.

Exemplary antiproliferative antibodies include trastuzumab, trastuzumab-DM1, cetuximab, bevacizumab, rituximab, PRO64553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Exemplary Flt-3 inhibitors include PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing or inhibiting the activity of the platelet-derived growth factor-receptors (PDGFR), such as a compound which targets, decreases, or inhibits the activity of PDGFR, such as an N-phenyl-2-pyrimidine-amine derivatives, such as imatinib, SU101, SU6668 and GFB-111; b) a compound targeting, decreasing or inhibiting the activity of the fibroblast growth factor-receptors (FGFR); c) a compound targeting, decreasing or inhibiting the activity of the insulin-like growth factor receptor I (IGF-IR), such as a compound which targets, decreases, or inhibits the activity of IGF-IR; d) a compound targeting, decreasing or inhibiting the activity of the Trk receptor tyrosine kinase family, or ephrin B4 inhibitors; e) a compound targeting, decreasing or inhibiting the activity of the Ax1 receptor tyrosine kinase family; f) a compound targeting, decreasing or inhibiting the activity of the Ret receptor tyrosine kinase; g) a compound targeting, decreasing or inhibiting the activity of the Kit/SCFR receptor tyrosine kinase, such as imatinib; h) a compound targeting, decreasing or inhibiting the activity of the c-Kit receptor tyrosine kinases, such as imatinib; i) a compound targeting, decreasing or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; lsis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, getfitinib, erlotinib, OSI-774, CI-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing or inhibiting the activity of the c-Met receptor.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide and TNP-470.

Additional exemplary chemotherapeutic compounds, one or more of which may be used in combination with provided compounds, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostain, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisol, cortexolone, 17α-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action.

For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinrole, pramipexole, bromocriptine, pergolide, trihexephendyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a provided compound, can be prepared and administered as described in the art.

Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, an embodiment of the invention provides a single unit dosage form comprising a provided compound, an additional therapeutic agent, and a pharmaceutically acceptable carrier, adjuvant, or vehicle for use in the methods of the invention.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

EXAMPLE 1

Synthesis of (2-bromophenyl)(4-chlorophenyl)methanone

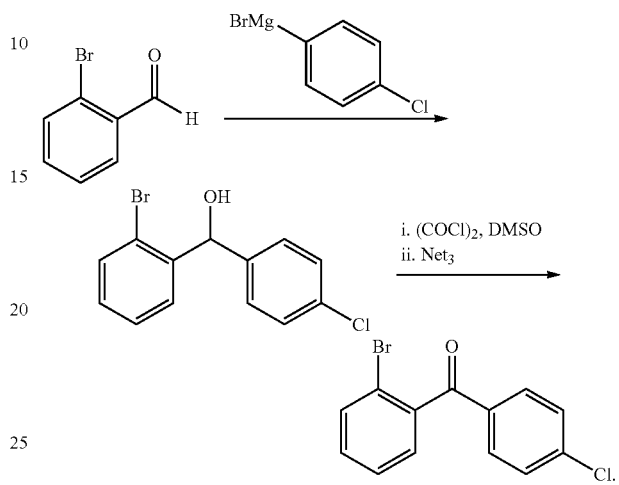

To a solution of 2-bromobenzaldehyde (3.15 ml, 27.0 mmol) and THF (135 ml) at 0° C. was added (4-chlorophenyl)magnesium bromide solution (29.7 ml, 1M in THF, 29.7 mmol). The reaction was stirred at 0° C. for 30 min before addition of a saturated solution of ammonium chloride. The layers were separated and the aqueous extracted with EtOAc. The combined organics were washed with brine, dried over $Na_2SO_4$, filtered, and concentrated. The crude residue was purified via Biotage to afford (2-bromophenyl)(4-chlorophenyl)methanol. To a solution of DCM (100 ml) and oxalyl chloride (2.471 ml, 28.2 mmol) at −78° C. was added DMSO (3.34 ml, 47.0 mmol) and the reaction stirred at −78° C. for 15 min. After 15 min a solution of (2-bromophenyl)(4-chlorophenyl)methanol in DCM (25 ml) was added dropwise and stirred for 15 min at −78° C. before addition of $Et_3N$ (9.84 ml, 70.6 mmol). The cold bath was removed and the reaction was warmed to room temperature. To this solution was added water and the layers separated. The aqueous was extracted with DCM and the combined organics were dried over $Na_2SO_4$, filtered, and concentrated. The crude residue was purified via Biotage (EtOAc/hex) to afford (2-bromophenyl)(4-chlorophenyl)methanone. m/z (ESI) 295, 297 [M+H]$^+$.

EXAMPLE 2

Synthesis of prop-2-yn-1-yl benzoate

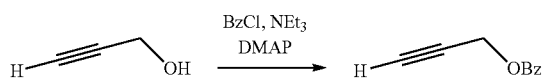

To a solution of prop-2-yn-1-ol (3.63 ml, 62.4 mmol), DCM (180 ml), and $Et_3N$ (17.40 ml, 125 mmol) at 0° C. were added benzoyl chloride (7.25 ml, 62.4 mmol) and DMAP (0.381 g, 3.12 mmol). The reaction was stirred while warming to room temperature overnight. The reaction was diluted with water and the layers separated. The aqueous was extracted with DCM and the combined organics were dried over $Na_2SO_4$, filtered, and concentrated to afford prop-2-yn-1-yl benzoate which was used in subsequent reactions without further purification. m/z (ESI) 161 [M+H]$^+$.

EXAMPLE 3

Synthesis of (3-methylisoxazol-5-yl)methyl benzoate

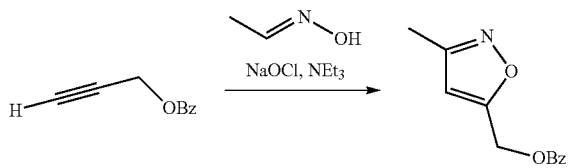

To a solution of chloroform, Et$_3$N (0.435 ml, 3.12 mmol), prop-2-ynyl benzoate (1 g, 6.24 mmol), and (E)-acetaldehyde oxime (0.571 ml, 9.37 mmol) at 0° C. was added bleach (23.12 ml, 18.73 mmol). The reaction was stirred overnight before the layers were separated and the aqueous extracted with DCM. The combined organics were dried over Na$_2$SO$_4$, filtered, and concentrated. The crude residue was purified via Biotage (EtOAc/hex) to afford (3-methylisoxazol-5-yl)methyl benzoate. m/z (ESI) 218 [M+H]$^+$.

EXAMPLE 4

Synthesis of (4-bromo-3-methylisoxazol-5-yl)methyl benzoate

To a resealable vial was added (3-methylisoxazol-5-yl) methyl benzoate (907 mg, 4.18 mmol), AcOH (3.5 ml, 61.1 mmol), and NBS (892 mg, 5.01 mmol). The reaction was heated to 110° C. overnight. The reaction was cooled to room temperature and diluted with water. The aqueous was extracted with EtOAc and the combined organics were washed with brine, dried over Na$_2$SO$_4$, filtered, and concentrated. The crude residue was purified via Biotage (EtOAc/hex) to afford (4-bromo-3-methylisoxazol-5-yl)methyl benzoate. m/z (ESI) 296, 298 [M+H]$^+$.

EXAMPLE 5

Synthesis of 3-(((4-methoxybenzyl)oxy)methyl)-5-methylisoxazole

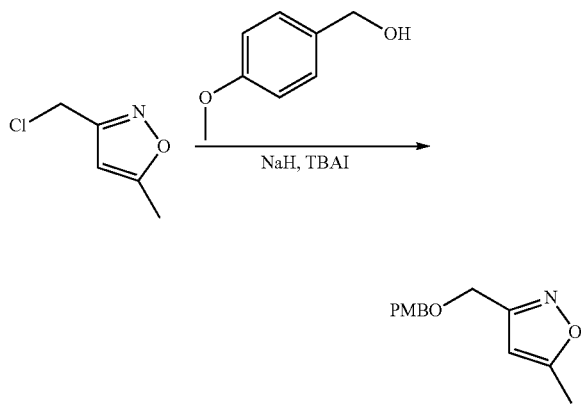

To a resealable vial were added NaH (193 mg, 60% dispersion in mineral oil, 4.82 mmol) and THF. The vial was cooled to 0° C. before addition of (4-methoxyphenyl)methanol (639 µl, 5.14 mmol) and the reaction stirred at 0° C. for 30 min before addition of 3-(chloromethyl)-5-methylisoxazole (423 mg, 3.22 mmol) and tetrabutylammonium iodide (119 mg, 0.322 mmol). The reaction was heated to reflux overnight. The vial was cooled to room temperature before being diluted with ammonium chloride solution. The aqueous was extracted with EtOAc and the combined organics were washed with brine, dried over Na$_2$SO$_4$, filtered, and concentrated. The crude residue was purified via Biotage (EtOAc/hex) to afford 3-((4-methoxybenzyloxy)methyl)-5-methylisoxazole. m/z (ESI) 256 [M+Na]$^+$.

EXAMPLE 6

Methyl 2-bromo-4,5-dimethylthiophene-3-carboxylate

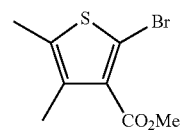

To a solution of methyl 4,5-dimethylthiophene-3-carboxylate (1.89 g, 11.10 mmol) in DMF (10 mL) was added N-bromosuccinimide (2.37 g, 13.32 mmol) at room temperature. The reaction mixture turned orange over time and was allowed to stir for 2 h, at which time LC-MS analysis indicated complete consumption of the methyl 4,5-dimethylthiophene-3-carboxylate. To the solution was added MTBE and water. The aqueous layer was extracted with MTBE (2×), the combined orange organic layer was washed with 1% sodium thiosulfate, followed by water (2×). The organic phase was dried over Na$_2$SO$_4$ and concentrated to give yellow oil. The crude reaction mixture was purified on Biotage system (isocratic elution 2% EtOAc:98% Hexanes) to give the titled compound as a light yellow solid (2.61 g, 10.5 mmol, 94% yield). LC/MS: m/z 249 [M+H]$^+$.

EXAMPLE 7

(3-Methylisoxazol-5-yl)methyl acetate

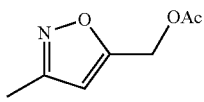

To a suspension of N-chlorosuccimide (71.5 g, 535 mmol) in CHCl$_3$ (360 mL) and pyridine (1.61 g, 20.3 mmol) was added a solution of (E)-acetaldehyde oxime (31.6 g, 535 mmol). After a period of 1 h, propargylacetate (35.0 g, 357 mmol) in a minimum of CHCl$_3$ was added to the previous mixture. Triethylamine (114 g, 1124 mmol) was then added dropwise and the reaction mixture was cooled in a water bath in order to maintain the internal temperature below the boiling point. After a period of 1 h, the reaction mixture was concentrated in vacuo followed by the addition of EtOAc. The mixture was filtered on a glass filter and the solid washed with EtOAc, the combined filtrates were evaporated. After evaporation, additional EtOAc was added and the previous process repeated. The EtOAc was evaporated and the crude product was purified on a on Biotage system (isocratic elution 40% EtOAc:60% Hexanes) and the fractions followed by LC/MS to provide the titled compound as a clear oil. LC/MS: m/z 156 [M+H]$^+$.

EXAMPLE 8

(4-Bromo-3-methylisoxazol-5-yl)methyl acetate

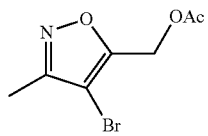

To a solution of (3-methylisoxazol-5-yl)methyl acetate (0.979 g, 6.31 mmol) in AcOH (10 mL, 175 mmol) was added N-bromosuccinimide (1.30 g, 7.30 mmol) and H$_2$SO$_4$ (0.65 mL, 12.19 mmol). The reaction was heated to 110° C. After 1 h, the reaction mixture was cooled to room temperature and carefully poured into a beaker containing ice and saturated NaHCO$_3$. The bi-phasic was vigorously stirred and basic solution (pH~8-9) was extracted with EtOAc (2×15 mL). The organic layer was washed with 2% sodium thiosulfate, washed with brine (20 mL), dried over Na$_2$SO$_4$, and concentrated to give a light yellow oil. The oil was purified on Biotage system (isocratic elution 10% EtOAc:90% Hexanes) to give the titled compound (1.30 g, 5.55 mmol, 88% Yield) as a colorless yellow oil. LC/MS: m/z 234 [M+H]$^+$.

EXAMPLE 9

(3-Methyl-4-(4,4,5,5-tetramethyl-1,3,2-dioxaborolan-2-yl)isoxazol-5-yl)methyl acetate

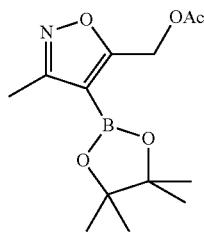

To a 500 mL flask (under N$_2$ (g)) was added dichlorobis(acetonitrile)palladium(II) (0.551 g, 2.12 mmol) and dicyclohexyl(2',6'-dimethoxybiphenyl-2-yl)phosphine (3.50 g, 8.53 mmol). To the solids was sequentially added a solution of (4-bromo-3-methylisoxazol-5-yl)methyl acetate (24.8 g, 106 mmol) in 1,4-dioxane (65 mL), Et$_3$N (44.3 mL, 318 mmol), and 4,4,5,5-tetramethyl-1,3,2-dioxaborolane (24 mL, 160 mmol). The flask was sequentially evacuated and purged under N$_2$ and this process was repeated three times. The reaction mixture was heated to 110° C. (under a constant stream of N$_2$ (g)) and allowed to stir for ~4 h. LC-MS analysis at this point showed complete conversion of the starting bromo-isoxazole. The reaction mixture was cooled to room temperature and EtOAc (100 mL) was added. After 15 min of stirring, the suspension was filtered over a pad of Celite. The filter cake was washed with EtOAc (3×100 mL), concentrated in vacuo, and the solvent was switched using 1,4-Dioxane (2×50 mL). The borate ester with used without further purification.

EXAMPLE 10

2-bromo-N,5-dimethoxy-N-methylbenzamide

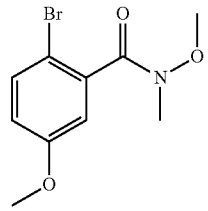

2-bromo-N,5-dimethoxy-N-methylbenzamide was prepared according to the procedure described in *Tetrahedron*, 2001, 57, 7765-7770.

EXAMPLE 11

(2-bromo-5-methoxyphenyl)(4-chlorophenyl)methanone

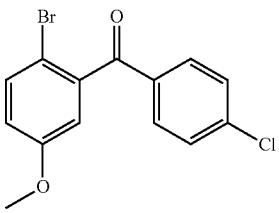 [SMILES: COc1ccc(Br)c(C(=O)c2ccc(Cl)cc2)c1]

and (4-chlorophenyl)(3-methoxyphenyl)methanone

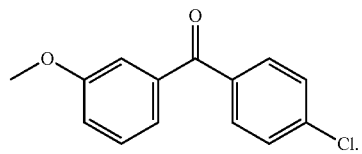 [SMILES: COc1cccc(C(=O)c2ccc(Cl)cc2)c1]

To a round bottomed flask was added 2-bromo-N,5-dimethoxy-N-methylbenzamide (6.23 g, 22.73 mmol) and THF (75 ml). To this solution was added (4-chlorophenyl)magnesium bromide (42 ml, 42.0 mmol) and the reaction stirred at room temperature overnight. The solution was diluted with water and EtOAc. The layers were separated and the aqueous was extracted with EtOAc. The combined organics were washed with brine, dried over Na2SO4, filtered, and concentrated. The crude residue was purified via Biotage (EtOAc/hex) to afford a mixture of (2-bromo-5-methoxyphenyl)(4-chlorophenyl)methanone and (4-chlorophenyl)(3-methoxyphenyl)methanone. m/z (ESI) 325, 327 [M+H]⁺.

EXAMPLE 12

(Tetrahydro-2H-pyran-4-yl)magnesium chloride

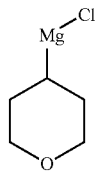

To a vigorously stirred suspension of Mg (0.500 g, 20.57 mmol) turnings and iodine (0.019 g, 0.075 mmol) in THF (5 mL) under N₂ (g) was added 1,2-dibromoethane (0.10 mL, 1.160 mmol) and 10% of a solution of 4-chlorotetrahydro-2H-pyran (1.00 mL, 9.24 mmol) in THF (5 mL). The mixture was heated to 60° C. and as the reaction mixture turned clear and Grignard initiation took place, the remainder of the solution of 4-chlorotetrahydro-2H-pyran (1.00 mL, 9.24 mmol) in THF was added slowly over 30 min. The reaction mixture was stirred at 65° C. for 2 h to deliver a solution of (tetrahydro-2H-pyran-4-yl)magnesium chloride in THF. The Grignard solution was used without any further purification.

EXAMPLE 13

Synthesis of 4-(4-chlorophenyl)-2,3,6,6,9-pentamethyl-6H-thieno[3,2-f][1,2,4]triazolo[4,3-a][1,4]diazepine (Compound 227)

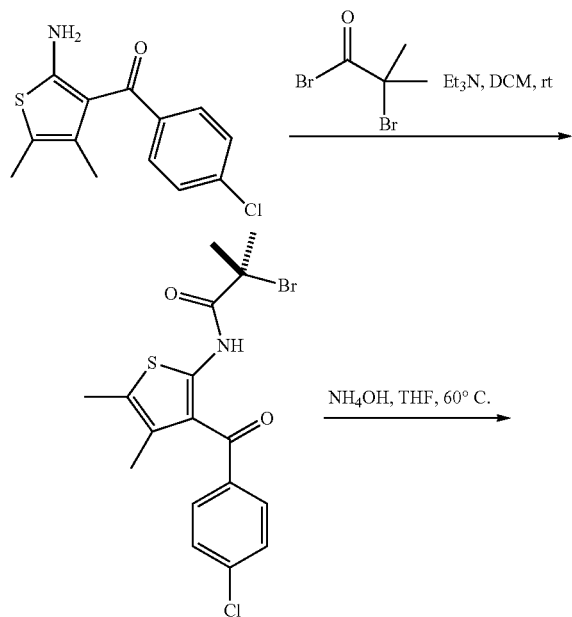

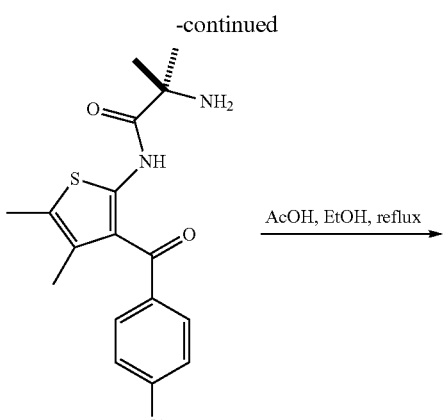

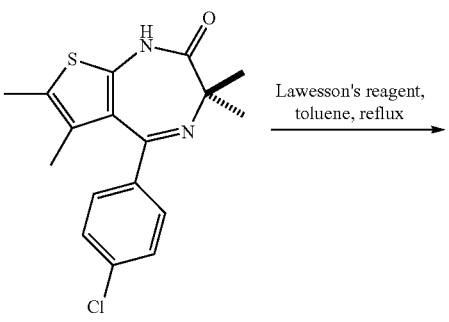

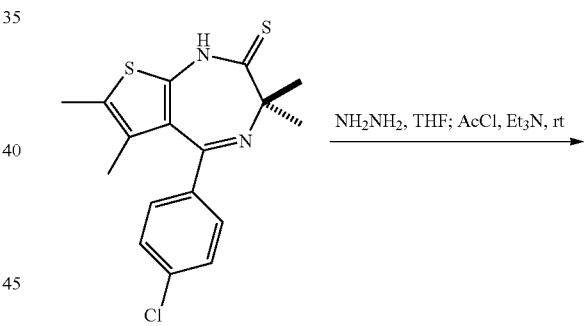

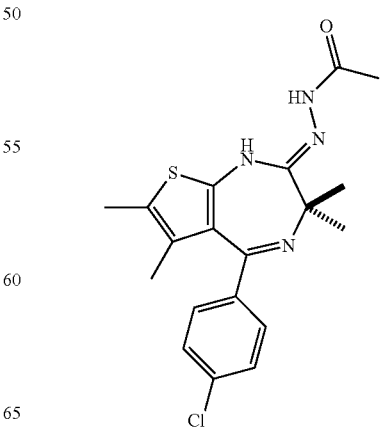

-continued

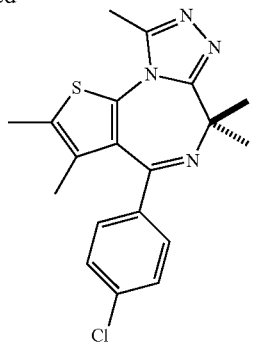

Compound 227

2-bromo-N-(3-(4-chlorobenzoyl)-4,5-dimethylthiophen-2-yl)-2-methylpropanamide A round bottomed flask was charged with (2-amino-4,5-dimethylthiophen-3-yl)(4-chlorophenyl)methanone (2 g, 7.53 mmol) and a stirbar. Dichloromethane (75 mL, 0.1 M) was added, followed by triethylamine (1.573 ml, 11.29 mmol, 1.5 equiv). The solution was cooled to 0° C. for the addition of 2-bromo-2-methylpropanoyl bromide (1.163 ml, 9.41 mmol). The solution was stirred at room temperature 1 h, at which point LC/MS analysis showed complete conversion of the starting material. The solution was washed successively with water and brine before being dried with sodium sulfate and concentrated to give a quantitative yield of 2-bromo-N-(3-(4-chlorobenzoyl)-4,5-dimethylthiophen-2-yl)-2-methylpropanamide as a yellow amorphous solid (m/z=414/416), which was used crude in the subsequent reaction.

2-amino-N-(3-(4-chlorobenzoyl)-4,5-dimethylthiophen-2-yl)-2-methylpropanamide A round bottomed flask was charged with 2-bromo-N-(3-(4-chlorobenzoyl)-4,5-dimethylthiophen-2-yl)-2-methylpropanamide (5 g, 12.06 mmol) and a stir bar, followed by tetrahydrofuran (25 mL, 0.5 M) and ammonium hydroxide (30%, 7.82 ml, 60.3 mmol, 5 equiv). The solution was stirred at 60° C. 4 h, at which point LC/MS analysis indicated complete consumption of the starting material. The solution was diluted with ethyl acetate, washed successively with water and brine, and purified by column chromatography (eluting with hexanes/ethyl acetate) to yield 2-amino-N-(3-(4-chlorobenzoyl)-4,5-dimethylthiophen-2-yl)-2-methylpropanamide as a yellow amorphous solid (m/z=351), which was used in the subsequent reaction.

5-(4-chlorophenyl)-3,3,6,7-tetramethyl-M-thieno[2,3-e][1,4]diazepin-2(3H)-one A round bottomed flask was charged with 2-amino-N-(3-(4-chlorobenzoyl)-4,5-dimethylthiophen-2-yl)-2-methylpropanamide (1 g, 2.85 mmol) and a stir bar. Ethanol (25 mL, 0.1 M) was added, followed by acetic acid (4.08 ml, 71.3 mmol, 25 equiv), and the solution was stirred at reflux 4 h before being concentrated and purified by column chromatography (eluting with hexanes/ethyl acetate) to yield 5-(4-chlorophenyl)-3,3,6,7-tetramethyl-1H-thieno[2,3-e][1,4]diazepin-2(3H)-one as a yellow amorphous solid (m/z=333) that was used in the subsequent reaction.

5-(4-chlorophenyl)-3,3,6,7-tetramethyl-M-thieno[2,3-e][1,4]diazepine-2(3H)-thione A round bottomed flask was charged with 5-(4-chlorophenyl)-3,3,6,7-tetramethyl-1H-thieno[2,3-e][1,4]diazepin-2(3H)-one (324 mg, 0.973 mmol) and a stir bar. Toluene (20 mL, 0.05 M) was added, followed by Lawesson's Reagent (217 mg, 0.535 mmol, 0.55 equiv), and the solution stirred at reflux 4 h. The solution was concentrated and purified by column chromatography (eluting with hexanes/ethyl acetate) to yield 5-(4-chlorophenyl)-3,3,6,7-tetramethyl-1H-thieno[2,3-e][1,4]diazepine-2(3H)-thione as a yellow amorphous solid (m/z=349) that was used in the subsequent reaction.

(Z)—N'-(5-(4-chlorophenyl)-3,3,6,7-tetramethyl-4H-thieno[2,3-e][1,4]diazepin-2(3H)-ylidene)acetohydrazide A round bottomed flask was charged with 5-(4-chlorophenyl)-3,3,6,7-tetramethyl-1H-thieno[2,3-e][1,4]diazepine-2(3H)-thione (123 mg, 0.353 mmol) and a stir bar. Tetrahydrofuran (10 mL, 0.05 M) was added, and the solution was cooled to 0° C. for the addition of hydrazine hydrate (132 µl, 1.763 mmol). Stirred at room temperature 30 min, at which point both TLC and LC/MS analysis indicated essentially complete consumption of the starting material. Triethylamine (295 µl, 2.115 mmol, 6 equiv) was added, followed by acetic acid chloride (150 µl, 2.115 mmol, 6 equiv) (careful! exothermic!), and the solution stirred at rt 1 h. The solution was diluted with dichloromethane and concentrated for purification by column chromatography (eluting with dichloromethane/methanol/ammonium hydroxide), which yielded (Z)—N'-(5-(4-chlorophenyl)-3,3,6,7-tetramethyl-1H-thieno[2,3-e][1,4]diazepin-2(3H)-ylidene)acetohydrazide as a dark red oil (m/z=389) that was used in the subsequent reaction.

4-(4-chlorophenyl)-2,3,6,6,9-pentamethyl-6H-thieno[3,2-f][1,2,4]triazolo[4,3-a][1,4]diazepine (Compound 227)

A disposable tube fitted with a septum was charged with (Z)—N'-(5-(4-chlorophenyl)-3,3,6,7-tetramethyl-1H-thieno[2,3-e][1,4]diazepin-2(3H)-ylidene)acetohydrazide (112 mg, 0.288 mmol) and tetrahydrofuran (10 mL). Tosic acid (75 mg, 0.394 mmol, 1.4 equiv) was added, and the solution as stirred at room temperature 30 min, at which point LC/MS analysis indicated complete consumption of the starting material. The solution was concentrated for purification by column chromatography (eluting with dichloromethane/methanol/ammonium hydroxide) to yield an off-white amorphous solid. This solid was further purified by semi-prep HPLC (water/acetonitrile/0.1% trifluoroacetic acid), free-based with a strong cation exchange solid phase extraction column (eluting with ammonia in methanol), and lyophilized to yield 4-(4-chlorophenyl)-2,3,6,6,9-pentamethyl-6H-thieno[3,2-f][1,2,4]triazolo[4,3-a][1,4]diazepine as a yellow amorphous solid (m/z=371) (46 mg, 43%). $^1$H NMR (400 MHz; DMSO): δ 7.48 (s, 4H), 2.60 (s, 3H), 2.39 (s, 3H), 1.97 (s, 3H), 1.57 (s, 3H), 1.07 (s, 3H).

EXAMPLE 14

Synthesis of (1S,2R)-4'-(4-chlorophenyl)-2-(methoxymethyl)-2',3',9'-trimethylspiro[cyclopropane-1,6'-thieno[3,2-f][1,2,4]triazolo[4,3-a][1,4]diazepine] (Compound 202)

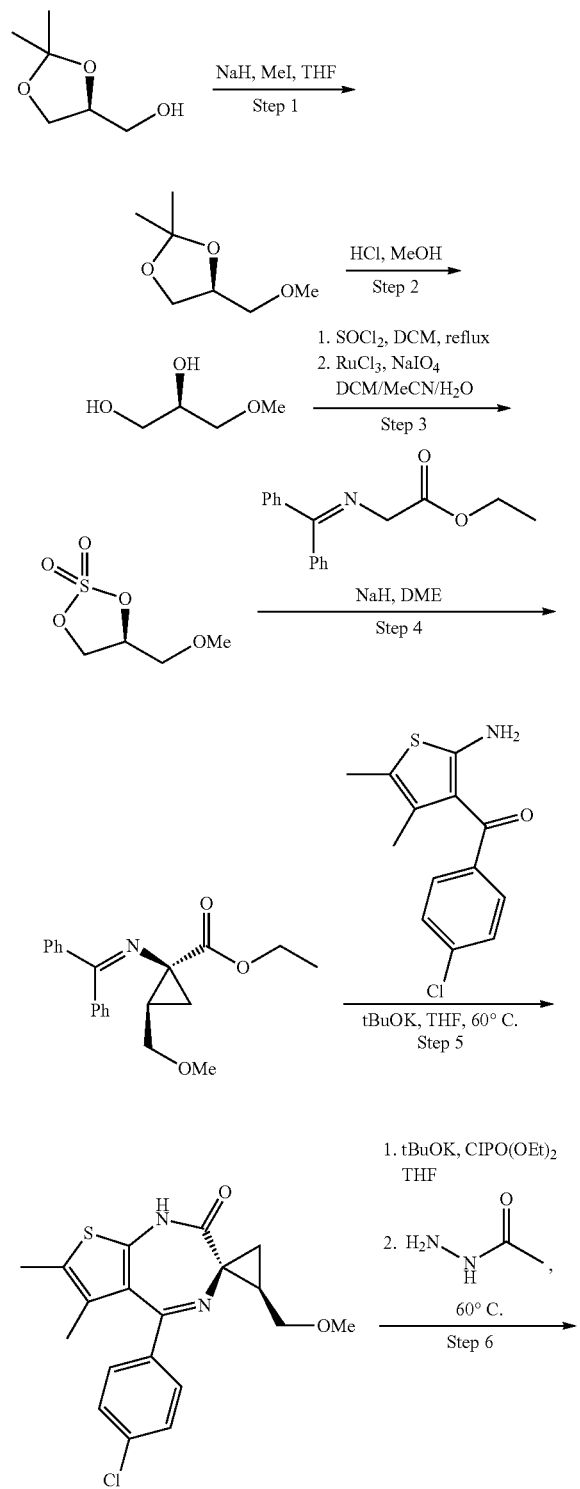

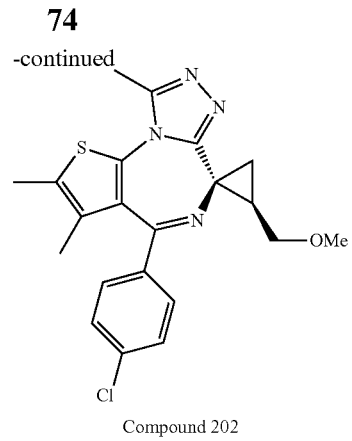

Compound 202

(S)-4-(Methoxymethyl)-2,2-dimethyl-1,3-dioxolane (Step 1)

To a solution of (S)-(2,2-dimethyl-1,3-dioxolan-4-yl)methanol (9.8 g, 74.2 mmol) in anhydrous THF (150 mL) at 0° C. was added sodium hydride (60% in mineral oil) (3.26 g, 82 mmol) in 4 portions over 5 min (caution: gas evolution). The reaction was stirred for an additional 15 min at 0° C., then iodomethane (5.09 mL, 82 mmol) was added and the reaction was warmed to rt. After approximately 1 h at rt, the reaction was diluted with diethyl ether (100 mL), filtered and concentrated to 15-20 mL under vacuum. The yellow liquid was used in the next step without purification.

(R)-3-Methoxypropane-1,2-diol (Step 2)

To a solution of crude (S)-4-(methoxymethyl)-2,2-dimethyl-1,3-dioxolane (10.55 g, 72.2 mmol from step 1) in MeOH (100 mL) was added hydrochloric acid (2 M in diethylether) (18.05 mL, 36.1 mmol) at rt to give a turbid yellow solution. After 1 h, extra hydrochloric acid (2 M in diethylether) (18.05 mL, 36.1 mmol) was added, and the reaction was stirred for an additional 1 h at rt. The reaction was then concentrated under vacuum. Traces of hydrochloric acid were removed by co-evaporation with DCM (repeated twice). The brown liquid was used in the next step without purification.

(S)-4-(Methoxymethyl)-1,3,2-dioxathiolane 2,2-dioxide (Step 3)

To a solution of crude (R)-3-methoxypropane-1,2-diol (7.66 g, 72.2 mmol) in DCM (100 mL) was slowly (~10 min) added thionyl chloride (6.32 mL, 87 mmol) at rt. When the addition was completed, the dark brown solution was heated to reflux for 1 h before concentrating it to ~10-20 mL under vacuum. Then, the cyclic sulfite was dissolved in DCM (80 mL) and acetonitrile (80 mL) and cooled to 0° C. Ruthenium (III) chloride (0.075 g, 0.361 mmol) and sodium periodate (23.16 g, 108 mmol) were added followed by water (100 mL). The biphasic reaction was vigorously stirred at 0° C. for 1 h. The reaction was finally diluted with diethyl ether (600 mL) and the product was sequentially washed with water, a saturated solution of sodium bicarbonate (repeated twice) and brine. The organic layer was dried over $Na_2SO_4$, filtered through a pad of silica gel (the pad was rinsed with diethyl ether) and concentrated under vacuum. The turbid liquid was used in the next step without purification.

(1S,2R)-ethyl 1-((Diphenylmethylene)amino)-2-(methoxymethyl)cyclopropanecarboxylate (Step 4)

To a suspension of sodium hydride (60% in mineral oil) (7.14 g, 178 mmol) in dimethoxyethane (200 mL) was slowly (over 20 min) added a solution of crude ethyl 2-(diphenylmethyleneamino) acetate (19.08 g, 71.4 mmol) and (S)-4-(methoxymethyl)-1,3,2-dioxathiolane 2,2-dioxide (12 g, 71.4 mmol) in dimethoxyethane (150 mL) at rt (Caution: gas evolution). Upon addition, the reaction was stirred at rt for 1 h then at 50° C. for 30 min. The mixture was then cooled to rt, and absolute ethanol (3 mL) (to quench the excess of sodium hydride) and silica gel (100 mL) were sequentially added. The silica gel was dried under vacuum, packed and purified by flash chromatography (EtOAc/hexane/toluene 1:5:4) to give (1S,2R)-ethyl 1-((diphenylmethylene)amino)-2-(methoxymethyl)cyclopropanecarboxylate (12.88 g). LRMS (M+H)$^+$: 338 m/z.

(1S,2R)-5'-(4-Chlorophenyl)-2-(methoxymethyl)-6',7'-dimethylspiro[cyclopropane-1,3'-thieno[2,3-e][1,4]diazepin]-2'(1'H)-one (Step 5)

To a solution of (2-amino-4,5-dimethylthiophen-3-yl)(4-chlorophenyl)methanone (7.09 g, 26.7 mmol) and (1S,2R)-ethyl 1-((diphenylmethylene)amino)-2-(methoxymethyl)cyclopropanecarboxylate (6 g, 17.78 mmol) in anhydrous THF (100 mL) was slowly (over 5 min) added a solution of potassium tert-butoxide (1 M in THF) at rt. The reaction was heated to 60° C. for approximately 20 h before acetic acid (10.68 g, 178 mmol) and absolute ethanol (20 mL) were added at 60° C. THF was distilled off, and the reaction was heated to reflux for 3 h. The reaction was cooled to rt before silica gel was added, and the solvent was removed under vacuum. The dry silica gel was packed and the product was purified by flash chromatography (EtOAc/hexane 1:19 to 6:14) to give (1S,2R)-5'-(4-chlorophenyl)-2-(methoxymethyl)-6',7'-dimethylspiro[cyclopropane-1,3'-thieno[2,3-e][1,4]diazepin]-2'(1'H)-one a solid (3.7 g). LRMS (M+H)$^+$: 375 m/z.

(1S,2R)-4'-(4-Chlorophenyl)-2-(methoxymethyl)-2',3',9'-trimethylspiro-[cyclopropane-1,6'-thieno[3,2-f][1,2,4]triazolo[4,3-a][1,4]diazepin] (Compound 202; Step 6)

To a solution of (1S,2R)-5'-(4-chlorophenyl)-2-(methoxymethyl)-6',7'-dimethylspiro-[cyclopropane-1,3'-thieno[2,3-e][1,4]diazepin]-2'(1'H)-one (3.7, 9.87 mmol) in anhydrous THF (200 mL) at −78° C. was slowly added a solution of potassium tert-butoxide (12.34 mL, 12.34 mmol). The resulting dark brown solution was warmed to rt and stirred for 30 min. The reaction was cooled to −78° C. before diethyl phosphorochloridate (2.85 mL, 19.74 mmol) was slowly added. Once the addition was completed, the reaction was warmed to rt for 60 to 90 min before acetohydrazide (2.193 mg, 29.6 mmol) was added. The reaction was then heated to 60° C. for 2 h before MeOH (5 mL) and silica gel were sequentially added. The solvent was removed under vacuum, the dry silica gel was packed, and the product was purified by flash chromatography (EtOAc/hexane 3:7 to 100:0) to give (1S,2R)-4'-(4-chlorophenyl)-2-(methoxymethyl)-2',3',9'-trimethylspiro[cyclopropane-1,6'-thieno[3,2-f][1,2,4]triazolo[4,3-a][1,4]diazepine] as a solid (3.54 g). LRMS (M+H)$^+$: 413 m/z. $^1$H NMR (two conformers detected in ~1:1 ratio) (400 MHz, DMSO-d$_6$) δ 7.42-7.55 (m, 4H), 3.82 (dd, J=7.32, 10.99 Hz, 0.5H), 3.71 (dd, J=6.41, 11.22 Hz, 0.5H), 3.39 (s, 1.5H), 3.21 (dd, J=6.29, 10.87 Hz, 0.5H), 3.04 (dd, J=7.67, 10.87 Hz, 0.5H), 2.97 (s, 1.5H), 2.60 (s, 3H), 2.39 (s, 1.5H), 2.38 (s, 1.5H), 2.16-2.27 (m, 0.5H), 2.05 (dd, J=5.26, 9.38 Hz, 0.5H), 1.58 (s, 1.5H), 1.54 (s, 1.5H), 1.43-1.51 (m, 0.5H), 1.33-1.40 (m, 0.5H), 1.03 (dd, J=5.38, 9.27 Hz, 0.5H), 0.61 (t, J=6.07 Hz, 0.5H).

EXAMPLE 15

Synthesis of ((1S,2R)-4'-(4-chlorophenyl)-2',3',9'-trimethylspiro[cyclopropane-1,6'-thieno[3,2-f][1,2,4]triazolo[4,3-a][1,4]diazepin]-2-yl)methanol (Compound 203)

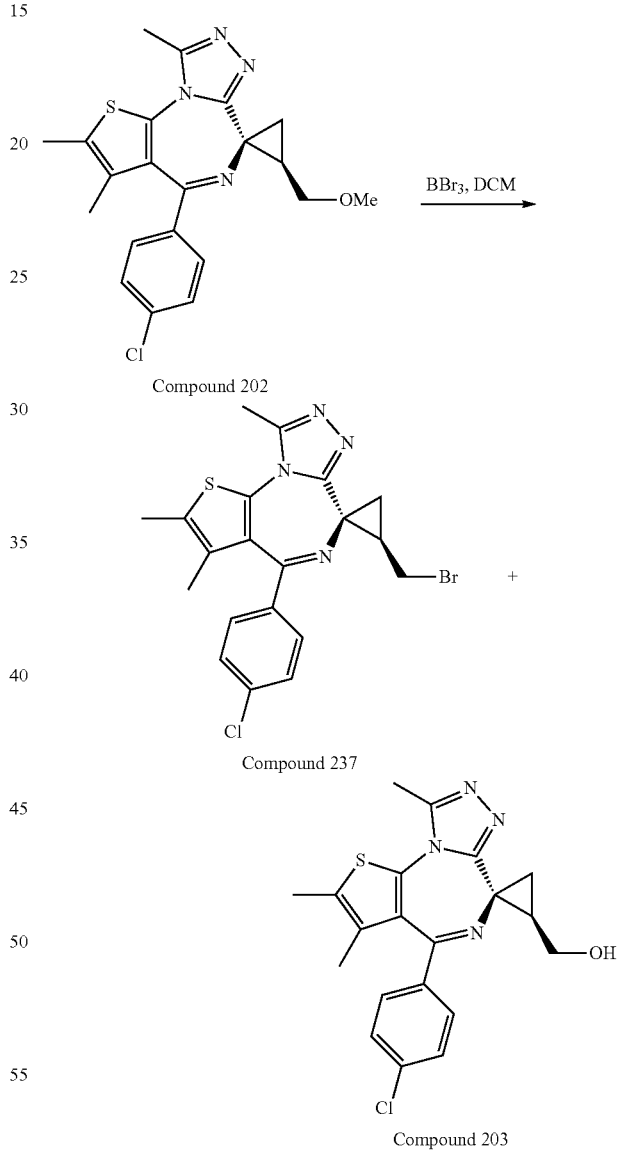

Compound 202

Compound 237

Compound 203

((1S,2R)-4'-(4-Chlorophenyl)-2',3',9'-trimethylspiro[cyclopropane-1,6'-thieno[3,2-f][1,2,4]triazolo[4,3-a][1,4]diazepin]-2-yl)methanol (Compound 203)

To a solution of (1S,2R)-4'-(4-chlorophenyl)-2-(methoxymethyl)-2',3',9'-trimethylspiro[cyclopropane-1,6'-thieno[3,2-f][1,2,4]triazolo[4,3-a][1,4]diazepine] (2.35 g, 5.69 mmol) in DCM (70 mL) at −78° C. was added a solution of boron tribromide (1M in DCM) (Compound 202; 17.07 mmol). The reaction was warmed to rt for 30 min before MeOH was added followed by sat. aq. NaHCO$_3$. The product was extracted with DCM (repeated 4 times), dried over a cotton plug and concentrated to dryness under vacuum. The residue was purified by flash chromatography (MeOH/DCM 0.5:99.5 to 5:95) to give ((1S,2R)-4'-(4-chlorophenyl)-2',3',9'-trimethylspiro[cyclopropane-1,6'-thieno[3,2-f][1,2,4]triazolo[4,3-a][1,4]diazepin]-2-yl)methanol (Compound 203) (1.9 g) as a white solid and (1S,2R)-2-(bromomethyl)-4'-(4-chlorophenyl)-2',3',9'-trimethylspiro[cyclopropane-1,6'-thieno[3,2-f][1,2,4]triazolo[4,3-a][1,4]diazepine] (Compound 237) (449 mg) as a side product. LRMS (M+H)$^+$: 399 m/z. $^1$H NMR (two conformers detected in ~1:1 ratio) (400 MHz, DMSO-d$_6$) δ 7.41-7.53 (m, 4H), 4.64 (t, J=5.72 Hz, 0.5H), 4.51 (t, J=5.38 Hz, 0.5H), 3.95 (quin, J=6.20 Hz, 0.5H), 3.69 (quin, J=6.20 Hz, 0.5H), 3.10-3.18 (m, 0.5H), 3.01-3.09 (m, 0.5H), 2.60 (s, 3H), 2.39 (s, 1.5H), 2.38 (s, 1.5H), 2.14-2.23 (m, 0.5H), 1.96-2.04 (m, 0.5H), 1.57 (s, 1.5H), 1.55 (s, 1.5H), 1.32-1.37 (m, 0.5H), 1.25-1.32 (m, 0.5H), 0.96 (dd, J=5.26, 9.16 Hz, 0.5H), 0.58 (t, J=6.20 Hz, 0.5H).

EXAMPLE 16

Synthesis of (1S,2R)-4'-(4-chlorophenyl)-N-ethyl-2',3',9'-trimethylspiro[cyclopropane-1,6'-thieno[3,2-f][1,2,4]triazolo[4,3-a][1,4]diazepine]-2-carboxamide (Compound 204)

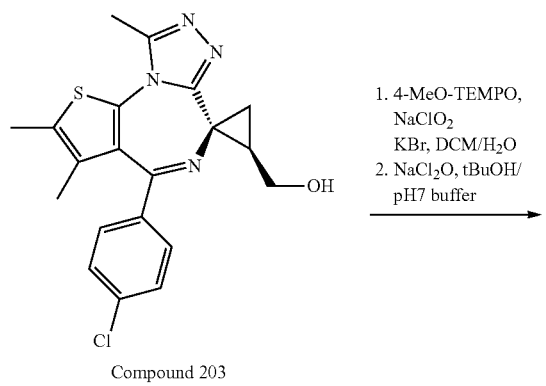

Compound 203

1. 4-MeO-TEMPO, NaClO$_2$, KBr, DCM/H$_2$O
2. NaCl$_2$O, tBuOH/pH7 buffer

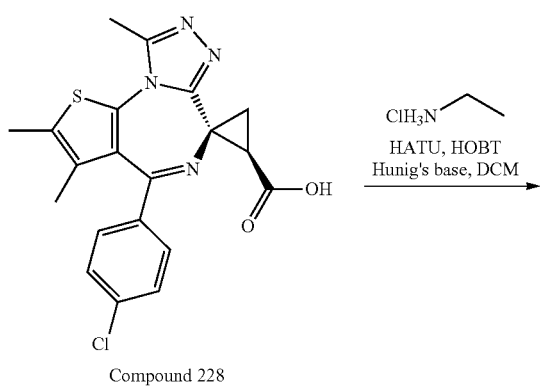

Compound 228

ClH$_3$N⁀

HATU, HOBT
Hunig's base, DCM

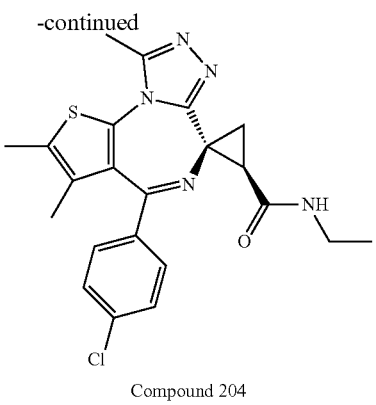

Compound 204

(1S,2R)-4'-(4-Chlorophenyl)-2',3',9'-trimethylspiro[cyclopropane-1,6'-thieno[3,2-f][1,2,4]triazolo[4,3-a][1,4]diazepine]-2-carbaldehyde (Step 1)

A solution of ((1S,2R)-4'-(4-chlorophenyl)-2',3',9'-trimethylspiro[cyclopropane-1,6'-thieno[3,2-f][1,2,4]triazolo[4,3-a][1,4]diazepine]-2-yl)methanol (300 mg, 0.752 mmol) in DCM (5 mL), a solution of 4-methoxy TEMPO (0.0135M in DCM) (1 mL, 0.0135 mmol), a solution of Aliquat 336 (0.074M in DCM) (0.5 mL, 0.037 mmol) and a solution of potassium bromide (0.25M in water) (0.3 mL, 0.075 mmol) were mixed and cooled to 0° C. before a solution of sodium hypochlorite (0.35M in water; buffered with NaHCO$_3$ to pH~8.6) was slowly added. After 30 min of vigorous stirring at 0° C., the aqueous layer was extracted with DCM. 2-Methyl-2-butene (0.5 mL) was added to the organic layer, before it was concentrated to dryness. The residue was used in the next step without purification. LRMS (M+H)$^+$: 397 m/z.

(1S,2R)-4'-(4-Chlorophenyl)-2',3',9'-trimethylspiro[cyclopropane-1,6'-thieno[3,2-f][1,2,4]triazolo[4,3-a][1,4]diazepine]-2-carboxylic acid (Compound 228; Step 2)

To a solution of crude (1S,2R)-4'-(4-chlorophenyl)-2',3',9'-trimethylspiro[cyclopropane-1,6'-thieno[3,2-f][1,2,4]triazolo[4,3-a][1,4]diazepine]-2-carbaldehyde (298 mg, 0.752 mmol) in t-BuOH (5 mL) was added 2-methylbut-2-ene (1055 mg, 15.04 mmol) and a pH 7 buffer solution (5 mL). Then sodium chlorite was added at rt, and the biphasic reaction was vigorously stirred for 3.5 h. When the starting material was entirely consumed, sat. aq. NH$_4$Cl was added, and the product was extracted with DCM/MeOH (19:1) (repeated 3 times). The organic layers were combined, dried over Na$_2$SO$_4$, filtered and concentrated to dryness. The residue was used in the next step without purification. LRMS (M+H)$^+$: 413 m/z.

(1S,2R)-4'-(4-Chlorophenyl)-N-ethyl-2',3',9'-trimethylspiro[cyclopropane-1,6'-thieno[3,2-f][1,2,4]triazolo[4,3-a][1,4]diazepine]-2-carboxamide (Compound 204; Step 3)

To a solution of crude (1S,2R)-4'-(4-chlorophenyl)-2',3',9'-trimethylspiro[cyclopropane-1,6'-thieno[3,2-f][1,2,4]triazolo[4,3-a][1,4]diazepine]-2-carboxylic acid (Compound 228; 0.09 g, 0.218 mmol) in DCM (2.4 mL) was added N,N-diisopropylethylamine (0.190 ml, 1.090 mmol), ethylamine hydrochloride (0.071 g, 0.872 mmol) and HOBt (0.017 g, 0.109 mmol). The mixture was stirred for 10 min at rt (still heterogeneous) before HATU (0.166 g, 0.436 mmol) was added, still at rt. After 20 min, the reaction was filtered on a pad of silica gel. The silica gel was successively rinsed with EtOAc/hexane (5:5) to (10:0) and DCM/MeOH (9:1). The filtrate was concentrated to dryness, and the residue was purified by reverse phase chromatography to give the desired product as an off-white solid (34 mg). LRMS (M+H)+: 440 m/z. $^1$H NMR (major conformer reported only) (400 MHz, DMSO-$d_6$) δ 8.36 (br. s., 1H), 7.37-7.54 (m, 4H), 2.89-3.01 (m, 1H), 2.69-2.82 (m, 1H), 2.62 (s, 3H), 2.36 (s, 3H), 2.07 (dd, J=5.15, 8.81 Hz, 1H), 1.92 (t, J=6.40 Hz, 1H), 1.78 (t, J=8.00 Hz, 1H), 1.43 (s, 3H), 0.84 (t, J=7.10 Hz, 3H).

EXAMPLE 17

(1S,2R)-4'-(4-Chlorophenyl)-2',3',9'-trimethylspiro [cyclo-propane-1,6'-thieno[3,2-f][1,2,4]triazolo[4,3-a][1,4]diazepine]-2-carboxamide (Compound 205)

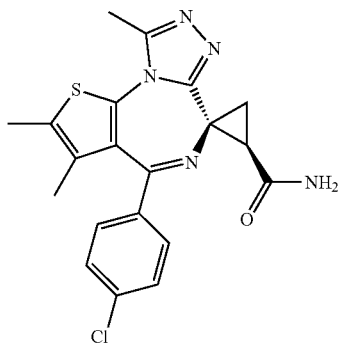 [SMILES: Cc1sc2c(c1C)C(c1ccc(Cl)cc1)=N[C@]1(C[C@H]1C(N)=O)c1nnc(C)n1-2]

A procedure analogous to that used for Compound 204 was followed, with the exception that ammonium chloride was used instead of ethylamine hydrochloride. LRMS (M+H)+: 412 m/z. $^1$H NMR (major conformer reported only) (400 MHz, DMSO-$d_6$) δ 7.38-7.54 (m, 4H), 6.83 (br. s., 1H), 6.69 (br. s., 1H), 2.62 (s, 3H), 2.35 (s, 3H), 2.06 (dd, J=5.04, 8.93 Hz, 1H), 1.93 (t, J=6.20 Hz, 1H), 1.81 (t, J=7.80 Hz, 1H), 1.48 (s, 3H).

EXAMPLE 18

((1S,2S)-4'-(4-Chlorophenyl)-2',3',9'-trimethylspiro [cyclo-propane-1,6'-thieno[3,2-f][1,2,4]triazolo[4,3-a][1,4]diazepin]-2-yl)methanamine (Compound 206)

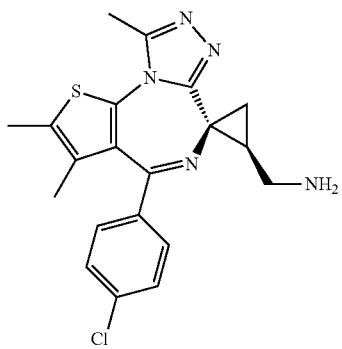 [SMILES: Cc1sc2c(c1C)C(c1ccc(Cl)cc1)=N[C@]1(C[C@H]1CN)c1nnc(C)n1-2]

To a solution of (1S,2R)-2-(bromomethyl)-4'-(4-chlorophenyl)-2',3',9'-trimethylspiro-[cyclopropane-1,6'-thieno[3,2-f][1,2,4]triazolo[4,3-a][1,4]diazepine](350 mg, 0.758 mmol) in DMF (4 mL) was added ammonium hydroxide (3 mL, 77 mmol) at rt. After 9 h at rt, silica gel was added, and the solvent was removed under vacuum. The dry silica gel was packed, and the product was purified by chromatography (Hexane/EtOAc 5:5 to 0:10 then DCM/MeOH 10:0 to 9:1). A second (EtOAc/toluene/MeOH 4:4:2) and a third chromatography were performed (2-propanol 100%) to give a tan solid (12 mg). LRMS (M+H)+: 398 m/z.

EXAMPLE 19

N-(((1S,2S)-4'-(4-Chlorophenyl)-2',3',9'-trimethyl-spiro[cyclopropane-1,6'-thieno[3,2-f][1,2,4]triazolo [4,3-a][1,4]diazepin]-2-yl)methyl)acetamide (Compound 207)

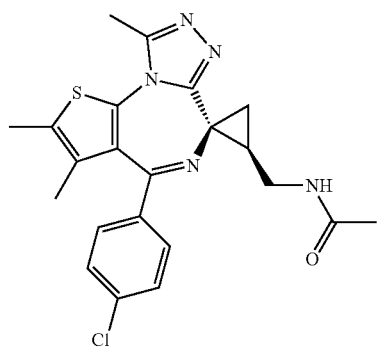 [SMILES: CC(=O)NC[C@@H]1C[C@]12N=C(c1ccc(Cl)cc1)c1c(sc(C)c1C)-n1c(C)nnc12]

To a solution of ((1S,2S)-4'-(4-chlorophenyl)-2',3',9'-trimethylspiro[cyclopropane-1,6'-thieno[3,2-f][1,2,4]triazolo[4, 3-a][1,4]diazepine]-2-yl)methanamine (Compound 206; 50 mg, 0.126 mmol) in DCM (2 mL) was added N,N-diisopropylethylamine (43.9 μl, 0.251 mmol). Once the reaction was cooled to 0° C., a solution of acetic anhydride in DCM (140 mg/mL) (14.23 μl, 0.151 mmol) was added. The reaction was stirred at 0° C. for 15 min before an aqueous solution of NaHCO$_3$(sat.) was added for the quench. The product was extracted with DCM (repeated 4 times). The organic layers were combined, dried over Na$_2$SO$_4$ and concentrated to dryness. The residue was purified by flash chromatography (DCM/MeOH 10:0 to 9:1) to give the desired product as an off-white solid (33 mg). LRMS (M+H)+: 440 m/z. $^1$H NMR (two conformers detected in ~1:1 ratio) (400 MHz, DMSO-$d_6$) δ 8.08 (t, J=5.15 Hz, 0.5H), 7.75 (t, J=4.92 Hz, 0.5H), 7.44-7.56 (m, 4H), 3.45-3.51 (m, 1H), 2.78-2.86 (m, 0.5H), 2.64-2.72 (m, 0.5H), 2.56-2.63 (m, 3H), 2.35-2.42 (m, 3H), 2.13-2.22 (m, 0.5H), 2.00 (dd, J=5.04, 8.93 Hz, 0.5H), 1.86 (s, 1.5H), 1.71 (s, 1.5), 1.58 (m, 1.5H), 1.57 (m, 1.5H), 1.22-1.37 (m, 1H), 0.99 (dd, J=5.26, 9.16 Hz, 0.5H), 0.58 (t, J=5.95 Hz, 0.5H).

EXAMPLE 20

N-(((1S,2S)-4'-(4-Chlorophenyl)-2',3',9'-trimethyl-spiro[cyclopropane-1,6'-thieno[3,2-f][1,2,4]triazolo [4,3-a][1,4]diazepin]-2-yl)methyl)ethanamine (Compound 208)

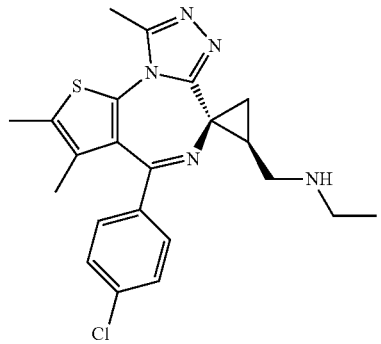 [SMILES: CCNC[C@@H]1C[C@]12N=C(c1ccc(Cl)cc1)c1c(sc(C)c1C)-n1c(C)nnc12]

To a solution of (1S,2R)-2-(bromomethyl)-4'-(4-chlorophenyl)-2',3',9'-trimethylspiro-[cyclopropane-1,6'-thieno[3,2-f][1,2,4]triazolo[4,3-a][1,4]diazepine](50 mg, 0.108 mmol) in anhydrous N,N-dimethylformamide (3 mL) were added ethanamine hydrochloride (221 mg, 2.71 mmol) and Hunig's base (473 μl, 2.71 mmol) at rt. After 4 days at rt, silica gel was added to the reaction, and the solvent was removed under vacuum. The dry silica gel was packed and the product was purified by chromatography (Hexane/EtOAc 5:5 to 0:10 then DCM/MeOH 10:0 to 9:1). A second chromatography was performed (2-propanol 100% then DCM/MeOH 9:1) to give a tan solid (32 mg). LRMS (M+H)+: 426 m/z.

EXAMPLE 21

Synthesis of (1R,2S)-4'-(4-chlorophenyl)-2-(methoxymethyl)-2',3',9'-trimethylspiro[cyclopropane-1,6'-thieno[3,2-f][1,2,4]triazolo[4,3-a][1,4]diazepine] (Compound 209)

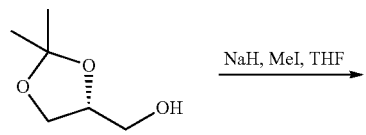

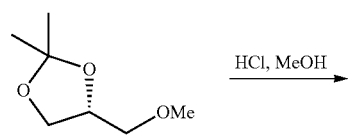

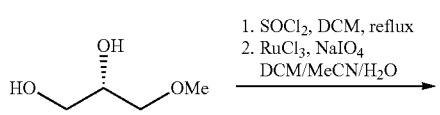

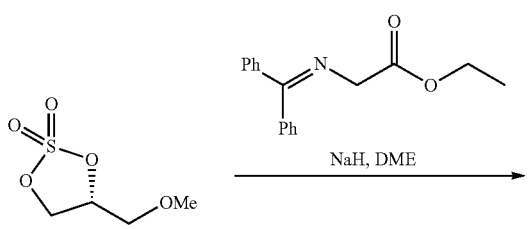

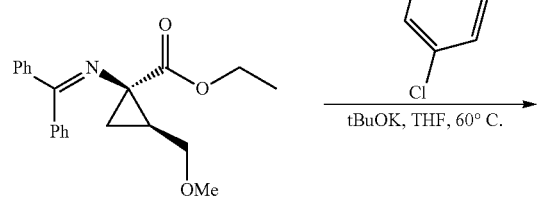

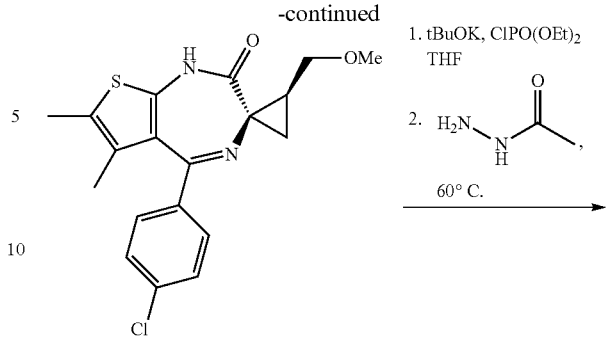

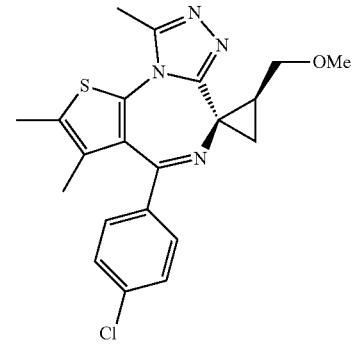

Compound 209

The above employed synthesis scheme was identical to that set forth for Compound 202, except that (R)-(2,2-dimethyl-1,3-dioxolan-4-yl)methanol was used as starting material and the indicated enantiomers were produced at each step. LRMS (M+H)+: 413 m/z. ¹H NMR (two conformers detected in ~1:1 ratio) (400 MHz, DMSO-$d_6$) δ 7.38-7.56 (m, 4H), 3.82 (dd, J=7.32, 10.76 Hz, 0.5H), 3.71 (dd, J=6.87, 10.99 Hz, 0.5H), 3.39 (s, 1.5H), 3.21 (dd, J=6.41, 10.76 Hz, 0.5H), 3.04 (dd, J=7.44, 10.87 Hz, 0.5H), 2.96 (s, 1.5H), 2.60 (s, 3H), 2.39 (s, 1.5H), 2.38 (s, 1.5H), 2.16-2.26 (m, 0.5H), 2.05 (dd, J=5.26, 9.61 Hz, 0.5H), 1.58 (s, 1.5H), 1.54 (s, 1.5H), 1.43-1.52 (m, 0.5H), 1.33-1.39 (m, 0.5H), 1.03 (dd, J=5.26, 9.38 Hz, 0.5H), 0.60 (t, J=6.07 Hz, 0.5H).

EXAMPLE 22

((1R,2S)-4'-(4-Chlorophenyl)-2',3',9'-trimethylspiro[cyclo-propane-1,6'-thieno[3,2-f][1,2,4]triazolo[4,3-a][1,4]diazepin]-2-yl)methanol (Compound 210)

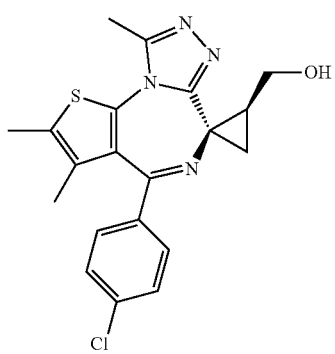 [SMILES: Cc1sc2c(c1C)C(c1ccc(Cl)cc1)=N[C@@]1(C[C@@H]1CO)c1nnc(C)n1-2]

A procedure analogous to that set forth for Compound 203 was followed, with the exception that (1R,2S)-4'-(4-chlorophenyl)-2-(methoxymethyl)-2',3',9'-trimethylspiro[cyclopropane-1,6'-thieno[3,2-f][1,2,4]triazolo[4,3-a][1,4]diazepine](Compound 209) was used as starting material. LRMS (M+H)⁺: 399 m/z. ¹H NMR (two conformers detected in ~1:1 ratio) (400 MHz, DMSO-d₆) δ 7.42-7.52 (m, 4H), 4.63 (t, J=5.40 Hz, 0.5H), 4.50 (t, J=5.38 Hz, 0.5H), 3.95 (quin, J=6.40 Hz, 0.5H), 3.68 (quin, J=5.80 Hz, 0.5H), 3.14 (td, J=5.64, 11.39 Hz, 0.5H), 3.02-3.09 (m, 0.5H), 2.59 (s, 3H), 2.38 (s, 1.5H), 2.37 (s, 1.5H), 2.14-2.23 (m, 0.5H), 2.00 (dd, J=5.26, 9.16 Hz, 0.5H), 1.56 (s, 1.5H), 1.54 (d, J=0.69 Hz, 1.5H), 1.33 (dd, J=5.04, 6.41 Hz, 0.5H), 1.21-1.30 (m, 0.5H), 0.95 (dd, J=5.04, 9.00 Hz, 0.5H), 0.57 (t, J=6.00 Hz, 0.5H).

EXAMPLE 23

Synthesis of (1R,2S)-4'-(4-chlorophenyl)-N-ethyl-2',3',9'-trimethylspiro[cyclopropane-1,6'-thieno[3,2-f][1,2,4]triazolo[4,3-a][1,4]diazepine]-2-carboxamide (Compound 211)

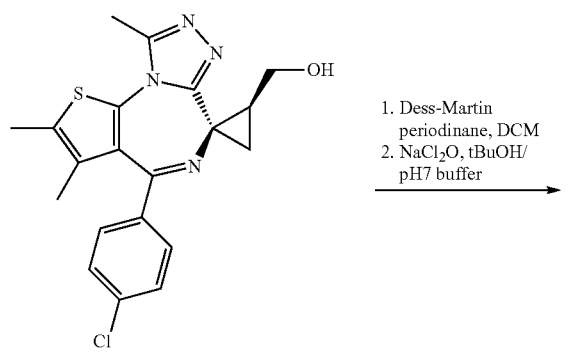

Compound 210

1. Dess-Martin periodinane, DCM
2. NaCl₂O, tBuOH/pH7 buffer

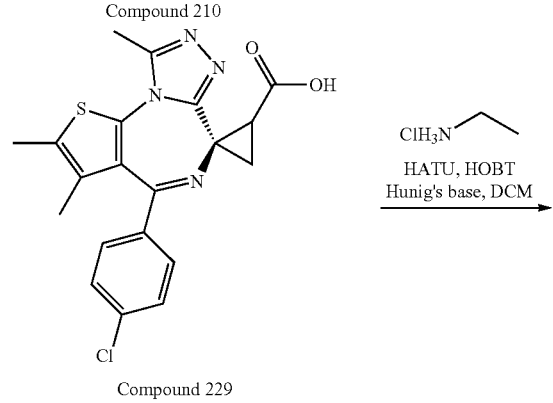

Compound 229

ClH₃N⟋

HATU, HOBT
Hunig's base, DCM

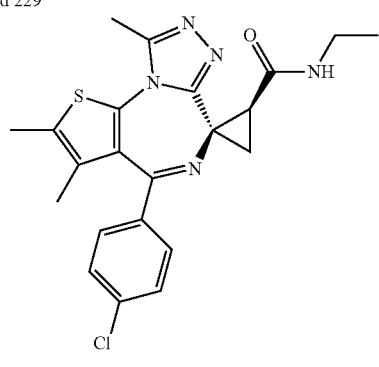

Compound 211

+

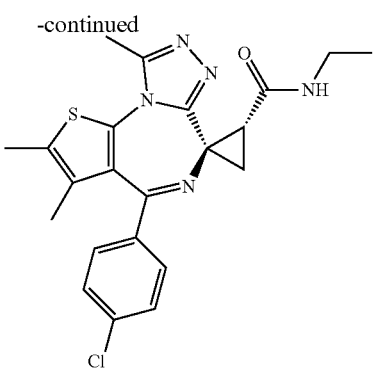

Compound 212

(1R)-4'-(4-Chlorophenyl)-2',3',9'-trimethylspiro[cyclopropane-1,6'-thieno[3,2-f][1,2,4]triazolo[4,3-a][1,4]diazepine]-2-carbaldehyde (Step 1)

To a solution of ((1S,2R)-4'-(4-chlorophenyl)-2',3',9'-trimethylspiro[cyclopropane-1,6'-thieno[3,2-f][1,2,4]triazolo[4,3-a][1,4]diazepine]-2-yl)methanol (Compound 210; 75 mg, 0.188 mmol) in DCM (2 mL) at 0° C. was added Dess-Martin periodinane (96 mg, 0.226 mmol). After 1 h at 0° C., extra Dess-Martin periodinane (96 mg, 0.226 mmol) was added, and the reaction was warmed to rt for 2 h. Then the reaction was diluted with diethylether and filtered. The filtrate was concentrated to dryness under vacuum, and the residue was used without purification in the next step. LRMS (M+H)⁺: 397 m/z.

(1R)-4'-(4-Chlorophenyl)-2',3',9'-trimethylspiro[cyclopropane-1,6'-thieno[3,2-f][1,2,4]triazolo[4,3-a][1,4]diazepine]-2-carboxylic acid (Compound 229; Step 2)

A procedure analogous to that set forth for Compound 228 was followed, with the exception that (1R)-4'-(4-chlorophenyl)-2',3',9'-trimethylspiro[cyclopropane-1,6'-thieno[3,2-f][1,2,4]triazolo[4,3-a][1,4]diazepine]-2-carbaldehyde was used as starting material. LRMS (M+H)⁺: 413 m/z.

(1R,2S)-4'-(4-Chlorophenyl)-N-ethyl-2',3',9'-trimethylspiro[cyclopropane-1,6'-thieno[3,2-f][1,2,4]triazolo[4,3-a][1,4]diazepine]-2-carboxamide (Compound 211; Step 3)

A procedure analogous to that set forth for Compound 204 was followed, with the exception that (1R)-4'-(4-chlorophenyl)-2',3',9'-trimethylspiro[cyclopropane-1,6'-thieno[3,2-f][1,2,4]triazole-[4,3-a][1,4]diazepine]-2-carboxylic acid was used as starting material. The title compound was obtained after purification by reverse phase chromatography to separate the two diastereoisomers. LRMS (M+H)⁺: 440 m/z. ¹H NMR (major conformer reported only) (400 MHz, DMSO-d₆) δ 8.36 (t, J=5.15 Hz, 1H), 7.39-7.53 (m, 4H), 2.88-3.00 (m, 1H), 2.68-2.80 (m, 1H), 2.61 (s, 3H), 2.35 (s, 3H), 2.07 (dd, J=5.04, 9.16 Hz, 1H), 1.92 (dd, J=5.15, 6.98 Hz, 1H), 1.78 (dd, J=7.10, 9.16 Hz, 1H), 1.42 (s, 3H), 0.84 (t, J=7.40 Hz, 3H).

EXAMPLE 24

(1R,2R)-4'-(4-Chlorophenyl)-N-ethyl-2',3',9'-trimethylspiro-[cyclopropane-1,6'-thieno[3,2-f][1,2,4]triazolo[4,3-a][1,4]diazepine]-2-carboxamide (Compound 212)

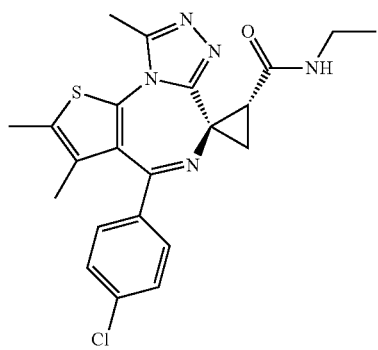 [SMILES: CCNC(=O)[C@@H]1C[C@@]12N=C(c1ccc(Cl)cc1)c1c(sc(C)c1C)-n1c(C)nnc12]

The same procedure as that set forth for Compound 211 was followed. The title compound was obtained after purification of the reaction by reverse phase chromatography. LRMS (M+H)+: 440 m/z. ¹H NMR (major conformer reported only) (400 MHz, DMSO-d₆) δ 7.46-7.54 (m, 4H), 7.42 (t, J=5.26 Hz, 1H), 2.71-2.88 (m, 2H), 2.53 (s, 3H), 2.38 (s, 3H), 2.11 (dd, J=4.81, 6.64 Hz, 1H), 1.77 (dd, J=4.81, 8.93 Hz, 1H), 1.70 (dd, J=6.41, 8.93 Hz, 1H), 1.63 (s, 3H), 0.82 (t, J=7.21 Hz, 3H)

EXAMPLE 25

Synthesis of 4'-(4-chlorophenyl)-3',9'-dimethylspiro[cyclopropane-1,6'-isothiazolo[4,5-f][1,2,4]triazolo[4,3-a][1,4]diazepine] (Compound 213)

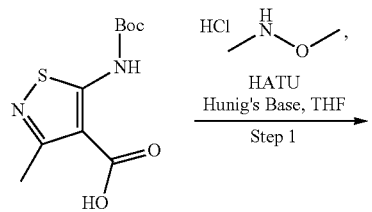

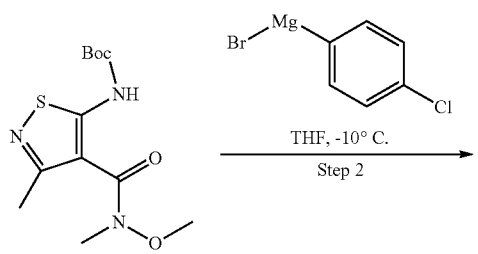

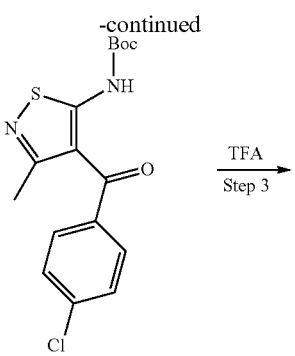

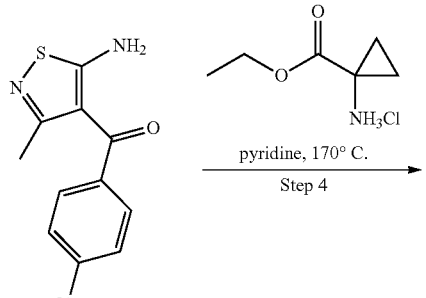

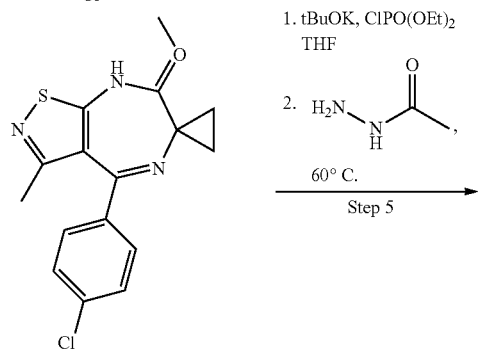

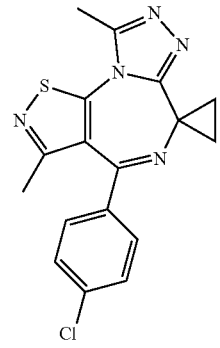

Compound 213 tert-Butyl (4-(methoxy(methyl)carbamoyl)-3-methylisothiazol-5-yl)carbamate (Step 1)

To a solution of 5-(tert-butoxycarbonylamino)-3-methylisothiazole-4-carboxylic acid (2.10 g, 8.13 mmol) in THF (45 mL) at 0° C. were added HATU (3.70 g, 9.76 mmol) and Hunig's base (3.15 g, 24.4 mmol). After a period of 5 min, N,O-dimethylhydroxylamine hydrochloride (1.03 g, 10.6 mmol) was added to the previous mixture. After a period of 1.5 h at rt, the resulting mixture was evaporated under reduced pressure and purified by flash chromatography (EtOAc/hexane 1:9 to 10:0) to give tert-butyl 4-(methoxy(methyl)carbamoyl)-3-methylisothiazol-5-ylcarbamate as an oil (1.60 g). LRMS (M+H)+: 302 m/z.

tert-Butyl (4-(4-chlorobenzoyl)-3-methylisothiazol-5-yl)carbamate (Step 2)

To a solution of tert-butyl 4-(methoxy(methyl)carbamoyl)-3-methylisothiazol-5-ylcarbamate (1.20 g, 3.98 mmol) in THF (30 mL) at −10° C. was added a solution of (4-chlorophenyl)magnesium bromide (1 M in diethylether) (11.95 mL, 11.95 mmol). After a period of 15 min, additional Grignard reagent was added (11.95 mL). After a period of 30 min, the reaction mixture was quenched with saturated ammonium chloride and EtOAc. The organic phase was separated, dried over Na₂SO₄, filtered and evaporated under reduced pressure. The resulting mixture was purified by flash chromatography (EtOAc/hexane 0:10 to 4:6) to give tert-butyl 4-(4-chlorobenzoyl)-3-methylisothiazol-5-ylcarbamate as an oil (1.1 g). LRMS (M+H)+: 353 m/z.

(5-Amino-3-methylisothiazol-4-yl)(4-chlorophenyl)methanone (Step 3)

To tert-butyl 4-(4-chlorobenzoyl)-3-methylisothiazol-5-ylcarbamate (2.80 g, 7.94 mmol) was added an excess of TFA (20 mL). After a period of 15 min at reflux, the reaction mixture was evaporated under reduced pressure to give (5-amino-3-methylisothiazol-4-yl)(4-chlorophenyl)methanone as a white solid (1.50 g).

4'-(4-Chlorophenyl)-3'-methylspiro[cyclopropane-1,6'-isothiazolo[5,4-e][1,4]diazepin]-7'(8'H)-one (Step 4)

A mixture of (5-amino-3-methylisothiazol-4-yl)(4-chlorophenyl)methanone (0.19 g, 0.75 mmol) and ethyl 1-aminocyclopropanecarboxylate hydrochloride (0.19 g, 1.13 mmol) in pyridine (1 mL) was heated at 170° C. for 18 h. The reaction mixture was then evaporated, extracted with water, dried over Na₂SO₄, filtered and evaporated. The crude product was purified by flash chromatography (EtOAc/hexane 0:10 to 5:5) to give 4'-(4-chlorophenyl)-3'-methylspiro[cyclopropane-1,6'-isothiazolo[5,4-e][1,4]diazepin]-7'(8'H)-one (35 mg).

4'-(4-Chlorophenyl)-3',9'-dimethylspiro[cyclopropane-1,6'-isothiazolo[4,5-f][1,2,4]triazolo[4,3-a][1,4] diazepine] (Compound 213; Step 5)

A procedure analogous to that set forth for Compound 202 was followed, with the exception that 4'-(4-chlorophenyl)-3'-methylspiro[cyclopropane-1,6'-isothiazolo[5,4-e][1,4]diazepin]-7'(8'H)-one was used as starting material. LRMS (M+H)+: 356 m/z. ¹H NMR (400 MHz, DMSO-d₆) δ 7.25-7.65 (m, 4H), 2.62 (br. s., 3H), 1.91 (s, 3H), 1.85-1.89 (m, 2H), 1.78-1.82 (m, 2H).

EXAMPLE 26

Synthesis of 4-(4-chlorophenyl)-2,3,6,6,9-pentamethyl-6H-thieno[3,2-f][1,2,4]triazolo[4,3-a][1,4]diazepine (Compound 214)

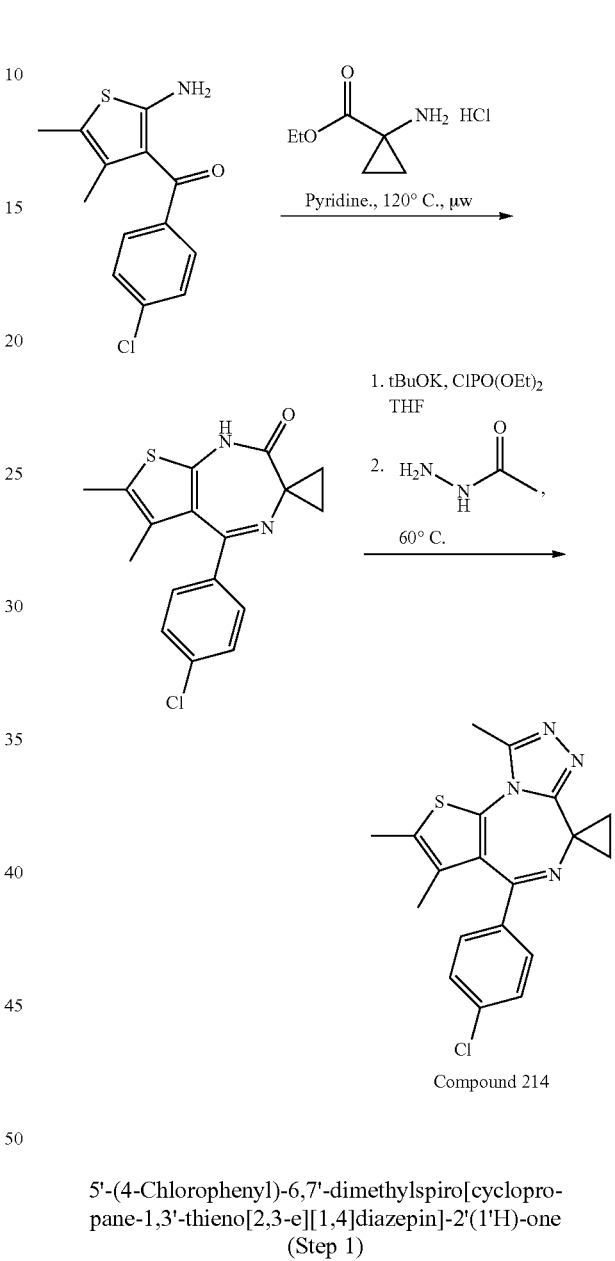

Compound 214

5'-(4-Chlorophenyl)-6',7'-dimethylspiro[cyclopropane-1,3'-thieno[2,3-e][1,4]diazepin]-2'(1'H)-one (Step 1)

A microwave vial was charged with (2-amino-4,5-dimethylthiophen-3-yl)(4-chlorophenyl)methanone (1.605 g, 6.04 mmol), ethyl 1-aminocyclo-propanecarboxylate hydrochloride (1 g, 6.04 mmol), and a stir bar. Pyridine (6 mL, 1.0 M) was added, and the mixture was stirred in the microwave at 120° C. for 24 h. The reaction mixture was purified by flash chromatography (hexane/EtOAc) and triturated from DMF with water to give 5'-(4-chlorophenyl)-6',7'-dimethylspiro[cyclopropane-1,3'-thieno[2,3-e][1,4]diazepin]-2'(1'H)-one as a brown amorphous solid (354 mg). LRMS (M+H)+: 331 m/z.

4'-(4-Chlorophenyl)-2',3',9'-trimethylspiro[cyclopropane-1,6'-thieno[3,2-f][1,2,4]triazolo[4,3-a][1,4]diazepine] (Compound 214; Step 2)

A procedure analogous to that set forth for Compound 202 was followed, with the exception that 5'-(4-chlorophenyl)-6',7'-dimethylspiro[cyclopropane-1,3'-thieno[2,3-e][1,4]diazepin]-2'(1'H)-one was used as starting material. LRMS (M+H)+: 369 m/z. $^1$H NMR (400 MHz, DMSO-$d_6$) δ 7.39-7.57 (m, 4H), 2.60 (s, 3H), 2.39 (s, 3H), 1.67-1.83 (m, 1H), 1.57 (s, 3H), 1.33-1.45 (m, 1H), 0.83 (t, J=8.47 Hz, 2H).

EXAMPLE 27

Synthesis of 4'-(4-chlorophenyl)-2,2',3',9'-tetramethyl-spiro[cyclopropane-1,6'-thieno[3,2-f][1,2,4]triazolo[4,3-a][1,4]diazepine] (Compound 215)

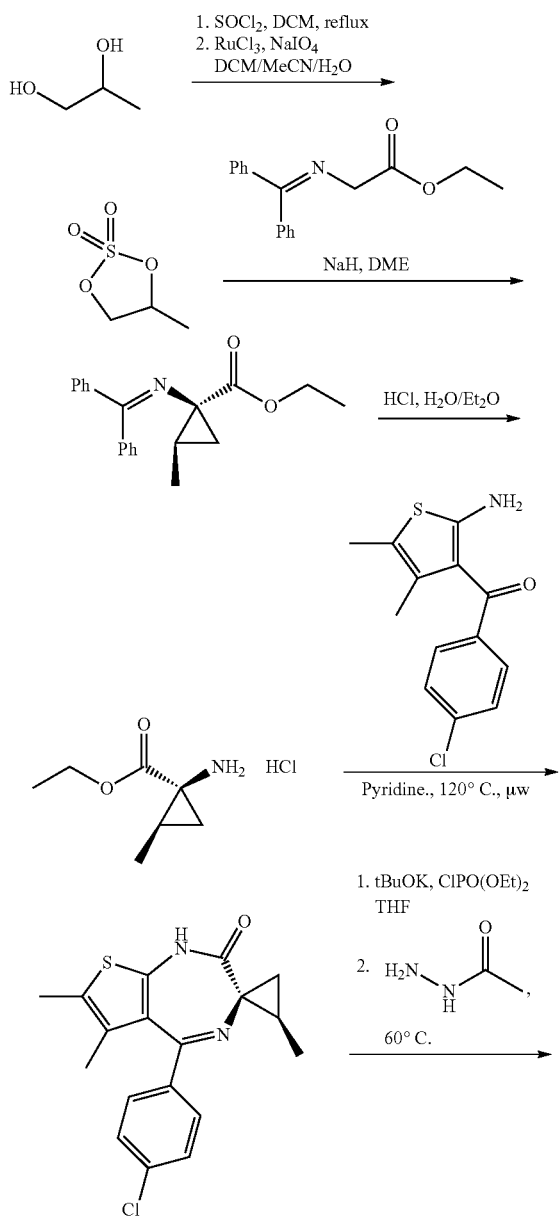

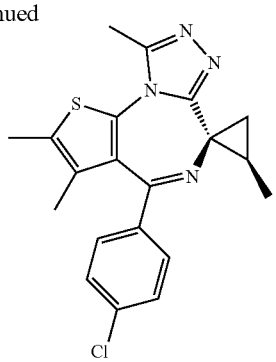

Compound 215
(racemic)

Racemic 4-methyl-1,3,2-dioxathiolane 2,2-dioxide

A procedure analogous to that set forth in the synthesis of Compound 202 was followed, with the exception that propane-1,2-diol was used as starting material.

Racemic (1S,2R)-ethyl 1-((diphenylmethylene)amino)-2-methylcyclopropane-carboxylate A procedure analogous to that set forth in the synthesis of Compound 202 was followed, with the exception that racemic 4-methyl-1,3,2-dioxathiolane 2,2-dioxide was used as starting material.

Racemic (1S,2R)-ethyl 1-amino-2-methylcyclopropanecarboxylate hydrochloride

A round bottomed flask was charged with racemic (1S,2R)-ethyl 1-((diphenylmethylene)amino)-2-methylcyclopropanecarboxylate and a stir bar. Et$_2$O (50 mL, 0.5 M) was added, and the mixture was cooled to 0° C. for the addition of 1 N HCl (9 mL, 1.2 equiv). The solution was warmed to room temperature and stirred overnight. The mixture was separated, and the organic layer was washed twice with water before being dried with Na$_2$SO$_4$ and concentrated. Lyophilization yielded racemic (1S,2R)-ethyl 1-amino-2-methylcyclopropanecarboxylate hydrochloride as a colorless oil that solidified upon sitting (yield not determined). LRMS (M+H)+: 144 m/z.

Racemic (1S,2R)-5'-(4-chlorophenyl)-2,6',7'-trimethylspiro[cyclopropane-1,3'-thieno[2,3-e][1,4]diazepin]-2'(1'H)-one A procedure analogous to that set forth in the synthesis of Compound 214 was followed, with the exception that racemic (1S,2R)-ethyl 1-amino-2-methylcyclopropanecarboxylate hydrochloride was used as starting material instead of 1-aminocyclopropanecarboxylate hydrochloride. LRMS (M+H)+: 345 m/z.

Racemic 4'-(4-chlorophenyl)-2,2',3',9'-tetramethyl-spiro[cyclopropane-1,6'-thieno[3,2-f][1,2,4]triazolo[4,3-a][1,4]diazepine] (Compound 215)

A procedure analogous to that set forth for Compound 202 was followed, with the exception that racemic (1S,2R)-5'-(4- chlorophenyl)-2,6',7'-trimethylspiro[cyclopropane-1,3'-thieno[2,3-e][1,4]diazepin]-2'(1'H)-one was used as starting material. LRMS (M+H)+: 383 m/z. ¹H NMR (400 MHz, DMSO-d₆) δ 7.50 (s, 4H), 2.59 (s, 3H), 2.39 (s, 3H), 1.96-2.02 (m, 1H), 1.58 (s, 3H), 1.39 (d, J=6.18 Hz, 1H), 1.04 (d, J=5.95 Hz, 1H), 0.79 (d, J=5.49 Hz, 3H).

EXAMPLE 28

Synthesis of 6-(4-chlorophenyl)-1-methylspiro[benzo[f][1,2,4]triazolo[4,3-a][1,4]diazepine-4,1'-cyclopropane] (Compound 216)

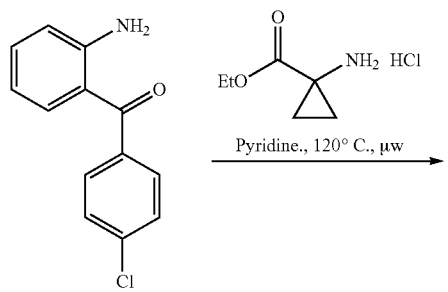

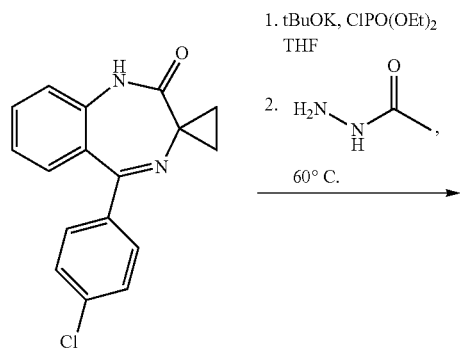

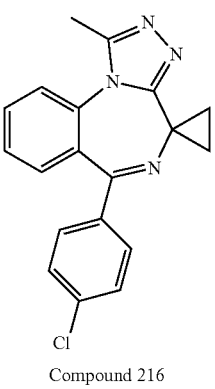

Compound 216

5-(4-Chlorophenyl)spiro[benzo[e][1,4]diazepine-3,1'-cyclopropan]-2(1H)-one (Step 1)

A procedure analogous to that set forth in the synthesis of Compound 214 was followed, with the exception that (2-aminophenyl)(4-chlorophenyl)methanone was used as starting material instead of (2-amino-4,5-dimethylthiophen-3-yl)(4-chlorophenyl)methanone. LRMS (M+H)+: 297 m/z.

6-(4-Chlorophenyl)-1-methylspiro[benzo[f][1,2,4]triazolo[4,3-a][1,4]diazepine-4,1'-cyclopropane] (Compound 216)

A procedure analogous to that set forth for Compound 202 was followed, with the exception that 5-(4-chlorophenyl)spiro[benzo[e][1,4]diazepine-3,1'-cyclopropan]-2(1H)-one was used as starting material. LRMS (M+H)+: 335 m/z. ¹H NMR (400 MHz, DMSO-d₆) δ 7.74-7.79 (m, 2H), 7.46-7.58 (m, 5H), 7.32 (d, J=7.55 Hz, 1H), 2.58 (s, 3H), 1.67-1.77 (m, 1H), 1.34-1.44 (m, 1H), 0.67-0.83 (m, 2H).

EXAMPLE 29

4'-(4-Chlorophenyl)-2',3'-dimethylspiro[cyclopropane-1,6'-thieno[3,2-f][1,2,4]triazolo[4,3-a][1,4]diazepine](Compound 217)

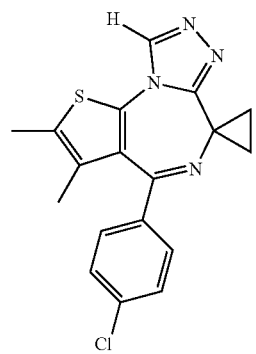 [SMILES: Cc1sc2c(c1C)C(c1ccc(Cl)cc1)=NC1(CC1)c1nncn1-2]

A procedure analogous to that set forth for Compound 202 was followed, with the exception that formohydrazide was used as reagent. LRMS (M+H)+: 355 m/z. ¹H NMR (400 MHz, DMSO-d₆) δ 9.09 (s, 1H), 7.48 (d, J=8.47 Hz, 2H), 7.43 (d, J=8.70 Hz, 2H), 2.38 (s, 3H), 1.57 (s, 3H), 1.03-1.33 (m, 4H).

EXAMPLE 30

Synthesis of (1R,2S)-5'-(4-chlorophenyl)-2,6',7'-trimethylspiro[cyclopropane-1,3'-thieno[2,3-e][1,4]diazepin]-2'(1'H)-one (Compound 218)

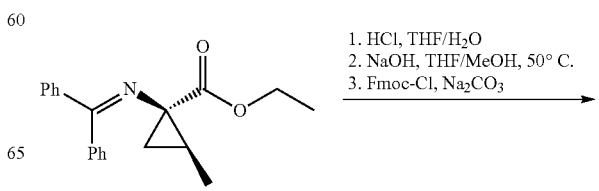

93

-continued

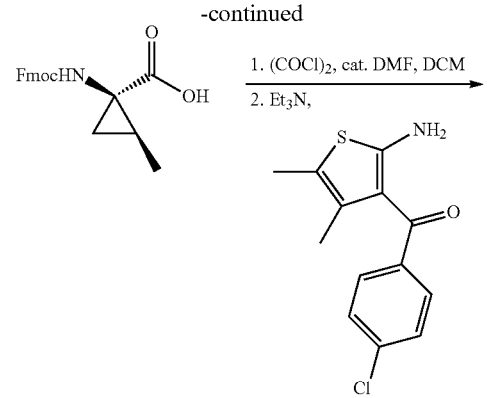

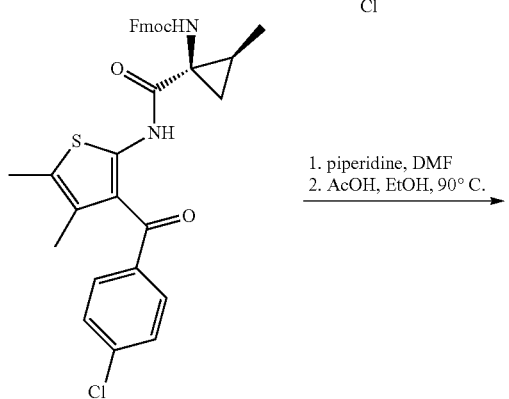

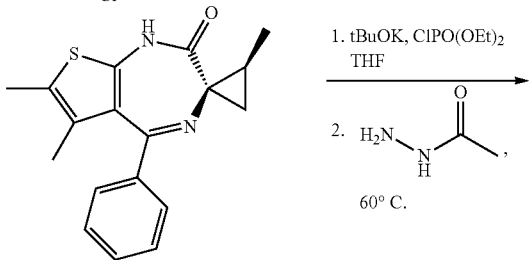

Compound 218

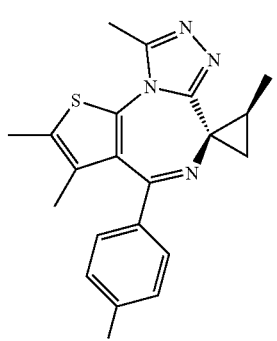

Compound 219

(1R,2S)-ethyl 1-((diphenylmethylene)amino)-2-methylcyclopropanecarboxylate

A procedure analogous to that set forth in the synthesis of Compound 202 was followed, with the exception that (R)-4-methyl-1,3,2-dioxathiolane 2,2-dioxide was used as starting material.

94

(1R,2S)-1-((9H-fluoren-9-yl)methoxy)carbonylamino)-2-methylcyclopropane-carboxylic acid A round bottomed flask was charged with (1R,2S)-ethyl 1-(diphenylmethyleneamino)-2-methylcyclopropanecarboxylate (4.928 g, 16.03 mmol) and a stir bar. THF (70 mL, 0.2 M) was added, followed by aqueous HCl (2.67 ml, 16.03 mmol), and the solution was stirred at rt before being concentrated and stripped with toluene. A 2:1 THF:MeOH (60 mL, 0.3 M) was added, followed by sodium hydroxide (6 N, 8.02 ml, 48.1 mmol). The mixture was stirred at 50° C. 0.5 h before being concentrated. Water (60 mL, 0.3 M) was added and adjusted to pH 7 with 1 N HCl before the addition of sodium carbonate (5.10 g, 48.1 mmol) and (9H-fluoren-9-yl)methyl carbonochloridate (8.29 g, 32.1 mmol) in dioxane (60 mL, 0.5 M). The solution was stirred at room temperature 1 h before being washed twice with Et2O. The aqueous layer was made acidic with 6 N HCl and washed three times with ethyl acetate. The second organic washes were combined, washed with brine, dried, and concentrated to give (1R,2S)-1-((9H-fluoren-9-yl)methoxy)carbonylamino)-2-methylcyclopropanecarboxylic acid as a white amorphous solid (408 mg). LRMS (M+H)$^+$: 360 m/z.

(9H-fluoren-9-yl)methyl (1R,2S)-1-(3-(4-chlorobenzoyl)-4,5-dimethylthiophen-2-ylcarbamoyl)-2-methylcyclopropylcarbamate A round bottomed flask was charged with (1R,2S)-1-(((9H-fluoren-9-yl)methoxy)carbonylamino)-2-methylcyclopropanecarboxylic acid (408 mg, 1.209 mmol) and a stir bar. DCM (25 mL, 0.05 M) was added, followed by one drop of DMF and oxalyl chloride (97 µl, 1.109 mmol). Stirred at room temperature 1 h. A solution of triethylamine (562 µl, 4.03 mmol) and (2-amino-4,5-dimethylthiophen-3-yl)(4-chlorophenyl)methanone (268 mg, 1.008 mmol) in DCM (10 mL, 0.1 M) was added dropwise, and the solution stirred at room temperature overnight before being concentrated with celite and purified by flash chromatography to give (9H-fluoren-9-yl)methyl (1R,2S)-1-(3-(4-chlorobenzoyl)-4,5-dimethylthiophen-2-ylcarbamoyl)-2-methylcyclopropylcarbamate as a yellow amorphous solid (225 mg) LRMS (M+H)$^+$: 586 m/z.

(1R,2S)-5'-(4-chlorophenyl)-2,6',7'-trimethylspiro[cyclopropane-1,3'-thieno[2,3-e][1,4]diazepin]-2'(1'H)-one (Compound 218)

A round bottomed flask was charged with 9H-fluoren-9-yl)methyl-(1R,2S)-1-(3-(4-chlorobenzoyl)-4,5-dimethylthiophen-2-ylcarbamoyl)-2-methylcyclopropylcarbamate (225 mg, 0.385 mmol) and a stir bar. DMF (16 mL, 0.02 M) was added, followed by piperidine (4 mL, 40.4 mmol), and the solution was stirred at room temperature 15 min. The solution was washed with water, extracted twice with ethyl acetate, washed with brine, and concentrated before being taken up in ethanol (25 mL). Acetic acid (12.5 mL, 218 mmol) was added, and the solution was stirred at 90° C. 3 h before being concentrated with celite and purified by column chromatography to give (1R,2S)-5'-(4-chlorophenyl)-2,6',7'-trimethylspiro[cyclopropane-1,3'-thieno[2,3-e][1,4]diazepin]-2'(1'H)-one (Compound 218) as a light yellow amorphous solid (96 mg). LRMS (M+H)$^+$: 345 m/z.

EXAMPLE 31

(1R,2S)-4'-(4-chlorophenyl)-2,2',3',9'-tetramethyl-spiro-[cyclopropane-1,6'-thieno[3,2-f][1,2,4]triazolo[4,3-a][1,4]diazepine] (Compound 219)

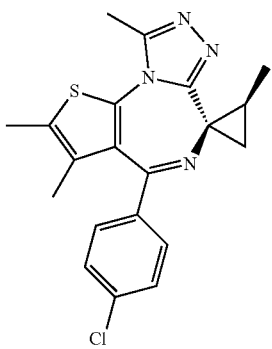

A procedure analogous to that set forth for Compound 202 was followed, with the exception that (1R,2S)-5'-(4-chlorophenyl)-2,6',7'-trimethylspiro[cyclopropane-1,3'-thieno[2,3-e][1,4]diazepin]-2'(1'H)-one (Compound 218) was used as starting material. LRMS (M+H)+: 383 m/z. 1H NMR (400 MHz, DMSO-d6) δ 7.50 (s, 4H), 2.56-2.62 (m, 3H), 2.39 (s, 3H), 1.94-2.05 (m, 1H), 1.58 (s, 3H), 1.39 (d, J=6.18 Hz, 1H), 1.10 (s, 1H), 0.79 (d, J=5.49 Hz, 3H).

EXAMPLE 32

Synthesis of (1S,2R)-4'-(4-chlorophenyl)-2,2',3',9'-tetramethyl-spiro[cyclopropane-1,6'-thieno[3,2-f][1,2,4]triazolo[4,3-a][1,4]diazepine] (Compound 220)

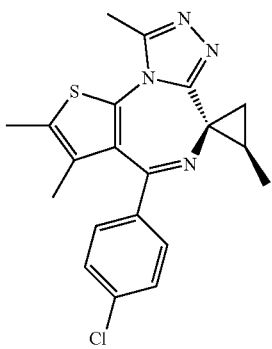

A procedure analogous to the scheme set forth for the synthesis of Compound 215 was followed, with the exception that (R)-propane-1,2-diol was used as starting material. LRMS (M+H)+: 383 m/z. 1H NMR (400 MHz, DMSO-d6) δ 7.50 (s, 4H), 3.80 (t, J=6.98 Hz, 1H), 2.55-2.63 (m, 3H), 2.39 (s, 3H), 1.95-2.03 (m, 1H), 1.58 (s, 3H), 1.39 (d, J=5.95 Hz, 1H), 1.05-1.12 (m, 1H), 0.79 (d, J=5.49 Hz, 3H).

EXAMPLE 33

4-((1S,2R)-2,2',3',9'-tetramethylspiro[cyclopropane-1,6'-thieno[3,2-f][1,2,4]triazolo[4,3-a][1,4]diazepin]-4'-yl)aniline (Compound 221)

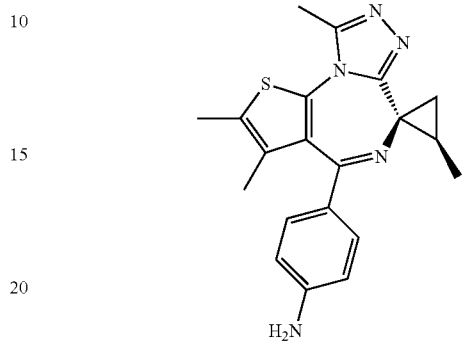

A disposable reaction tube was charged with (1S,2R)-4'-(4-chlorophenyl)-2,2',3',9'-tetramethylspiro[cyclopropane-1,6'-thieno[3,2-f][1,2,4]triazolo[4,3-a][1,4]diazepine] (Compound 220; 65 mg, 0.170 mmol), 2'-(di-tert-butylphosphino)-N,N-dimethylbiphenyl-2-amine (5.80 mg, 0.017 mmol), Pd2(dba)3 (3.11 mg, 3.40 µmol), sodium tertbutoxide (24.47 mg, 0.255 mmol), and a stir bar. The tube was evacuated and purged with N2 three times. Dioxane (0.85 mL, 0.2 M) was added, followed by ammonia (1698 µl, 0.849 mmol) in Dioxane, and the mixture was stirred at 80° C. 2.5 d before being concentrated, diluted in methanol, and filtered. The reaction mixture was purified by HPLC (eluting with water/acetonitrile/0.1% TFA) to give 44(1S,2R)-2,2',3',9'-tetramethylspiro[cyclopropane-1,6'-thieno[3,2-f][1,2,4]triazolo[4,3-a][1,4]diazepin]-4'-yl)aniline (Compound 221) as a yellow amorphous solid (40 mg). LRMS (M+H)+: 364 m/z. 1H NMR (400 MHz, DMSO-d6) δ 7.18 (d, J=6.87 Hz, 2H), 6.53 (d, J=9.61 Hz, 2H), 5.44-5.92 (m, 2H), 2.56 (d, J=1.37 Hz, 3H), 2.39 (s, 3H), 1.85-1.96 (m, 1H), 1.68 (s, 3H), 1.36 (d, J=8.01 Hz, 1H), 0.97-1.03 (m, 1H), 0.74 (d, J=5.95 Hz, 3H).

EXAMPLE 34

Synthesis of 4'-(4-chlorophenyl)-2,2',3'-trimethyl-spiro-[cyclopropane-1,6'-thieno[3,2-f][1,2,4]triazolo[4,3-a][1,4]diazepin]-9'-ol (Compound 222)

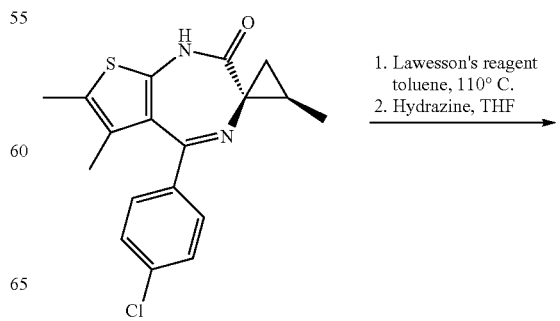

1. Lawesson's reagent toluene, 110° C.
2. Hydrazine, THF

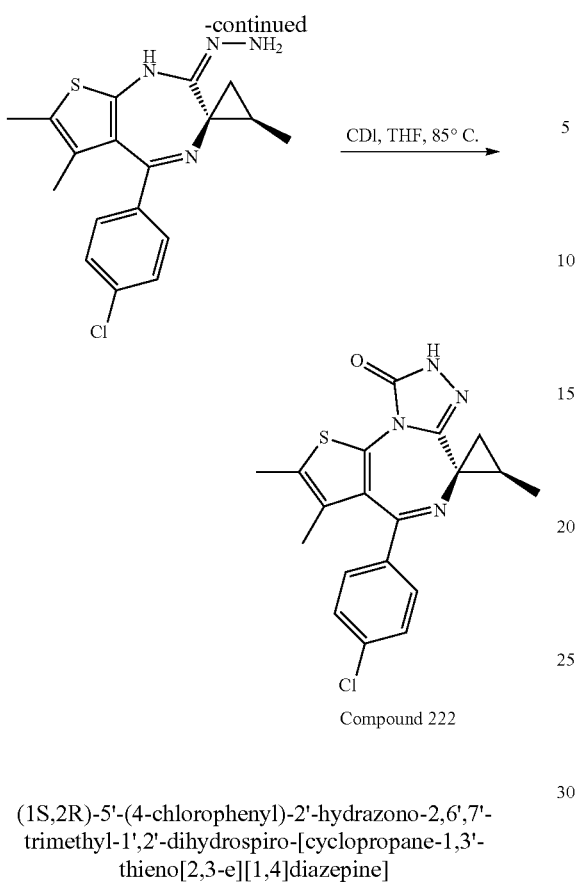

Compound 222

(1S,2R)-5'-(4-chlorophenyl)-2'-hydrazono-2,6',7'-trimethyl-1',2'-dihydrospiro-[cyclopropane-1,3'-thieno[2,3-e][1,4]diazepine]

A round bottomed flask was charged with (1S,2R)-5'-(4-chlorophenyl)-2,6',7'-trimethylspiro[cyclopropane-1,3'-thieno[2,3-e][1,4]diazepin]-2'(1'H)-one (289 mg, 0.838 mmol) and a stir bar. Toluene (8.5 mL, 0.1 M) added, followed by Lawesson's Reagent (186 mg, 0.461 mmol), and the reaction was stirred at 110° C. After conversion to the thioamide intermediate, as determined by LC/MS, the reaction was cooled and diluted with THF (20 mL) for the addition of hydrazine (263 μl, 8.38 mmol). The reaction was stirred at room temperature before being concentrated and purified by column chromatography to give (1S,2R)-5'-(4-chlorophenyl)-2'-hydrazono-2,6',7'-trimethyl-1',2'-dihydrospiro[cyclopropane-1,3'-thieno[2,3-e][1,4]diazepine] (249 mg). LRMS (M+H)$^+$: 359 m/z

(1S,2R)-4'-(4-chlorophenyl)-2,2',3'-trimethylspiro[cyclopropane-1,6'-thieno[3,2-f][1,2,4]triazolo[4,3-a][1,4]diazepin]-9'(8'H)-one 2,2,2-trifluoroacetic acid (Compound 222)

A disposable tube was charged with (1S,2R)-5'-(4-chlorophenyl)-2'-hydrazono-2,6',7'-trimethyl-1',2'-dihydrospiro[cyclopropane-1,3'-thieno[2,3-e][1,4]diazepine] (24 mg, 0.067 mmol) and a stir bar. THF (1.5 mL, 0.05 M) was added, followed by CDI (13.01 mg, 0.080 mmol), and the solution was stirred 85° C. 4 h. At 4 h, more CDI (26 mg, 0.160 mmol) was added, and the reaction was stirred at 85° C. The reaction was concentrated and purified by reverse phase chromatography (water/acetonitrile with 0.1% TFA) to give (1S,2R)-4'-(4-chlorophenyl)-2,2',3'-trimethylspiro[cyclopropane-1,6'-thieno[3,2-f][1,2,4]triazolo[4,3-a][1,4]diazepin]-9'(8'H)-one (2,2,2-trifluoroacetic acid salt) (Compound 222) as a yellow amorphous solid (17 mg). LRMS (M+H)$^+$: 385 m/z. $^1$H NMR (400 MHz, DMSO-d$_6$) δ 12.08 (s, 1H), 7.49 (d, J=8.90 Hz, 2H), 7.42 (d, J=8.70 Hz, 2H), 2.34 (s, 3H), 1.52 (s, 3H), 1.18 (s, OH), 1.16 (s, 1H), 1.15 (s, 1H), 0.87 (br. s., 2H).

EXAMPLE 35

Synthesis of 4'-(4-chlorophenyl)-2',3',9'-trimethyl-spiro-[cyclobutane-1,6'-thieno[3,2-f][1,2,4]triazolo[4,3-a][1,4]diazepine] (2,2,2-trifluoroacetic acid salt) (Compound 223)

5'-(4-chlorophenyl)-6',7'-dimethylspiro[cyclobutane-1,3'-thieno[2,3-e][1,4]diazepin]-2'(1'H)-one(2,2,2-trifluoroacetic acid salt)

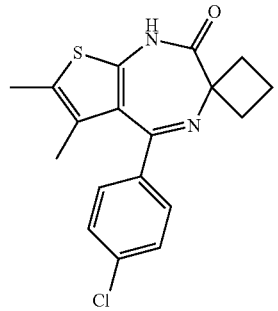 [SMILES: Cc1sc2c(c1C)C(c1ccc(Cl)cc1)=NC1(CCC1)C(=O)N2]

A procedure analogous to that set forth in the synthesis of Compound 214 was followed, with the exception that ethyl 1-aminocyclobutanecarboxylate hydrochloride was used as starting material. LRMS (M+H)$^+$: 345 m/z.

4'-(4-chlorophenyl)-2',3',9'-trimethylspiro[cyclobutane-1,6'-thieno[3,2-f][1,2,4]triazolo[4,3-a][1,4]diazepine](2,2,2-trifluoroacetic acid salt)(Compound 223)

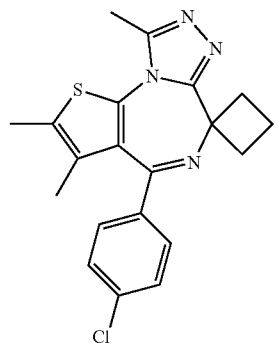 [SMILES: Cc1sc2c(c1C)C(c1ccc(Cl)cc1)=NC1(CCC1)c1nnc(C)n1-2]

A procedure analogous to that set forth in the synthesis of Compound 202 (Step 6) was followed, with the exception that 5'-(4-chlorophenyl)-6',7'-dimethylspiro[cyclobutane-1,3'-thieno[2,3-e][1,4]diazepin]-2'(1'H)-one 2,2,2-trifluoroacetate was used as starting material. LRMS (M+H)$^+$: 383 m/z. $^1$H NMR (400 MHz, DMSO-d$_6$) δ7.50 (s, 4H), 3.28-3.39 (m, 1H), 2.73-2.87 (m, 1H), 2.60 (s, 3H), 2.39 (s, 3H), 1.89-1.98 (m, 1H), 1.78-1.88 (m, 1H), 1.64-1.74 (m, 2H), 1.61 (s, 3H).

EXAMPLE 36

Synthesis of 4'-(4-chlorophenyl)-2',3',9'-trimethyl-spiro[azetidine-3,6'-thieno[3,2-f][1,2,4]triazolo[4,3-a][1,4]diazepine] (Compound 224)

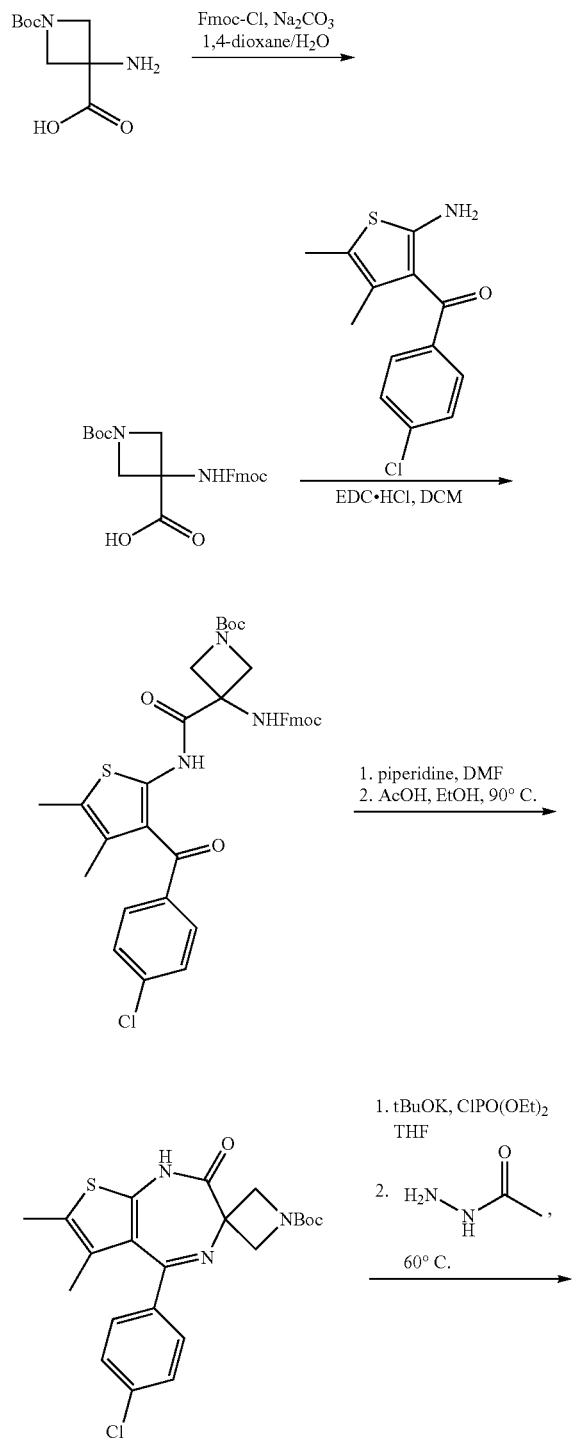

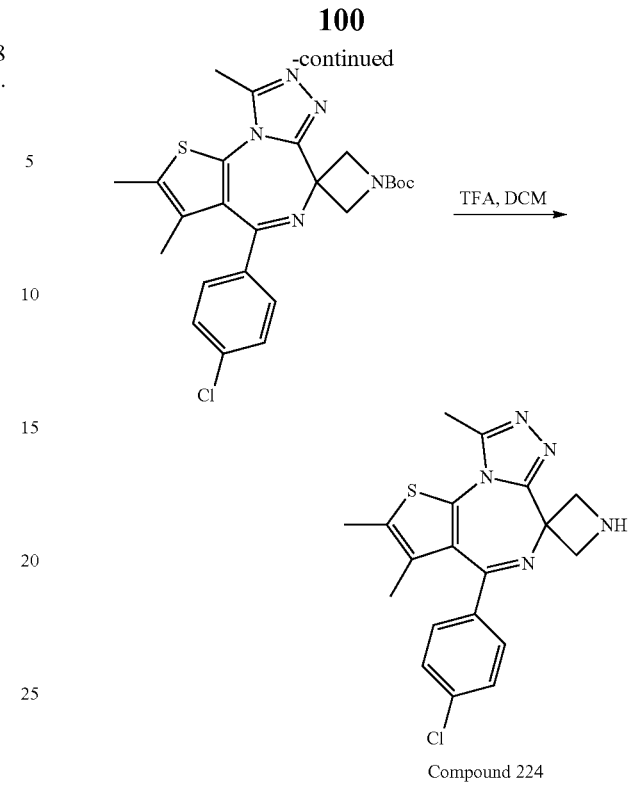

Compound 224

3-((((9H-Fluoren-9-yl)methoxy)carbonyl)amino)-1-(tert-butoxycarbonyl)azetidine-3-carboxylic acid A round bottomed flask was charged with 3-amino-1-(tert-butoxycarbonyl)azetidine-3-carboxylic acid (prepared according the procedure described in *Synthesis* 1991, 783-784.) (2.464 mmol), sodium carbonate (1.3 g, 12.32 mmol), a stir bar and water (70 mL). (9H-fluoren-9-yl)methyl carbonochloridate (1.9 g, 7.39 mmol) in 1,4-dioxane (50 mL) was added and the milky solution was stirred overnight at rt. The next day the reaction was poured into a separatory funnel and the aqueous solution washed with diethyl ether (repeated twice) (organic phases were discarded at this stage). The aqueous phase was acidified to pH 2-3 with 1 M HCl (a precipitate was formed) and the product was extracted with EtOAc (repeated 3 times). The combined organic layers were washed with brine, dried over $Na_2SO_4$, filtered and concentrated to dryness. The solid was used without purification in the next step. LRMS (M+Na)$^+$: 461 m/z.

tert-Butyl 3-((((9H-fluoren-9-yl)methoxy)carbonyl) amino)-3-((3-(4-chlorobenzoyl)-4,5-dimethylthiophen-2-yl)carbamoyl)azetidine-1-carboxylate To a solution of 3-(((9H-fluoren-9-yl)methoxy)carbonylamino)-1-(tert-butoxycarbonyl)azetidine-3-carboxylic acid (0.438 g, 0.999 mmol), and (2-amino-4,5-dimethylthiophen-3-yl)(4-chlorophenyl)methanone (0.241 g, 0.908 mmol) in DCM (20 mL) at 0° C. was added N1-((ethylimino)methylene)-N3,N3-dimethylpropane-1,3-diamine hydrochloride (EDC.HCl) (209 mg, 1.090 mmol). The reaction was warmed to rt and stirred overnight, before it was concentrated to dryness. The residue was purified by flash chromatography (hexane/EtOAc) to give tert-Butyl 3-((((9H-fluoren-9-yl) methoxy)carbonyl)amino)-3-((3-(4-chlorobenzoyl)-4,5- dimethylthiophen-2-yl)carbamoyl)-azetidine-1-carboxylate as an orange oil (382 mg). LRMS (M+Na)⁺: 708 m/z.

tert-Butyl 5'-(4-chlorophenyl)-6',7'-dimethyl-2'-oxo-1',2'-dihydrospiro[azetidine-3,3'-thieno[2,3-e][1,4]diazepine]-1-carboxylate A procedure analogous to that set forth in the synthesis of Compound 218 was followed, with the exception that tert-Butyl 34(((9H-fluoren-9-yl)methoxy)carbonyl)amino)-3-((3-(4-chlorobenzoyl)-4,5-dimethylthiophen-2-yl)carbamoyl)-azetidine-1-carboxylate was used as starting material. LRMS (M+H)⁺: 446 m/z.

4'-(4-chlorophenyl)-2',3',9'-trimethylspiro[azetidine-3,6'-thieno[3,2-f][1,2,4]-triazolo[4,3-a][1,4]diazepine]-1-carboxylate A procedure analogous to that set forth for the synthesis of Compound 202 (Step 6) was followed, with the exception that tert-Butyl 5'-(4-chlorophenyl)-6',7'-dimethyl-2'-oxo-1',2'-dihydrospiro[azetidine-3,3'-thieno[2,3-e][1,4]diazepine]-1-carboxylate was used as starting material. LRMS (M+H)⁺: 484 m/z.

4'-(4-Chlorophenyl)-2',3',9'-trimethylspiro[azetidine-3,6'-thieno[3,2-f][1,2,4]triazolo-[4,3-a][1,4]diazepine] (Compound 224)

To a solution of tert-butyl 4'44-chlorophenyl)-2',3',9'-trimethylspiro[azetidine-3,6'-thieno[3,2-f][1,2,4]triazolo[4,3-a][1,4]-diazepine]-1-carboxylate (0.073 g, 0.151 mmol) in DCM (4.5 mL) was added TFA (1.162 ml, 15.08 mmol) at rt. After 80 min the reaction was concentrated to dryness under vacuum, diluted in DCM and concentrated again to dryness (the last 2 steps were repeated once). The residue was purified by reverse phase chromatography to give 4'-(4-chlorophenyl)-2',3',9'-trimethylspiro[azetidine-3,6'-thieno[3,2-f][1,2,4]triazolo[4,3-a][1,4]diazepine] (Compound 224) as a off-white solid. LRMS (M+H)⁺: 384 m/z. ¹H NMR (400 MHz, DMSO-d₆) δ 7.43-7.56 (m, 4H), 4.70 (d, J=8.70 Hz, 1H), 4.33 (d, J=8.70 Hz, 1H), 3.44 (d, J=9.16 Hz, 1H), 3.32 (br. s., 1H), 2.54-2.63 (m, 3H), 2.36 (s, 3H), 1.60 (s, 3H).

EXAMPLE 37

Synthesis of 4'-(4-Chlorophenyl)-2',3',9'-trimethylspiro[oxetane-3,6'-thieno[3,2-f][1,2,4]triazolo[4,3-a][1,4]diazepine] (Compound 225)

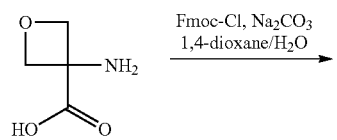

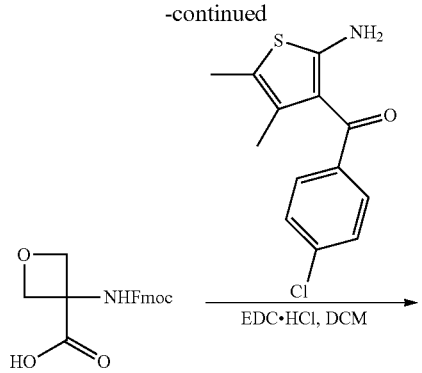

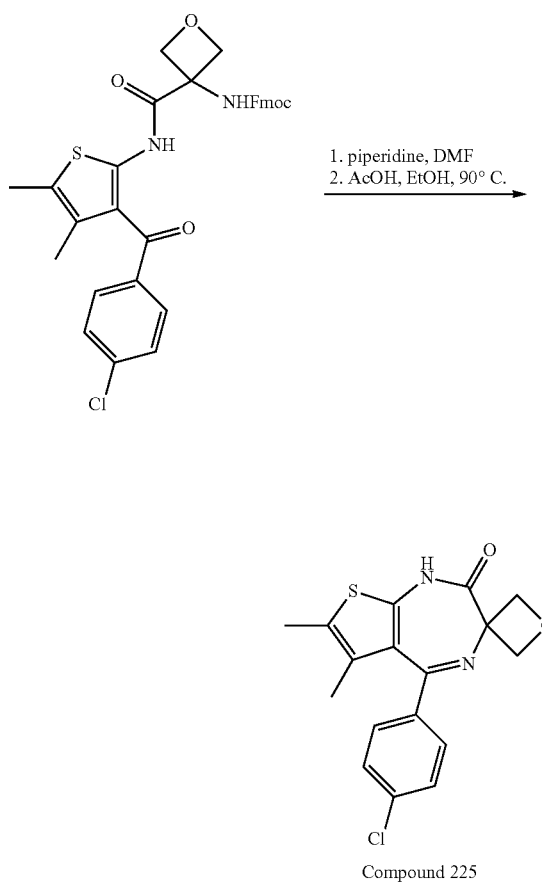

Compound 225

A procedure analogous to the scheme set forth for the synthesis of Compound 224 was followed, with the exception that 3-aminooxetane-3-carboxylic acid was used as starting material instead of 3-amino-1-(tert-butoxycarbonyl)azetidine-3-carboxylic acid.

5'-(4-Chlorophenyl)-6',7'-dimethylspiro[oxetane-3,3'-thieno[2,3-e][1,4]diazepin]-2'(1'H)-one (Compound 225)

LRMS (M+H)⁺: 347 m/z. ¹H NMR (400 MHz, DMSO-d6) δ 11.38 (br. s., 1H), 7.39-7.63 (m, 4H), 5.34 (d, J=5.95 Hz, 1H), 4.93 (d, J=6.18 Hz, 1H), 4.22 (d, J=7.10 Hz, 1H), 4.01 (d, J=7.10 Hz, 1H), 2.25 (s, 3H), 1.56 (s, 3H).

EXAMPLE 38

4'-(4-Chlorophenyl)-2',3',9'-trimethylspiro[oxetane-3,6'-thieno[3,2-f][1,2,4]triazolo[4,3-a][1,4]diazepine] (Compound 226)

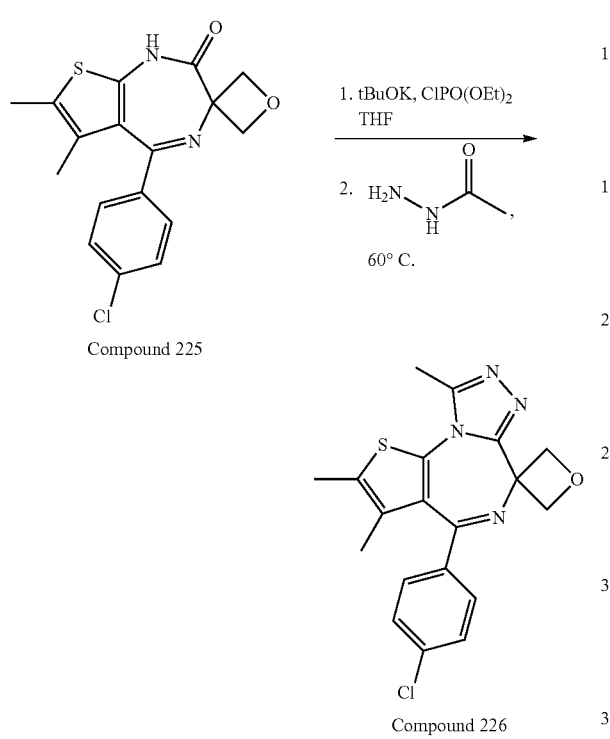

Compound 225

Compound 226

This compound was synthesized from Compound 225 as indicated above. LRMS (M+H)+: 385 m/z. $^1$H NMR (400 MHz, DMSO-d$_6$) δ 7.46-7.57 (m, 4H), 5.60 (d, J=6.18 Hz, 1H), 5.25 (d, J=6.18 Hz, 1H), 4.35 (d, J=6.64 Hz, 1H), 4.28 (d, J=6.64 Hz, 1H), 2.59 (s, 3H), 2.35 (s, 3H), 1.60 (s, 3H).

EXAMPLE 39

Synthesis of 4-(4-chlorophenyl)-N,2,3,6,9-pentamethyl-6H-thieno[3,2-f][1,2,4]triazolo[4,3-a][1,4]diazepin-6-amine (Compound 230)

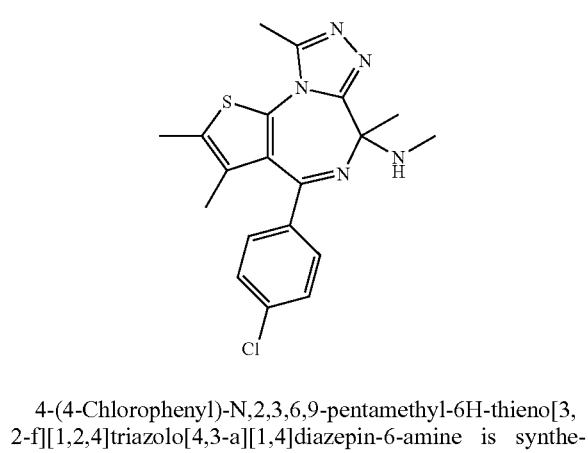

4-(4-Chlorophenyl)-N,2,3,6,9-pentamethyl-6H-thieno[3,2-f][1,2,4]triazolo[4,3-a][1,4]diazepin-6-amine is synthesized similarly to methods described in J. Med. Chem., 1988, 31 (1), pp 176-181; and Tetrahedron Letters, Volume 28, Issue 9, 1987, Pages 939-942 (each of which are incorporated herein by reference). See scheme below. Other A ring and Hy heterocycles can be synthesized using analogous procedures.

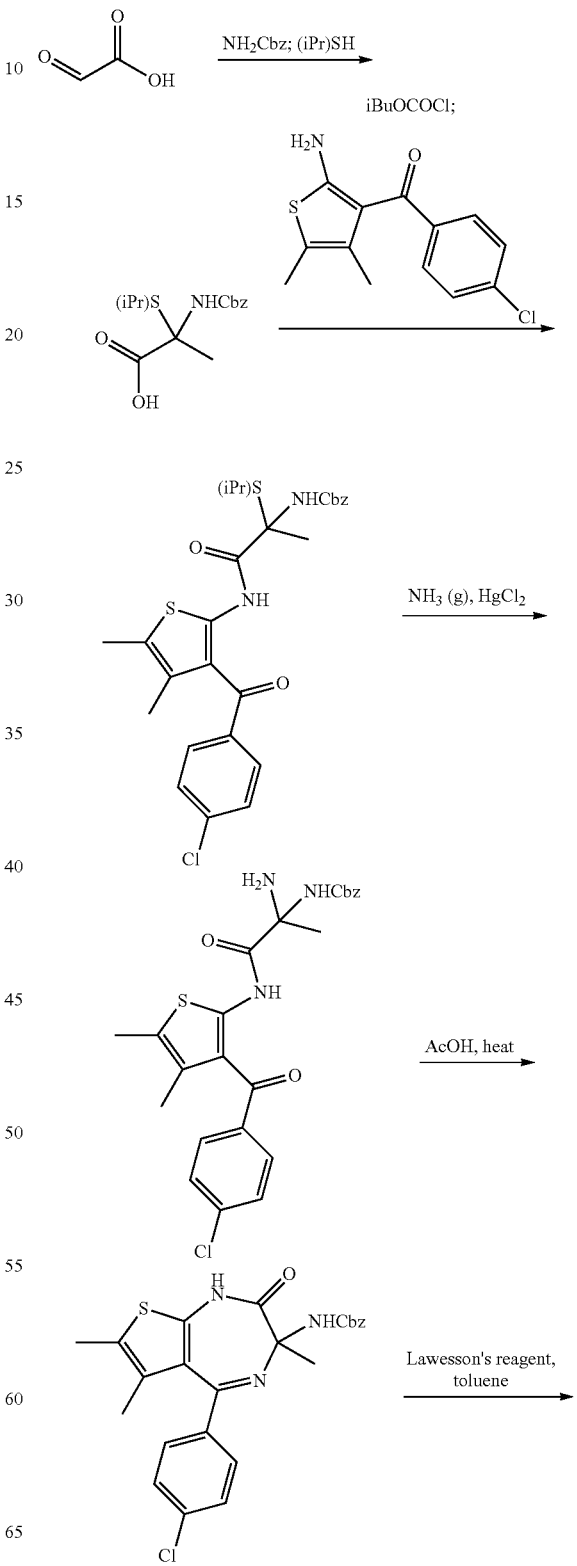

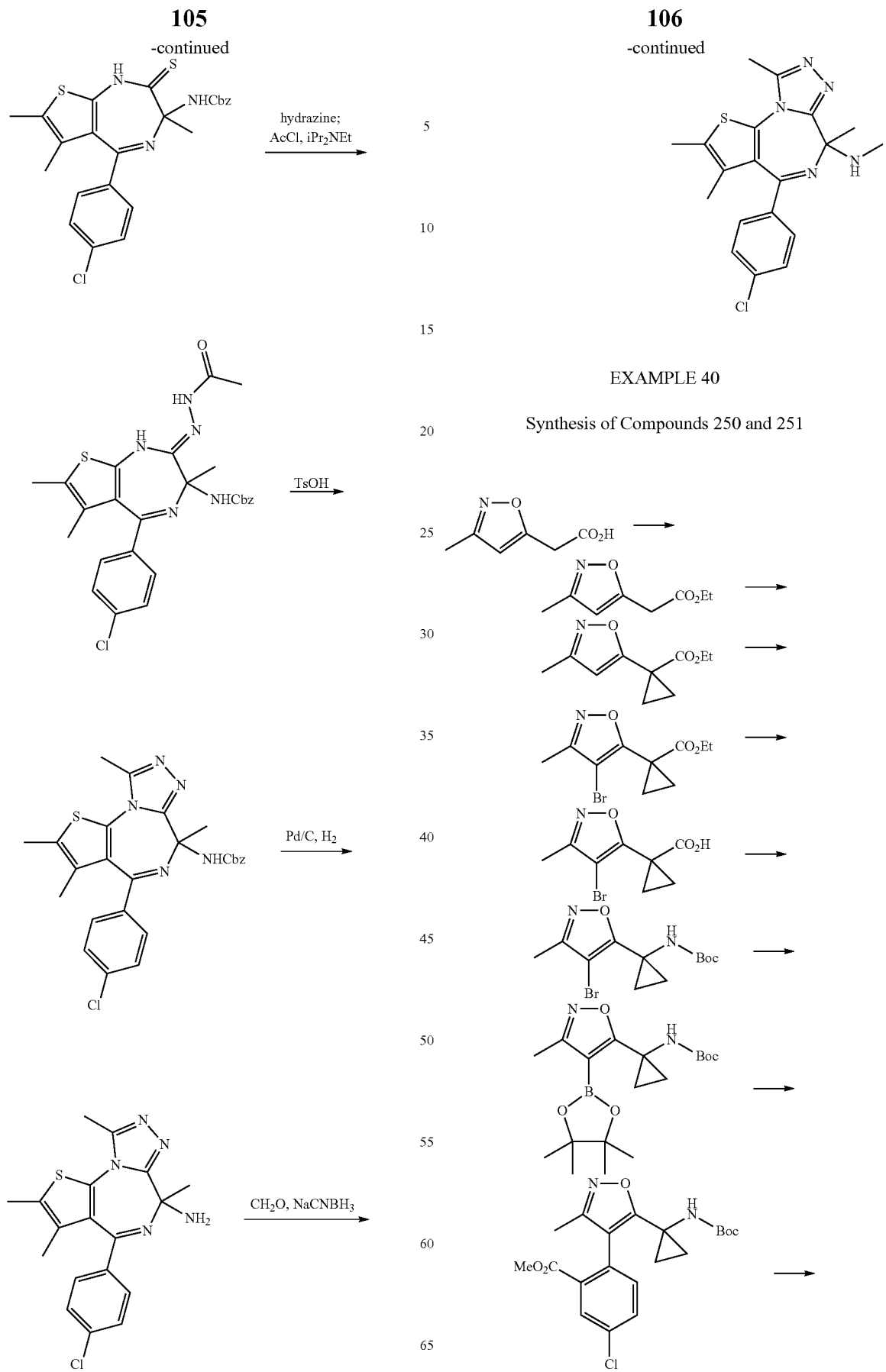
EXAMPLE 40
Synthesis of Compounds 250 and 251

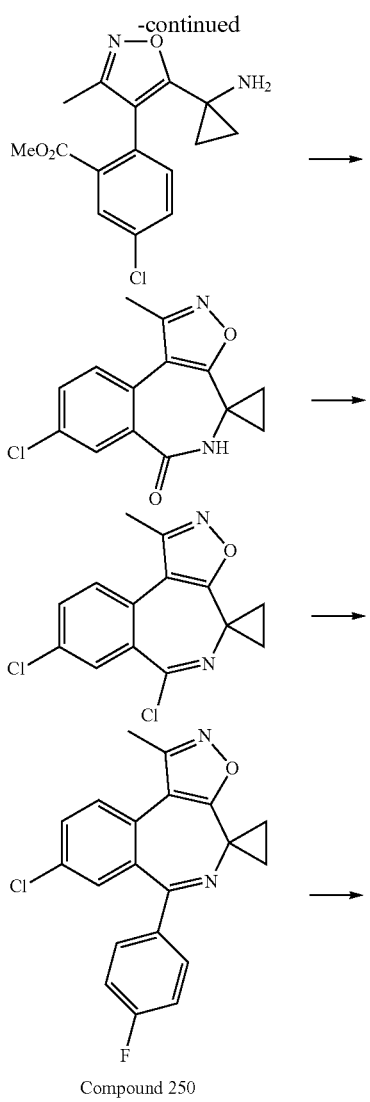

Compound 250

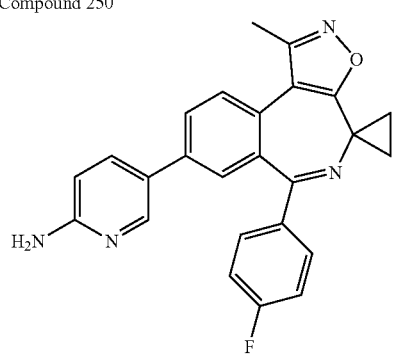

Compound 251

Ethyl 2-(3-methylisoxazol-5-yl)acetate

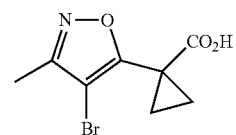

To a solution of 2-(3-methylisoxazol-5-yl)acetic acid (7.28 g, 51.6 mmol) in EtOH (200 mL, 3425 mmol) was added concentrated $H_2SO_4$ (0.30 mL, 5.63 mmol) at room temperature. After 48 h, the reaction mixture was concentrated in vacuo to give a dark brown oil. The crude ester was filtered over a plug of silica (50 g) and the product was eluted with 40% $Et_2O$:60% Hexanes (400 mL). The filtrate was subsequently concentrated to give the product ethyl 2-(3-methylisoxazol-5-yl)acetate (8.50 g, 50.2 mmol, 97% yield) as a clear oil. LC/MS m/z 170 [M+H]$^+$.

Ethyl 1-(3-methylisoxazol-5-yl)cyclopropanecarboxylate

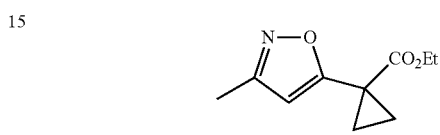

To a solution of ethyl 2-(3-methylisoxazol-5-yl)acetate (8.22 g, 48.6 mmol) in toluene (85 mL) was sequentially added n-tetrabutylammonium bromide (1.67 g, 5.18 mmol), 1,2-dibromoethane (7.0 mL, 81 mmol), and NaOH (30 mL, 582 mmol, ~19.4 M). The reaction mixture was vigorously stirred at room temperature. After 1 h, the reaction mixture was cooled to 0° C. and diluted with water (50 mL). The aqueous phase was extracted with MTBE (3×). The combined organic phases were washed 1 N HCl, water (2×), dried over $Na_2SO_4$, and concentrated to give the product ethyl 1-(3-methylisoxazol-5-yl)cyclopropanecarboxylate (9.49 g, 48.6 mmol, 100% yield) as a clear oil. LC/MS m/z 196 [M+H]$^+$.

Ethyl 1-(4-bromo-3-methylisoxazol-5-yl)cyclopropanecarboxylate

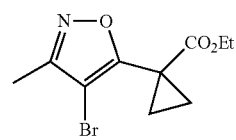

To a solution of ethyl 1-(3-methylisoxazol-5-yl)cyclopropanecarboxylate (9.49 g, 48.6 mmol) in anhydrous DMF (50 mL) was added N-bromosuccinimide (10.31 g, 57.9 mmol). The reaction mixture was stirred at room temperature for 24 h. To the orange mixture was added water and the aqueous layer was extracted with MTBE (3×). The combined organic layers were washed with aqueous 10% sodium thiosulfate, water (2×) and dried to provide the product ethyl 1-(4-bromo-3-methylisoxazol-5-yl)cyclopropanecarboxylate (12.5 g, 45.6 mmol, 94% yield) as a light yellow oil. The product was used directly in the subsequent reaction without further purification. LC/MS m/z 274 [M+H]$^+$.

1-(4-Bromo-3-methylisoxazol-5-yl)cyclopropanecarboxylic acid

To a solution of ethyl 1-(4-bromo-3-methylisoxazol-5-yl)cyclopropane-carboxylate (11.8 g, 43.0 mmol) in THF (60 mL) was added aqueous NaOH (86 mL, 86 mmol, 1 M). The dark brown bi-phasic reaction mixture was vigorously stirred and heated to 45° C. until consumption of SM (3-4 h) was detected by LC-MS and TLC analysis. After 4 h, the homogeneous mixture was cooled to room temperature and diluted with hexanes. The organic phase was separated and the aqueous phase (pH~14) was acidified with aqueous 1 N HCl (pH 1) (~100 mL). The product crystallizes upon acidification of the aqueous layer. After vigorously stirring for 30 min, the solids were filtered, washed with cold (0° C.) water (3×50 mL), and dried to give white crystals. The product 1-(4-bromo-3-methylisoxazol-5-yl)cyclopropanecarboxylic acid (10.0 g, 40.6 mmol, 94% yield) was isolated as white crystals. LC/MS m/z 246 [M+H]$^+$.

Tert-Butyl (1-(4-bromo-3-methylisoxazol-5-yl)cyclopropyl)carbamate

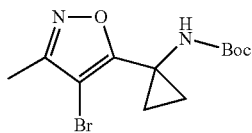 [SMILES: Cc1noc(C2(NC(=O)OC(C)(C)C)CC2)c1Br]

To a suspension of 1-(4-bromo-3-methylisoxazol-5-yl)cyclopropanecarboxylic acid (1.60 g, 6.50 mmol) and powdered 4 Å molecular sieves (pre-dried-0.767 g, 48% wt) in toluene (15 mL) was sequentially added N,N-diisopropylethylamine (1.50 mL, 8.59 mmol), diphenyl phosphorazidate (1.576 mL, 7.05 mmol), and tert-butanol (16.80 mL, 176 mmol). The reaction vessel was fitted with a reflux condenser and the mixture was heated to 100° C. for 1 h. After 1 h, the reaction mixture was cooled to room temperature and filtered over a plug of Celite. The filter cake was washed with EtOAc (3×), and the filtrate was concentrated to give a brown oil. The oil was purified on Biotage system (5% EtOAc:95% Hexanes to 20% EtOAc:80% Hexanes). The product tert-butyl 1-(4-bromo-3-methylisoxazol-5-yl)cyclopropylcarbamate (1.55 g, 4.89 mmol, 75% yield) was isolated as white crystals after concentration. LC/MS m/z 317 [M+H]$^+$.

Tert-Butyl (1-(3-methyl-4-(4,4,5,5-tetramethyl-1,3,2-dioxaborolan-2-yl)isoxazol-5-yl)cyclopropyl)carbamate

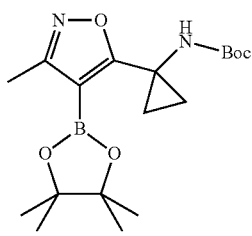 [SMILES: Cc1noc(C2(NC(=O)OC(C)(C)C)CC2)c1B1OC(C)(C)C(C)(C)O1]

To a 50 mL round bottom flask containing tert-butyl 1-(4-bromo-3-methylisoxazol-5-yl)cyclopropylcarbamate (0.219 g, 0.621 mmol) was added dichlorobis(acetonitrile)palladium(II) (0.0025 g, 9.64 µmol), dicyclohexyl(2',6'-dimethoxybiphenyl-2-yl)phosphine (0.0134 g, 0.033 mmol), followed by anhydrous 1,4-dioxane (0.40 mL). The reaction vessel was evacuated and purged with N$_2$ (g) (3×). To the flask was added 4,4,5,5-tetramethyl-1,3,2-dioxaborolane (0.153 mL, 1.056 mmol) and triethylamine (0.294 mL, 2.113 mmol) sequentially. The reaction vessel was evacuated and purged with N$_2$ (g) again, then heated to 100° C. The reaction mixture became heterogeneous and was judged complete within 1 h by LC-MS. The heterogeneous mixture was cooled to room temperature, dilute with EtOAc and the mixture was filtered over a plug of Celite. The filter cake was rinsed with EtOAc (3×) and the filtrate was concentrated to give a yellow oil, that crystallized upon standing under vacuum. The product tert-butyl 1-(3-methyl-4-(4,4,5,5-tetramethyl-1,3,2-dioxaborolan-2-yl)isoxazol-5-yl)cyclopropylcarbamate (0.226 g, 0.620 mmol, 100% yield) was used without further purification. LC/MS m/z 365 [M+H]$^+$.

Methyl 2-(5-(1-((tert-butoxycarbonyl)amino)cyclopropyl)-3-methylisoxazol-4-yl)-5-chlorobenzoate

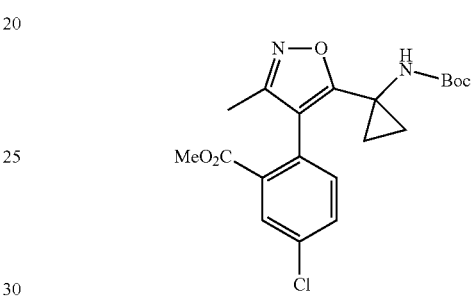

A re-sealable vial containing methyl 2-bromo-5-chlorobenzoate (0.205 g, 0.822 mmol), Pd(Ph$_3$P)$_4$ (0.042 g, 0.036 mmol), and anhydrous potassium phosphate, tribasic (0.275 g, 1.296 mmol) was evacuated and purged with N$_2$ (g) (3×). To the solids was added a solution of tert-butyl 1-(3-methyl-4-(4,4,5,5-tetramethyl-1,3,2-dioxaborolan-2-yl)isoxazol-5-yl)cyclopropyl-carbamate (0.236 g, 0.648 mmol) in MeOH (2×1 mL, 2 mL total) and 1,4-Dioxane (2×1 mL, 2 mL total). The suspension was evacuated and purged with N$_2$ (g) (3×), the vial was sealed, and the contents heated to 80° C. LC-MS analysis indicated complete conversion to desired product with in 4 h. After 4 h, the reaction mixture was cooled to room temperature and filtered over Celite. The filter cake was washed with MeOH (3×) and the filtrate was concentrated to give a brown oil. The oil was purified on Biotage system (5% EtOAc:95% Hexanes to 30% EtOAc:70% Hexanes, then isocratic 30% EtOAc:70% Hexanes). The product methyl 2-(5-(1-(tert-butoxycarbonylamino)cyclopropyl)-3-methylisoxazol-4-yl)-5-chlorobenzoate (0.226 g, 0.555 mmol, 86% yield) was isolated as a clear oil. LC/MS m/z 407 [M+H]$^+$.

8-Chloro-1-methylspiro[benzo[c]isoxazolo[4,5-e]azepine-4,1'-cyclopropan]-6(5H)-one

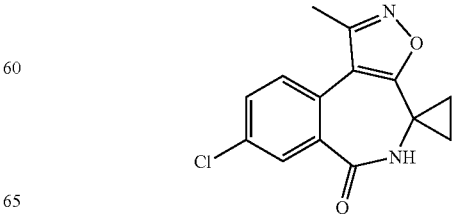

To a solution of methyl 2-(5-(1-(tert-butoxycarbonylamino)cyclo-propyl)-3-methylisoxazol-4-yl)-5-chlorobenzoate (131 mg, 0.322 mmol) in MeOH (2 mL) was added anhydrous HCl (1.00 mL, 4.00 mmol, 4 M in 1,4-dioxane). The reaction mixture was stirred at room temperature for 6 h, at which point LC-MS analysis indicated complete consumption of N-Boc carbamate and formation of desired product. The reaction mixture was concentrated in vacuo and excess HCl was azeotropically removed with MeOH (1×1 mL), toluene (1×1 mL), and THF (1×1 mL). The resultant yellow oil was dried for 10 min. LC/MS m/z 307 [M+H]⁺.

To a cooled (−40° C.) suspension of crude ammonium hydrochloride salt (~100 mg) in THF (1.5 mL) was added isopropylmagnesium bromide (0.400 mL, 1.160 mmol) in a dropwise manner. After complete addition, the reaction mixture was allowed to warm to room temperature and stirred for an additional 15 min. To the reaction mixture was added aqueous 1 N HCl (until pH~1 was obtained for the aqueous layer). The aqueous phase was extracted with EtOAc and the combined organic phase was washed with water, dried over Na$_2$SO$_4$ and concentrated to give the product 8-chloro-1-methylspiro[benzo[e]isoxazolo[5,4-c]azepine-4,1'-cyclopropan]-6(5H)-one (0.0631 g, 0.230 mmol, 71.3% yield over 2-steps) as light yellow solids. The crude product was sufficiently pure by LC-MS analysis and used without further purification. LC/MS m/z 275 [M+H]⁺.

6,8-Dichloro-1-methylspiro[benzo[c]isoxazolo[4,5-e]azepine-4,1'-cyclopropane]

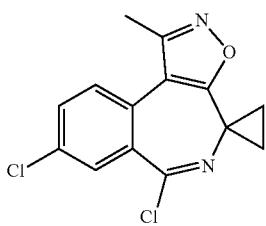 [SMILES: Cc1noc2c1-c1ccc(Cl)cc1C(Cl)=NC21CC1]

To a vial containing 8-chloro-1-methylspiro[benzo[e]isoxazolo[5,4-c]azepine-4,1'-cyclopropan]-6(5H)-one (0.0631 g, 0.230 mmol) was added CH$_2$Cl$_2$ (1 mL). The reaction mixture was heterogeneous and to aid in solubility CHCl$_3$ (0.5 mL) was added. To the homogeneous mixture was added phosphorous pentachloride (0.092 g, 0.442 mmol) in one portion at room temperature. The reaction mixture eventually turned heterogeneous again (~<10 min) and LC-MS analysis after ~30 min indicated complete consumption of starting material and formation of desired product. The mixture was diluted with EtOAc and aqueous 10% Na$_2$CO$_3$ (2.8 mL). After initial effervescence, the mixture was stirred for an additional 5-10 min, and the aqueous layer was extracted with EtOAc (3×). The combine organic extracts were washed with water, brine, dried over Na$_2$SO$_4$ and concentrated to give yellow solids. The solids were filtered over a plug of silica and eluted with 30% EtOAc:70% Hexanes. The product 6,8-dichloro-1-methylspiro[benzo[e]isoxazolo[5,4-c]azepine-4,1'-cyclopropane] (61.8 mg, 0.211 mmol, 92% yield) was obtained as off-white solids. LC/MS m/z 293 [M+H]⁺.

8-Chloro-6-(4-fluorophenyl)-1-methylspiro[benzo[c]isoxazolo[4,5-e]azepine-4,1'-cyclopropane] (Compound 250)

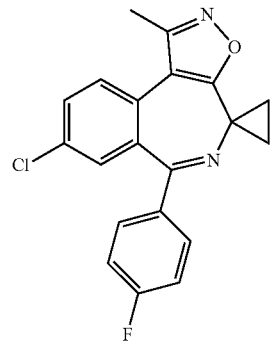 [SMILES: Cc1noc2c1-c1ccc(Cl)cc1C(c1ccc(F)cc1)=NC21CC1]

To a solution of 6,8-dichloro-1-methylspiro[benzo[e]isoxazolo[5,4-c]azepine-4,1'-cyclopropane] (61.9 mg, 0.211 mmol) in toluene (22 mL) was added 4-fluorophenylboronic acid (37 mg, 0.264 mmol) and Pd(Ph$_3$P)$_4$ (11.22 mg, 9.71 µmol). The reaction was evacuated and purged with N$_2$ (g) (3×), followed by addition of aqueous Na$_2$CO$_3$ (211 µl, 0.422 mmol, 2 M). The reaction was heated to 82° C. for 15 min at which time LC-MS analysis indicated complete conversion to desired product. The reaction mixture was cooled to room temperature and diluted with water. The aqueous layer was extracted with EtOAc (3×) and the combined organic extracts were dried over Na$_2$SO$_4$, and concentrated in vacuo. The crude product was purified on Biotage system (5% EtOAc: 95% Hexanes to 10% EtOAc:90% Hexanes). The product 8-chloro-6-(4-fluorophenyl)-1-methylspiro[benzo[e]isoxazolo[5,4-c]azepine-4,1'-cyclopropane] (62 mg, 0.176 mmol, 83% yield) was obtained as a white crystals. LC/MS m/z 353 [M+H]⁺; ¹H NMR (400 MHz, DMSO-d$_6$) δ 7.81-7.77 (m, 1H), 7.75-7.71 (m, 1H), 7.45-7.38 (m, 2H), 7.19-7.26 (m, 3H), 2.52 (s, 3H), 1.29 (s, 4H).

5-(6-(4-Fluorophenyl)-1-methylspiro[benzo[c]isoxazolo[4,5-e]azepine-4,1'-cyclopropan]-8-yl)pyridin-2-amine (Compound 251)

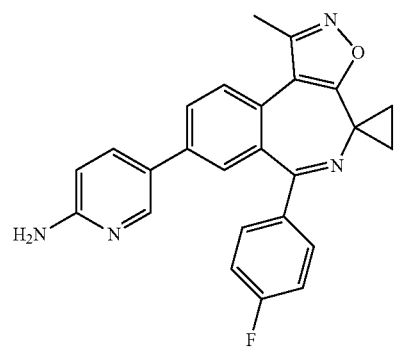 [SMILES: Cc1noc2c1-c1ccc(-c3ccc(N)nc3)cc1C(c1ccc(F)cc1)=NC21CC1]

To a 25 mL round bottom flask containing 8-chloro-6-(4-fluorophenyl)-1-methylspiro[benzo[e]isoxazolo[5,4-c]azepine-4,1'-cyclopropane] (57 mg, 0.162 mmol) was added Pd₂(dba)₃ (9.1 mg, 9.94 μmol), tri-tert-butylphosphonium tetrafluoroborate (6.5 mg, 0.022 mmol), potassium phosphate (77 mg, 0.363 mmol), and 5-(4,4,5,5-tetramethyl-1,3,2-dioxaborolan-2-yl)pyridin-2-amine (56 mg, 0.254 mmol). The flask was evacuated and purged with N₂ (g) (3×), followed by addition of 1,4-dioxane (1 mL) and water (0.05 mL). The flask was evacuated and purged with N₂ (g) (3×) and the reaction mixture was heated to 100° C. After 3 h, ~50% conversion of starting material was observed by LC-MS analysis. The reaction mixture was cooled to room temperature and additional Pd₂(dba)₃ (9.1 mg, 9.94 μmol), tri-tert-butylphosphonium tetrafluoroborate (6.5 mg, 0.022 mmol), potassium phosphate (77 mg, 0.363 mmol), and 5-(4,4,5,5-tetramethyl-1,3,2-dioxaborolan-2-yl)pyridin-2-amine (56 mg, 0.254 mmol) were introduced. The mixture was subsequently heated again for an additional 24 h. LC-MS analysis after 24 h, indicated ~80% conversion to desired product. The reaction mixture was cooled and filtered over a pad of Celite. The filter cake was washed with EtOAc (3×) and the filtrate was concentrated to give a dark brown oil. The oil was purified on Biotage system (25% EtOAc:75% Hexanes to 70% EtOAc:30% Hexanes, then isocratic 70% EtOAc:30% Hexanes). The product was concentrated to give gummy yellow solid that was contaminated with 2-amino-pyridine. The solid was triturated with IPA (1 mL) and Et₂O (1 mL) and filtered. The solids were washed with ether (1 mL) and filtered. The amino pyridine (yellow color) was cleanly removed in the rinses and the product 5-(6-(4-fluorophenyl)-1-methylspiro [benzo[e]isoxazolo[5,4-c]azepine-4,1'-cyclopropane]-8-yl) pyridin-2-amine (0.032 g, 0.078 mmol, 48.3% yield) was isolated as white-solids. LC/MS m/z 411 [M+H]⁺; ¹H NMR (400 MHz, DMSO-d₆) δ 8.16 (d, J=2.49 Hz, 1H), 7.86 (dd, J=1.97, 8.21 Hz, 1H), 7.79 (s, 1H), 7.59 (dd, J=2.60, 8.62 Hz, 1H), 7.49-7.42 (m, 2H), 7.37 (d, J=1.87 Hz, 1H), 7.24-7.15 (m, 2H), 6.49 (dd, J=0.62, 8.72 Hz, 1H), 6.14 (s, 2H), 2.54 (s, 3H), 1.28 (d, J=6.02 Hz, 4H).

EXAMPLE 41

Synthesis of Compound 265

4-bromo-N-methoxy-N,1-dimethyl-1H-pyrazole-3-carboxamide

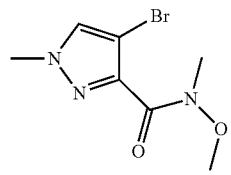

A mixture of 4-bromo-1-methyl-1H-pyrazole-3-carboxylic acid (2.04 g, 10 mmol), 2-(1H-benzotriazole-1-yl)-1,1,3,3-tetramethyluronium tetrafluoroborate (3.21 g, 10 mmol), N,O-dimethylhydroxylamine (1.22 g, 20 mmol) in N,N-Diisopropylethylamine (5 mL) and N,N-Dimethylformamide (20 mL) was stirred for 12 h at room temperature. The mixture was concentrated in vacuum, and the residue was purified by flash chromatography eluting with petroleum ether/ethyl acetate=5:1 to give the titled product as a colorless oil (2.4 g, 97%). LC/MS m/z 247 [M+H]⁺.

(4-bromo-1-methyl-1H-pyrazol-3-yl)(4-chlorophenyl)methanone

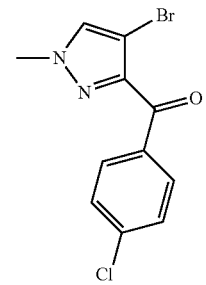 [SMILES: Cn1cc(Br)c(C(=O)c2ccc(Cl)cc2)n1]

To a solution of compound 4-bromo-N-methoxy-N,1-dimethyl-1H-pyrazole-3-carboxamide (1.0 g, 4 mmol) in anhydrous tetrahydrofuran (20 mL) under nitrogen atmosphere was added (4-chlorophenyl)magnesium bromide (8 mL) in tetrahydrofuran (1 M) at 0° C., The resulting mixture was stirred for 2 h at room temperature. The reaction was quenched by saturated solution of ammonium chloride, and dichloromethane (100 mL) was added, the separated organic layer was dried over anhydrous sodium sulfate and concentrated in vacuum. The residue was purified by flash chromatography eluting with petroleum ether/ethyl acetate=5:1 to give the titled product as a white solid (1.0 g, 84%). LC/MS m/z 298 [M+H]⁺; ¹H NMR (300 MHz, CDCl₃) δ 8.10 (d, J=9 Hz, 2H), 7.53 (s, 1H), 7.43 (d, J=9 Hz, 2H), 3.99 (s, 3H).

(4-(3-(4-chlorobenzoyl)-1-methyl-1H-pyrazol-4-yl)-3-methylisoxazol-5-yl)methyl acetate

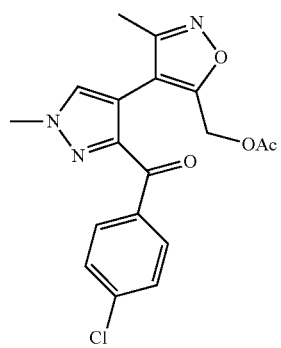 [SMILES: CC(=O)OCc1onc(C)c1-c1cn(C)nc1C(=O)c1ccc(Cl)cc1]

A solution of (4-bromo-1-methyl-1H-pyrazol-3-yl)(4-chlorophenyl)methanone (4-bromo-1-methyl-1H-pyrazol-3-yl)(4-chlorophenyl)methanone (0.5 g, 1.7 mmol), [1,1'-bis(diphenylphosphino)ferrocene]palladium(II) chloride (62 mg, 0.085 mmol), K₂CO₃ (0.94 g, 6.8 mmol), (3-methyl-4-(4,4,5,5-tetramethyl-1,3,2-dioxaborolan-2-yl)isoxazol-5-yl) methyl acetate (0.96 g, 3.4 mmol) in water (2 mL) and 1,4-dioxane (10 mL) was heated at 90° C., and stirred for 4 hours. After cooling to room temperature, DCM (100 mL) was added and the layers separated. The separated organic layer was dried over anhydrous sodium sulfate and concentrated. The residue was purified by flash chromatography eluting (4-chlorophenyl)(4-(5-(hydroxymethyl)-3-methyl-isoxazol-4-yl)-1-methyl-1H-pyrazol-3-yl)methanon

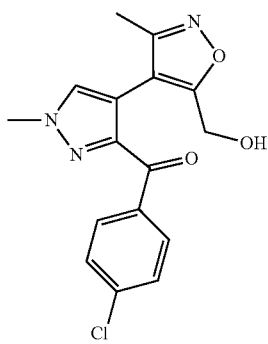 [SMILES: Cc1noc(CO)c1-c1cn(C)nc1C(=O)c1ccc(Cl)cc1]

To a solution of (4-(3-(4-chlorobenzoyl)-1-methyl-1H-pyrazol-4-yl)-3-methylisoxazol-5-yl)methyl acetate (0.3 g, 0.8 mmol) in THF (10 mL), was added NaOH solution (5 mL, 1 N in water). The mixture was stirred for 2 hours at 55° C. After cooling to room temperature, DCM (50 mL) was added and the layers separated. The separated organic layer was dried over anhydrous sodium sulfate and concentrated to afford the titled product as a yellow oil (0.2 g, 75% yield). LC/MS m/z 331 [M+H]$^+$; $^1$H NMR (300 MHz, CDCl$_3$) δ 8.13 (d, J=9 Hz, 2H), 7.45 (d, J=9 Hz, 3H), 4.62 (s, 2H), 4.07 (s, 3H), 2.15 (s, 3H).

(4-(3-(4-chlorobenzoyl)-1-methyl-4H-pyrazol-4-yl)-3-methylisoxazol-5-yl)methyl methanesulfonate

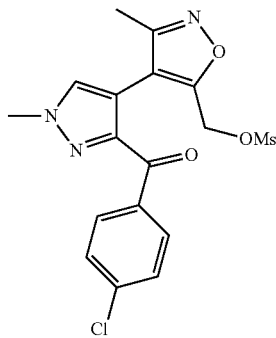 [SMILES: Cc1noc(COS(C)(=O)=O)c1-c1cn(C)nc1C(=O)c1ccc(Cl)cc1]

To a solution of (4-chlorophenyl)(4-(5-(hydroxymethyl)-3-methylisoxazol-4-yl)-1-methyl-1H-pyrazol-3-yl)methanone (0.05 g, 0.15 mmol) in DCM (10 mL), was added triethylamine (0.1 mL) and methane sulfonyl chloride (0.05 mL) at room temperature. The mixture was stirred for 2 h at room temperature. DCM (50 mL) and saturated sodium bicarbonate solution (20 mL) were added. The combined organic layers were dried over anhydrous sodium sulfate and concentrated to afford the titled product as yellow oil (0.035 g, 56%). LC/MS m/z 409 [M+H]$^+$.

(4-(5-(azidomethyl)-3-methylisoxazol-4-yl)-1-methyl-1H-pyrazol-3-yl)(4-chlorophenyl)methanone

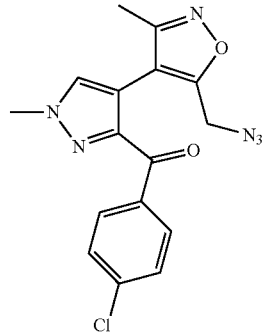 [SMILES: Cc1noc(CN=[N+]=[N-])c1-c1cn(C)nc1C(=O)c1ccc(Cl)cc1]

A mixture of (4-(3-(4-chlorobenzoyl)-1-methyl-1H-pyrazol-4-yl)-3-methylisoxazol-5-yl)methyl methanesulfonate (35 mg, 0.09 mmol), sodium azide (12 mg, 0.18 mmol) in N,N-dimethylformamide (10 mL) was heated to 80° C. and stirred for 10 h. After cooling to room temperature, the mixture was concentrated, and the residue was purified by flash chromatography eluting with petroleum ether/ethyl acetate=1:3 to give the titled product as a colorless oil (30 mg, 94%). LC/MS: m/z 356 [M+H]$^+$; $^1$H NMR (300 MHz, CDCl$_3$) δ 8.16 (d, J=9 Hz, 2H), 7.50 (s, 1H), 7.46 (d, J=9 Hz, 2H), 4.37 (s, 2H), 4.09 (s, 3H), 2.19 (s, 3H).

6-(4-chlorophenyl)-1,8-dimethyl-4,8-dihydroisoxazolo[5,4-c]pyrazolo[4,3-e]azepine (Compound 265)

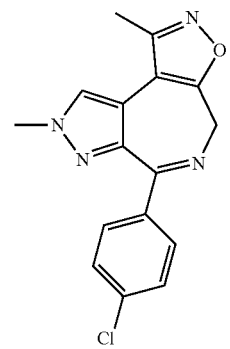 [SMILES: Cc1noc2c1-c1cn(C)nc1C(c1ccc(Cl)cc1)=NC2]

To a solution of (4-(5-(azidomethyl)-3-methylisoxazol-4-yl)-1-methyl-1H-pyrazol-3-yl)(4-chlorophenyl)methanone (0.03 g, 0.08 mmol) in anhydrous THF (10 mL), was added triphenylphosphine (32 mg, 0.12 mmol) at room temperature. The mixture was stirred for 12 h at room temperature. The mixture was concentrated and the residue was purified by flash chromatography eluting with (petroleum ether/ethyl acetate=1:3) to afford the title compound as a white solid (15 mg, 60% yield). LC/MS: m/z 312 [M+H]$^+$; $^1$H NMR (300 MHz, CDCl$_3$) δ 7.62 (d, J=9 Hz, 3H), 7.36 (d, J=9 Hz, 2H), 4.87 (s, 2H), 4.08 (s, 3H), 2.45 (s, 3H).

EXAMPLE 42

IC50 Measurements for Inhibitors Using BRD4 Alphalisa Binding Assay

His/Hag epitope tagged BRD4 $BD1_{42-168}$ was cloned, expressed and purified to homogeneity. BRD4 binding and inhibition was assessed by monitoring the engagement of biotinylated H4-tetraacetyl peptide (Millipore #12-379) with the target using the AlphaLisa technology (Perkin-Elmer). Specifically, in a 384 well ProxiPlate BRD4(BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minute incubation at room temperature Alpha streptavidin donor beads and AlphaLisa anti-Flag acceptor beads were added to a final concentration of 10 ug/mL each. After three hours equilibration plates were read on an Envision instrument and $IC_{50}$s calculated using a four parameter non-linear curve fit. The results of this assay are set forth in Table 2, below.

TABLE 2

Activity of Additional Exemplary Compounds of the Invention.

| Compound No. | BRD4 Alphascreen $IC_{50}$ |
|---|---|
| 202 | + |
| 203 | + |
| 204 | +++ |
| 205 | ++ |
| 206 | + |
| 207 | + |
| 208 | + |
| 209 | + |
| 210 | + |
| 211 | +++ |
| 212 | +++ |
| 213 | +++ |
| 214 | + |
| 215 | + |
| 216 | + |
| 217 | +++ |
| 218 | +++ |
| 219 | + |
| 220 | + |
| 221 | + |
| 222 | +++ |
| 223 | + |
| 224 | +++ |
| 225 | +++ |
| 226 | + |
| 250 | +++ |
| 251 | + |
| 265 | +++ |

In Table 2, "+" represents a value under 0.50 µM; "++" a value between 0.50 µM and 1 µM; and "+++" a value greater than 1 µM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

We claim:
1. A compound of formula II:

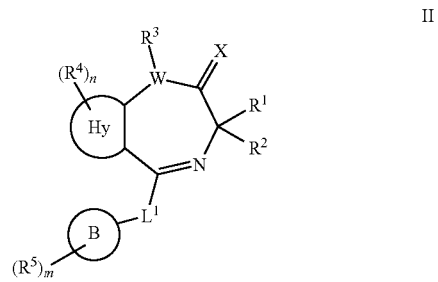

or a pharmaceutically acceptable salt thereof, wherein:

Hy is a 5-membered fused heteroaryl ring having 2-3 heteroatoms independently selected from nitrogen, oxygen, or sulfur, or a 6-membered fused heteroaryl ring having 2-3 nitrogen atoms;

Ring B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

$L^1$ is a covalent bond or an optionally substituted bivalent $C_{1-6}$ hydrocarbon chain wherein one or two methylene units is optionally replaced by —NR'—, —N(R')C(O)—, —C(O)N(R')-, —N(R')SO₂—, —SO₂N(R')—, —O—, —C(O)—, —OC(O)—, —C(O)O—, —S—, —SO— or —SO₂—;

p is 0-3;

$R^x$ is halogen, optionally substituted $C_{1-6}$ aliphatic, —OR, —SR, —CN, —N(R')₂, —C(O)R, —C(S)R, —CO₂R, —C(O)N(R')₂, —C(O)SR, —C(O)C(O)R, —C(O)CH₂C(O)R, —C(S)N(R')₂, —C(S)OR, —S(O)R, —SO₂R, —SO₂N(R')₂, —N(R')C(O)R, —N(R')C(O)N(R')₂, —N(R')C(S)N(R')₂, —N(R')SO₂R, —N(R')SO₂N(R')₂, —N(R')N(R')₂, —N(R')C(=N(R'))N(R')₂, —C=NN(R')₂, —C=NOR, —C(=N(R'))N(R')₂, —OC(O)R, —OC(O)N(R')₂;

$R^1$ and $R^2$ are taken together with their intervening atoms to form an optionally substituted 3-7 membered saturated or partially unsaturated spiro-fused ring having 0-2 heteroatoms independently selected from nitrogen, oxygen, or sulfur;

each R is independently hydrogen or an optionally substituted group selected from $C_{1-6}$ aliphatic, phenyl, a 3-7 membered saturated or partially unsaturated carbocyclic ring, a 7-10 membered bicyclic saturated, partially unsaturated, or aryl ring, a 5-6 membered monocyclic heteroaryl ring having 1-3 heteroatoms independently selected from nitrogen, oxygen, and sulfur, a 4-7 membered saturated or partially unsaturated heterocyclic ring having 1-2 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R' on the same nitrogen are taken together with their intervening atoms to form an optionally substituted group selected from a 4-7 membered monocyclic saturated or partially unsaturated ring having 1-2 heteroatoms independently selected from nitrogen, oxygen, and sulfur, or a 7-12 membered bicyclic saturated, partially unsaturated, or aromatic fused ring having 1-3 heteroatoms independently selected from nitrogen, oxygen, and sulfur;

W is

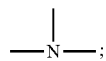

R$^3$ and X are taken together with their intervening atoms to form an optionally substituted triazolyl ring;

each of m and n is independently 0-4, as valency permits; and each of R$^4$ and R$^5$ is independently —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$.

2. The compound according to claim 1, wherein Hy is pyrimidino, pyrazino, isothiazolo, or pyridazino.

3. The compound according to claim 1, wherein Ring B is phenyl.

4. The compound according to claim 1, wherein L$^1$ is a covalent bond.

5. A compound selected from

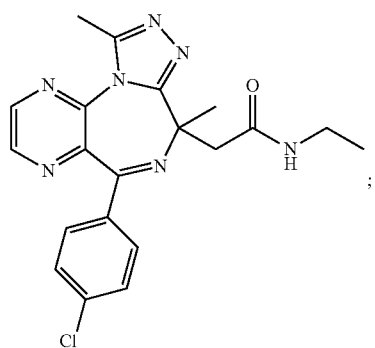

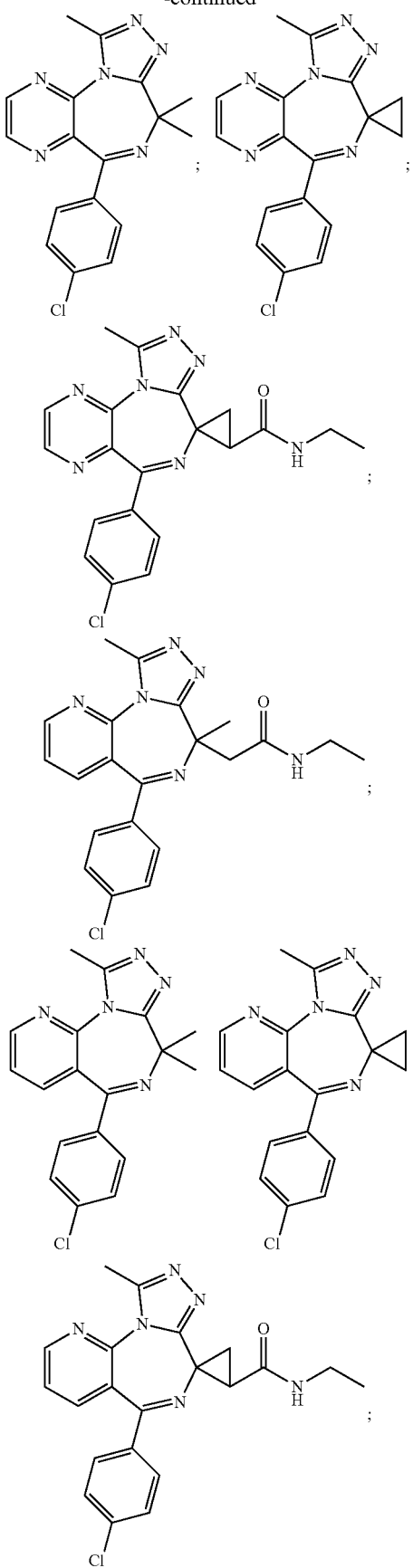

121
-continued
122
-continued
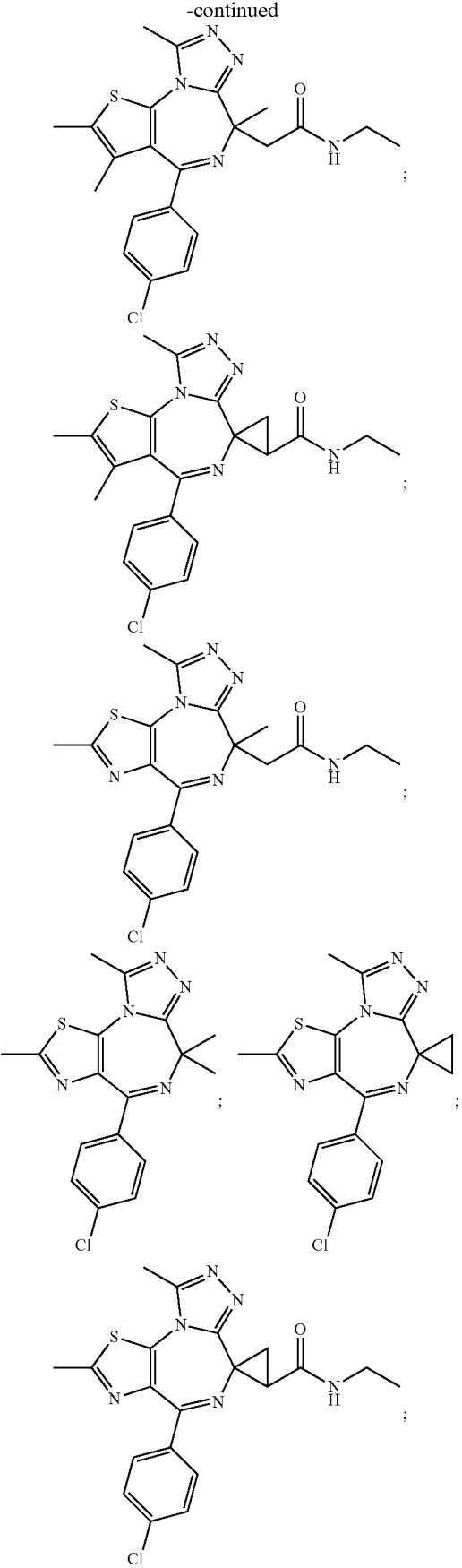
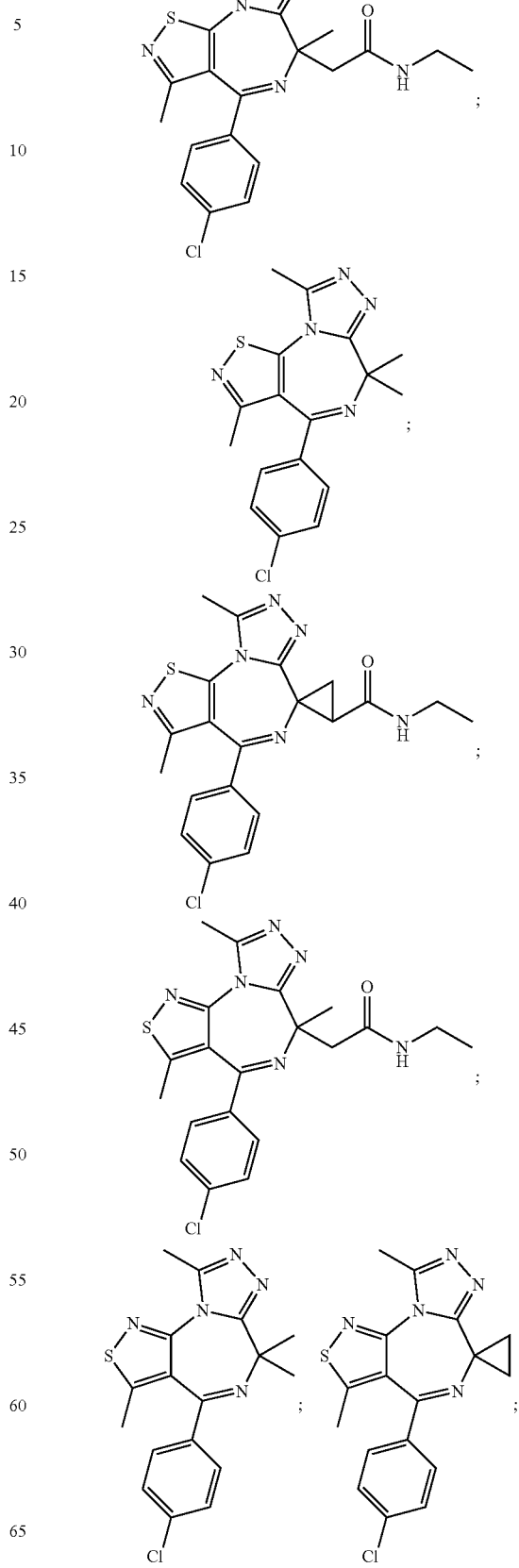

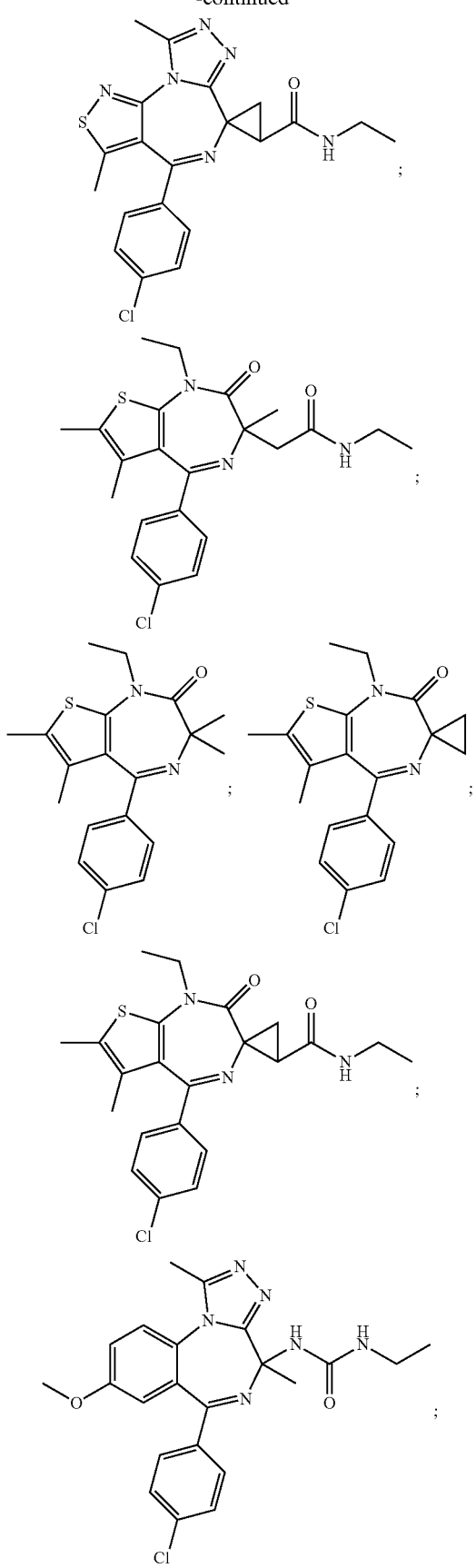
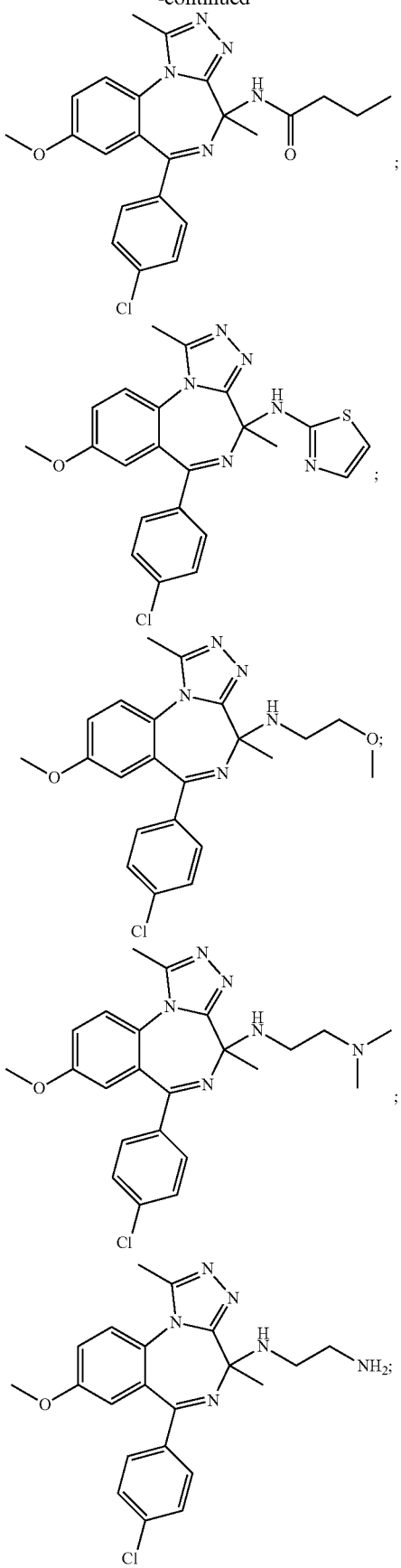

125
-continued
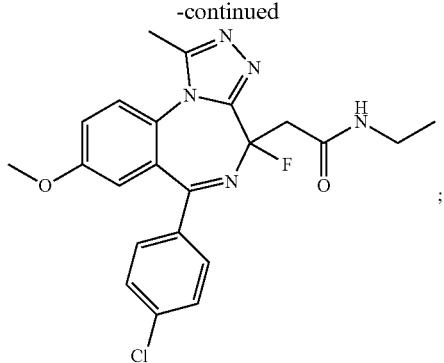
;
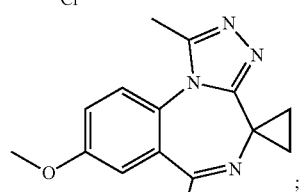
;
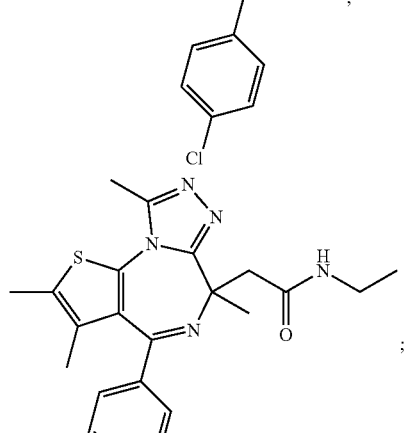
;
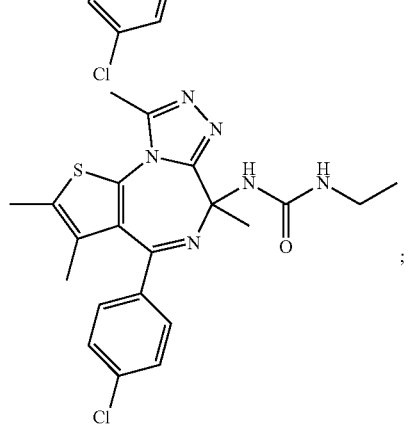
;
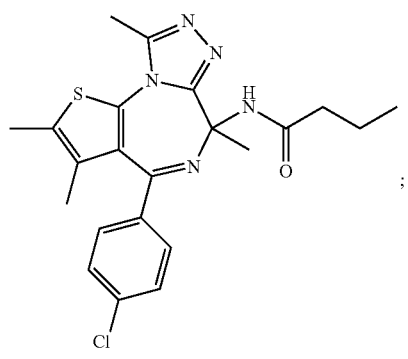
;
126
-continued
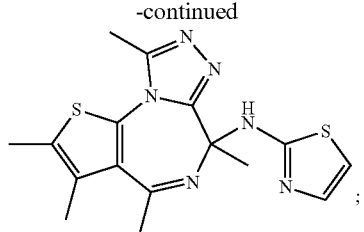
;
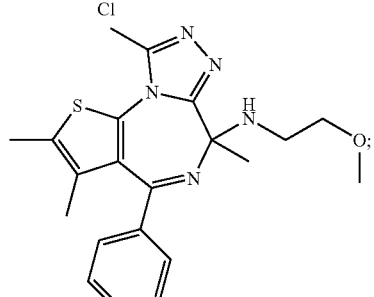
;
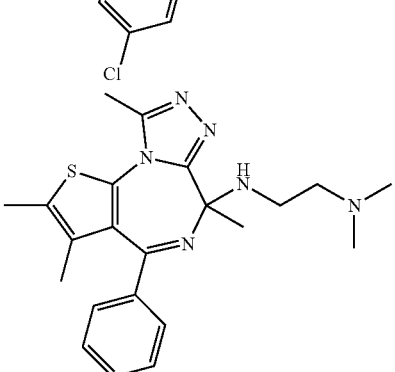
;
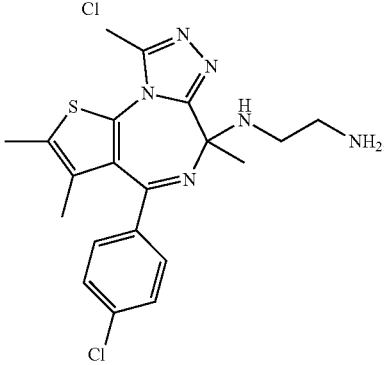
;
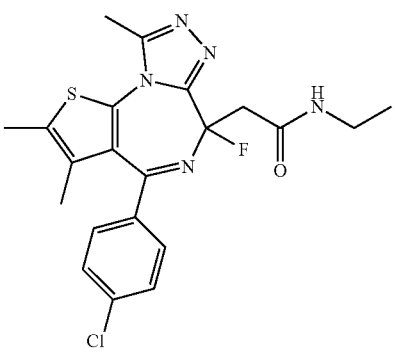
;

127
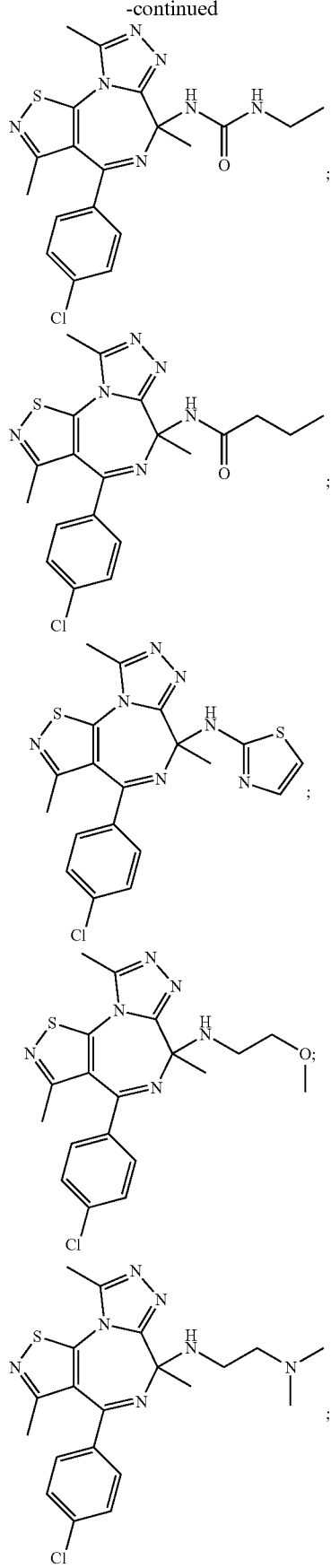
128
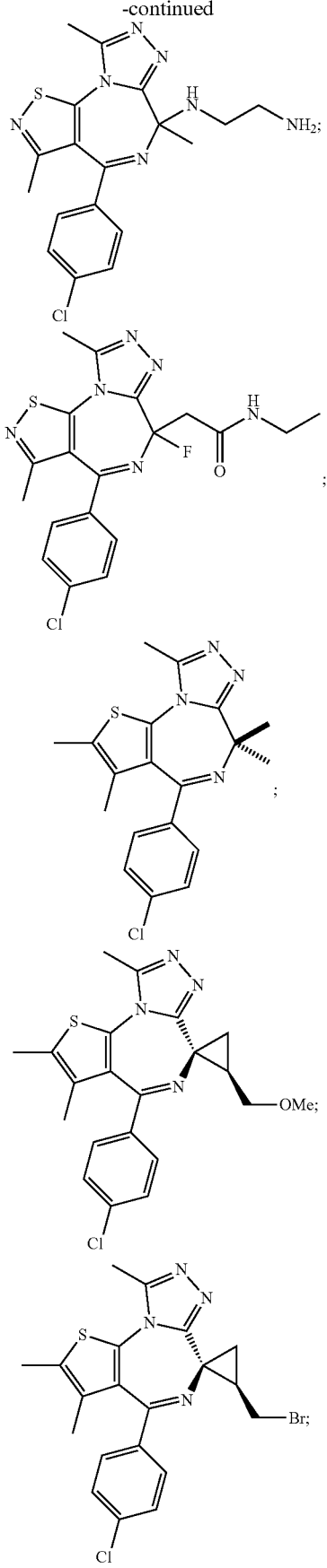

129
-continued

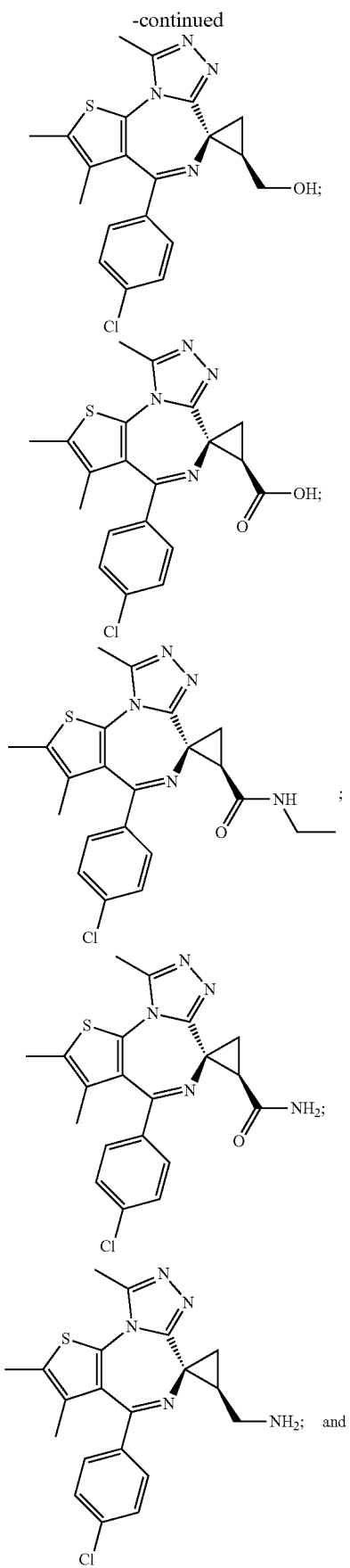

130
-continued

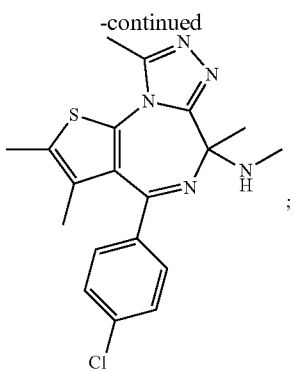

or a pharmaceutically acceptable salt thereof.

6. A composition comprising a compound of claim 1 and a pharmaceutically acceptable adjuvant, carrier, or vehicle.

7. The compound of claim 1, wherein the compound is of formula I-a-ii:

I-a-ii

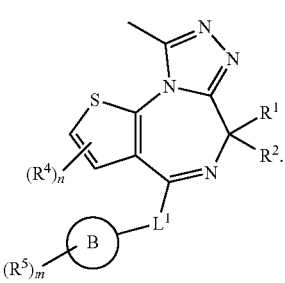

or a pharmaceutically acceptable salt thereof.

8. A compound of formula I:

I

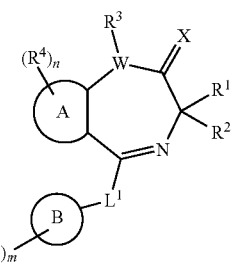

or a pharmaceutically acceptable salt thereof, wherein:
Ring A is pyrido, pyrimidino, pyrazino, pyridazino, triazino, furano, pyrrolo, thiazolo, isothiazolo, oxazolo, isoxazolo, pyrazolo, or imidazole;
Ring B is a 3-7 membered saturated or partially unsaturated carbocyclic ring, phenyl, an 8-10 membered bicyclic saturated, partially unsaturated, or aryl ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

$L^1$ is a covalent bond or an optionally substituted bivalent $C_{1-6}$ hydrocarbon chain wherein one or two methylene units is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—;

$R^1$ is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$, or —(CH$_2$)$_p$R$^x$;

p is 0-3;

$R^x$ is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$;

$R^2$ is halogen, —CN, —SR, or optionally substituted $C_{1-6}$ aliphatic, or:

$R^1$ and $R^2$ are taken together with their intervening atoms to form an optionally substituted 3-7 membered saturated or partially unsaturated spiro-fused ring having 0-2 heteroatoms independently selected from nitrogen, oxygen, or sulfur;

each R is independently hydrogen or an optionally substituted group selected from $C_{1-6}$ aliphatic, phenyl, a 3-7 membered saturated or partially unsaturated carbocyclic ring, a 7-10 membered bicyclic saturated, partially unsaturated, or aryl ring, a 5-6 membered monocyclic heteroaryl ring having 1-3 heteroatoms independently selected from nitrogen, oxygen, and sulfur, a 4-7 membered saturated or partially unsaturated heterocyclic ring having 1-2 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

each R' is independently —R, —C(O)R, —C(S)R, —CO$_2$R, —C(O)N(R)$_2$, —C(S)N(R)$_2$, —S(O)R, —SO$_2$R, —SO$_2$N(R)$_2$, or two R' on the same nitrogen are taken together with their intervening atoms to form an optionally substituted group selected from a 4-7 membered monocyclic saturated or partially unsaturated ring having 1-2 heteroatoms independently selected from nitrogen, oxygen, and sulfur, or a 7-12 membered bicyclic saturated, partially unsaturated, or aromatic fused ring having 1-3 heteroatoms independently selected from nitrogen, oxygen, and sulfur;

W is

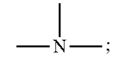

$R^3$ and X are taken together with their intervening atoms to form an optionally substituted triazolyl ring;

each of m and n is independently 0-4, as valency permits;

$R^4$ is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$; and $R^5$ is —R, halogen, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$;

provided that:

when Ring A is pyrido, $L^1$ is a covalent bond, Ring B is aryl or heteroaryl, and $R^2$ is $C_{1-6}$ alkyl, then $R^1$ is other than —CO$_2$R or —(CH$_2$)$_p$R$^x$ wherein R$^x$ is —CO$_2$R; and when Ring A is pyrido, $L^1$ is a covalent bond, Ring B is aryl or heteroaryl, then $R^1$ and $R^2$ are not taken together to form an optionally substituted dihydropyrimidinedione or imidazolidinedione.

9. The compound of claim 8, wherein the compound is of formula I-a:

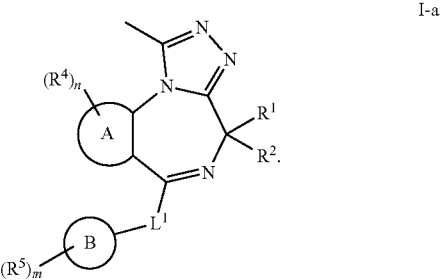

or a pharmaceutically acceptable salt thereof.

10. The compound of claim 9, wherein Ring A is pyrimidino, pyrazino, or pyridazino.

11. The compound of claim 10, wherein $L^1$ is a covalent bond; $R^1$ is optionally substituted $C_{1-6}$ aliphatic; $R^2$ is optionally substituted $C_{1-6}$ aliphatic.

12. A composition comprising a compound of claim 8 and a pharmaceutically acceptable adjuvant, carrier, or vehicle.

* * * * *